United States Patent
Reid et al.

(10) Patent No.: US 11,921,103 B2
(45) Date of Patent: Mar. 5, 2024

(54) METHOD OF OPERATING A MEASUREMENT SYSTEM TO ANALYZE A POLYMER

(71) Applicant: Oxford Nanopore Technologies PLC, Oxford (GB)

(72) Inventors: Stuart William Reid, Oxford (GB); Gavin Harper, Oxford (GB); Clive Gavin Brown, Oxford (GB); James Anthony Clarke, Oxford (GB); Andrew John Heron, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 0 days.

(21) Appl. No.: 16/449,272

(22) Filed: Jun. 21, 2019

(65) Prior Publication Data

US 2019/0310242 A1    Oct. 10, 2019

Related U.S. Application Data

(63) Continuation of application No. 15/487,329, filed on Apr. 13, 2017, which is a continuation of application No. 14/346,549, filed as application No. PCT/GB2012/052343 on Sep. 21, 2012, now abandoned.

(60) Provisional application No. 61/617,880, filed on Mar. 30, 2012, provisional application No. 61/538,721, filed on Sep. 23, 2011.

(51) Int. Cl.
| | |
|---|---|
| *G01N 33/487* | (2006.01) |
| *B82Y 15/00* | (2011.01) |
| *C12Q 1/6869* | (2018.01) |
| *G01N 27/447* | (2006.01) |
| *G01N 33/483* | (2006.01) |
| *G06F 17/18* | (2006.01) |
| *G06N 7/01* | (2023.01) |
| *G16B 30/00* | (2019.01) |
| *G16B 30/10* | (2019.01) |

(52) U.S. Cl.
CPC ..... *G01N 33/48721* (2013.01); *C12Q 1/6869* (2013.01); *G01N 27/44791* (2013.01); *G01N 33/483* (2013.01); *G06F 17/18* (2013.01); *G06N 7/01* (2023.01); *G16B 30/00* (2019.02); *G16B 30/10* (2019.02); *B82Y 15/00* (2013.01)

(58) Field of Classification Search
None
See application file for complete search history.

(56) References Cited

U.S. PATENT DOCUMENTS

| | | |
|---|---|---|
| 5,795,782 A | 8/1998 | Church et al. |
| 6,128,587 A | 10/2000 | Sjolander |
| 7,625,706 B2 * | 12/2009 | Akeson ............ B01L 3/502707 435/6.1 |
| 7,731,826 B2 | 6/2010 | Hibbs et al. |
| 8,324,914 B2 | 12/2012 | Chen et al. |
| 8,452,546 B1 * | 5/2013 | Lathrop ........... G01N 33/48721 702/20 |
| 9,057,102 B2 | 6/2015 | Turner et al. |
| 9,121,064 B2 | 9/2015 | Turner et al. |
| 9,127,313 B2 | 9/2015 | Brown et al. |
| 9,546,400 B2 | 1/2017 | Turner et al. |
| 9,556,480 B2 | 1/2017 | Turner et al. |
| 9,678,056 B2 | 6/2017 | Turner et al. |
| 9,738,929 B2 | 8/2017 | Turner et al. |
| 10,131,943 B2 | 11/2018 | Reid et al. |
| 10,689,697 B2 | 6/2020 | Reid et al. |
| 11,085,077 B2 | 8/2021 | Reid et al. |

(Continued)

FOREIGN PATENT DOCUMENTS

| | | |
|---|---|---|
| EP | 1351183 A2 | 10/2003 |
| EP | 1544310 A2 | 6/2005 |

(Continued)

OTHER PUBLICATIONS

Thompson et al. (Nucleic Acids Research, 1994, vol. 22, No. 22 4673-4680). (Year: 1994).*
Edgar et al. (Nucleic Acids Research, 2004, vol. 32, No. 5, pp. 1792-1797). (Year: 2004).*
Bates et al. (Biophys J. Apr. 2003; 84(4): 2366-2372). (Year: 2003).*
Stoddart et al. (PNAS, 2009, vol. 106, No. 19, pp. 7702-7707) (Year: 2009).*
Muzard et al. (Biophysical Journal, vol. 98, May 2010, pp. 2170-2178). (Year: 2010).*

(Continued)

*Primary Examiner* — Pablo S Whaley
(74) *Attorney, Agent, or Firm* — Wolf, Greenfield & Sacks, P.C.

(57) ABSTRACT

A sequence of polymer units in a polymer (3), eg. DNA, is estimated from at least one series of measurements related to the polymer, eg. ion current as a function of translocation through a nanopore (1), wherein the value of each measurement is dependent on a k-mer being a group of k polymer units (4). A probabilistic model, especially a hidden Markov model (HMM), is provided, comprising, for a set of possible k-mers: transition weightings representing the chances of transitions from origin k-mers to destination k-mers; and emission weightings in respect of each k-mer that represent the chances of observing given values of measurements for that k-mer. The series of measurements is analysed using an analytical technique, eg. Viterbi decoding, that refers to the model and estimates at least one estimated sequence of polymer units in the polymer based on the likelihood predicted by the model of the series of measurements being produced by sequences of polymer units. In a further embodiment, different voltages are applied across the nanopore during translocation in order to improve the resolution of polymer units.

13 Claims, 23 Drawing Sheets
Specification includes a Sequence Listing.

(56) References Cited

U.S. PATENT DOCUMENTS

| | | | |
|---|---|---|---|
| 11,401,549 | B2 | 8/2022 | Reid et al. |
| 2003/0099951 | A1 | 5/2003 | Akeson et al. |
| 2005/0159898 | A1 | 7/2005 | Yasuda et al. |
| 2005/0202444 | A1 | 9/2005 | Zhu |
| 2005/0272923 | A1 | 12/2005 | Zhang et al. |
| 2006/0019259 | A1 | 1/2006 | Joyce |
| 2006/0086626 | A1 | 4/2006 | Joyce |
| 2007/0161028 | A1 | 7/2007 | Schwartz et al. |
| 2010/0331194 | A1 | 12/2010 | Turner et al. |
| 2011/0121840 | A1 | 5/2011 | Sanghera et al. |
| 2011/0226623 | A1 | 9/2011 | Timp et al. |
| 2013/0071837 | A1* | 3/2013 | Winters-Hilt ........ C12Q 1/6869 435/6.11 |
| 2014/0255918 | A1 | 9/2014 | Olasagasti et al. |
| 2015/0057948 | A1 | 2/2015 | Reid et al. |
| 2015/0152492 | A1 | 6/2015 | Brown et al. |
| 2015/0152495 | A1* | 6/2015 | Stava ..................... C07K 14/35 435/6.19 |
| 2015/0344944 | A1 | 12/2015 | Reid et al. |
| 2016/0162634 | A1 | 6/2016 | Reid et al. |
| 2017/0091427 | A1 | 3/2017 | Massingham |
| 2017/0096703 | A1 | 4/2017 | Dolan et al. |
| 2017/0219557 | A1 | 8/2017 | Reid et al. |
| 2017/0233804 | A1 | 8/2017 | Reid et al. |
| 2019/0154655 | A1 | 5/2019 | Reid et al. |
| 2019/0203286 | A1 | 7/2019 | Reid et al. |
| 2021/0079460 | A1 | 3/2021 | Reid et al. |
| 2022/0064724 | A1 | 3/2022 | Reid et al. |
| 2023/0167494 | A1 | 6/2023 | Reid et al. |

FOREIGN PATENT DOCUMENTS

| | | | |
|---|---|---|---|
| JP | H11-178575 | | 7/1999 |
| JP | 2002-325581 | | 11/2002 |
| JP | 2005-257687 | A | 9/2005 |
| JP | 2006-119140 | A | 5/2006 |
| JP | 2010-524436 | A | 7/2010 |
| JP | 2010-539966 | | 12/2010 |
| JP | 2014-531901 | A | 12/2014 |
| WO | WO 2000/079257 | A1 | 12/2000 |
| WO | WO 2002/42496 | | 5/2002 |
| WO | WO 2006-028508 | A2 | 3/2006 |
| WO | WO 2007/117832 | A2 | 10/2007 |
| WO | WO 2007/137225 | A2 | 11/2007 |
| WO | WO 2008/092760 | A1 | 8/2008 |
| WO | WO 2008/102120 | A1 | 8/2008 |
| WO | WO 2008/124107 | | 10/2008 |
| WO | WO 2010/053820 | A1 | 5/2010 |
| WO | WO 2010/055307 | A1 | 5/2010 |
| WO | WO-2010109197 | A2 * | 9/2010 ........... C12Q 1/6869 |
| WO | WO 2010/122293 | | 10/2010 |
| WO | WO 2011/067559 | | 6/2011 |
| WO | WO 2012/021149 | A1 | 2/2012 |
| WO | WO 2012/109483 | A2 | 8/2012 |
| WO | WO 2012/135658 | A2 | 10/2012 |
| WO | WO 2012/138357 | | 10/2012 |
| WO | WO 2012/164270 | A1 | 12/2012 |
| WO | WO 2013/014451 | | 1/2013 |
| WO | WO 2013/041878 | A1 | 3/2013 |
| WO | WO 2013/057495 | A2 | 4/2013 |
| WO | WO 2013/098561 | A1 | 7/2013 |
| WO | WO 2013/098562 | A2 | 7/2013 |
| WO | WO 2013/109970 | | 7/2013 |
| WO | WO 2013/121224 | | 8/2013 |
| WO | WO 2013/159042 | | 10/2013 |
| WO | WO 2013/185137 | A1 | 12/2013 |
| WO | WO 2014/013259 | | 1/2014 |
| WO | WO 2014/064443 | | 5/2014 |
| WO | WO 2014/064444 | | 5/2014 |
| WO | WO 2014/096830 | A1 | 6/2014 |

OTHER PUBLICATIONS

Alcock et al., Time-series Similarity Queries Employing a Feature-Based Approach. Proceedings of the 7th Hellenic Conference on Informatics (HCI '99); University of Ioannina, Greece, pp. 1-9, Aug. 26-29, 1999.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Ashkenasy et al., Recognizing a single base in an individual DNA strand: a step toward DNA sequencing in nanopores. Angew Chem Int Ed Engl. Feb. 18, 2005;44(9):1401-4.

Batzoglou, Algorithmic challenges in mammalian whole-genome sequence assembly. In: Encyclopedia of genomics, proteomics and bioinformatics. John Wiley and Sons, New York. 2005.

Bell et al., DNA origami nanopores. Nano Lett. Jan. 11, 2012;12(1):512-7. doi: 10.1021/nl204098n. Epub Dec. 29, 2011.

Bokhari et al., A parallel graph decomposition algorithm for DNA sequencing with nanopores. Bioinformatics. Apr. 1, 2005;21(7):889-96. Epub Nov. 11, 2004.

Boufounos et al., Basecalling using hidden Markov models. Journal of the Franklin Institute, vol. 341 :23-36 (2004).

Braha et al., Designed protein pores as components for biosensors. Chem Biol. Jul. 1997;4(7):497-505.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Technologies, Inc.'s Motion to Dismiss and Request for Scheduling Conference. Nov. 30, 2017.

Case 1:17-cv-01353-RGA Document 10. Oxford's opening brief in support of its motion to partially dismiss PacBio's complaint for patent infringement. Nov. 16, 2017.

Chao et al., Constrained sequence alignment. Bull Math Biol. May 1993;55(3):503-24.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Dahl et al., Direct observation of translocation in individual DNA polymerase complexes. J Biol Chem. Apr. 13, 2012;287(16):13407-21. doi:10.1074/jbc.M111.338418. Epub Feb. 29, 2012.

Derrington et al., Nanopore DNA sequencing with MspA. Proc Natl Acad Sci U S A. Sep. 14, 2010;107(37):16060-5. doi: 10.1073/pnas.1001831107.

Devereux et al., A comprehensive set of sequence analysis programs for the VAX. Nucleic Acids Res. Jan. 11, 1984;12(1 Pt 1):387-95.

EP Communication pursuant to Rule 114(2) EPC for application No. 13706058.8 dated Oct. 19, 2017.

Ervin et al., Simultaneous alternating and direct current readout of protein ion channel blocking events using glass nanopore membranes. Anal Chem. Mar. 15, 2008;80(6):2069-76. doi: 10.1021/ac7021103. Epub Feb. 23, 2008.

Fariselli et al., A new decoding algorithm for hidden Markov models improves the prediction of the topology of all-beta membrane proteins. BMC Bioinformatics. Dec. 1, 2005;6 Suppl 4:S12.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

(56) References Cited

OTHER PUBLICATIONS

Gordon, Classification. 2nd edition. Chapman and Hall/CRC. 69-109. 1999.
Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.
He et al., Controlling DNA translocation through gate modulation of nanopore wall surface charges. ACS Nano. Jul. 26, 2011;5(7):5509-18. doi: 10.1021/nn201883b. Epub Jun. 17, 2011.
Healy, Nanopore-based single-molecule DNA analysis. Nanomedicine (Lond). Aug. 2007;2(4):459-81.
Heger, Method to Improve Nanopore Sequencing Accuracy Developed by University of Washington Team. GenomeWeb. Apr. 30, 2019. Retrieved from https://www.genomeweb.com/sequencing/method-improve-nanopore-sequencing-accuracy-developed-university-washington-team#.XpdXveRYY0R. 2 pages.
Hein et al., Statistical alignment: computational properties, homology testing and goodness-of-fit. J Mol Biol. Sep. 8, 2000;302(1):265-79.
Heron et al., Simultaneous measurement of ionic current and fluorescence from single protein pores. J Am Chem Soc. Feb. 11, 2009;131(5):1652-3. doi: 10.1021/ja808128s.
Higgins et al., CLUSTAL: a package for performing multiple sequence alignment on a microcomputer. Gene. Dec. 15, 1988;73(1):237-44.
Ivanov et al., DNA tunneling detector embedded in a nanopore. Nano Lett. Jan. 12, 2011;11(1):279-85. doi: 10.1021/nl103873a. Epub Dec. 6, 2010.
Jain et al., Improved data analysis for the MinION nanopore sequencer. Nat Methods. Apr. 2015;12(4): 351-356. EPub Feb. 16, 2015. doi: 10.1038/nmeth.3290. Author Manuscript.
Karp et al., Efficient randomized pattern-matching algorithms. IBM J. Res. Development. 1987;31(2):249-260.
Kasianowicz et al., Nanoscopic porous sensors. Annu Rev Anal Chem (Palo Alto Calif). 2008;1:737-66. doi: 10.1146/annurev.anchem.1.031207.112818.
Kaxiras et al. Multiscale simulations of complex systems: computation meets reality. Sci Model Simul. 2008; 15:59-65.
Kent WJ. Blat—the BLAST-like alignment tool. Genome Res. Apr. 2002;12(4):656-64.
Khreich et al., A survey of techniques for incremental learning of HMM parameters. J Info Sciences. Aug. 2012;197:105-130.
Kowalczyk et al., Slowing down DNA translocation through a nanopore in lithium chloride. Nano Lett. Feb. 8, 2012;12(2):1038-44. doi: 10.1021/nl204273h. Epub Jan. 27, 2012.
Lam et al., HMMConverter 1.0: a toolbox for hidden Markov models. Nucleic Acids Res. Nov. 2009;37(21):e139. doi: 10.1093/nar/gkp662.
Lathrop et al., Monitoring the escape of DNA from a nanopore using an alternating current signal. J Am Chem Soc. Feb. 17, 2010;132(6):1878-85. doi:10.1021/ja906951g.
Liang et al., Bayesian Basecalling for DNA Sequence Analysis using Hidden Markov Models. Proceedings of 2006 IEEE Conference on Information Sciences and Systems, CISS, pp. 1599-1604 (2006).
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.
Loose et al., Real-time selective sequencing using nanopore technology. Nat Methods. Sep. 2016;13(9): 751-754. EPub Jul. 25, 2016. doi: 10.1038/nmeth.3930.
Luan et al., Base-by-base ratcheting of single stranded DNA through a solid-state nanopore. Phys Rev Lett. Jun. 11, 2010;104(23):238103. Epub Jun. 10, 2010.
Luan et al., Control and reversal of the electrophoretic force on DNA in a charged nanopore. J Phys Condens Matter. Nov. 17, 2010;22(45):454123. doi:10.1088/0953-8984/22/45/454123. Epub Oct. 29, 2010.

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Mikheyev et al., A first look at the Oxford Nanopore MinION sequencer. Mol Ecol Resour. Nov. 2014;14(6):1097-102. doi: 10.1111/1755-0998.12324. Epub Sep. 24, 2014.
Montal et al., Formation of bimolecular membranes from lipid monolayers and a study of their electrical properties. Proc Natl Acad Sci U S A. Dec. 1972;69(12):3561-6.
Nakane et al. Nanopore sensors for nucleic acid analysis. J. Phys.: Condens. Matter 15 (2003) R1365-R1393.
Olasagasti et al., Replication of individual DNA molecules under electronic control using a protein nanopore. Nat Nanotechnol. Nov. 2010;5(11):798-806. doi: 10.1038/nnano.2010.177. Epub Sep. 26, 2010.
Quinlan et al., C.45: Programs for Machine Learning. Morgan Kaufmann Publishers, ISBN 1-55860-238-0. Ed.: Langley. 1-114. 1993.
Schneider et al., DNA sequencing with nanopores. Nat Biotechnol. Apr. 10, 2012;30(4):326-8. doi: 10.1038/nbt.2181.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Nucleobase recognition in ssDNA at the central constriction of the alpha-hemolysin pore. Nano Lett. Sep. 8, 2010;10(9):3633-7. doi: 10.1021/nl101955a.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Suzuki et al., A New HMnet Construction Algorithm Requiring No Contextual Factors. IEICE. Jun. 1995;E78:662-668.
Timp et al., DNA base-calling from a nanopore using a Viterbi algorithm. Biophys J. May 16, 2012;102(10):L37-9. doi: 10.1016/j.bpj.2012.04.009. Epub May 15, 2012.
United States District Court for the District of Delaware Order. *Pacific Biosciences of California, Inc.* v. *Oxford Nanopore Technologies, Inc.* Civil Action No. 17-275-RGA. Nov. 9, 2017.
United States Patent and Trademark Office. *Oxford Nanopore Technologies Inc.* Petition v *Pacific Biosciences of California, Inc.* for U.S. Pat. No. 9,546,400. Inter Partes Review of claims 1-15. 81 pages. Mar. 15, 2018.
Warren et al., Assembling millions of short DNA sequences using SSAKE. Bioinformatics. Feb. 15, 2007;23(4):500-1. Epub Dec. 8, 2006.
Winters-Hilt et al., A novel, fast, HMM-with-Duration implementation—for application with a new, pattern recognition informed, nanopore detector. BMC Bioinformatics. Nov. 1, 2007;8 Suppl 7:S19.
Winters-Hilt et al., Highly accurate classification of Watson-Crick basepairs on termini of single DNA molecules. Biophys J. Feb. 2003;84(2 Pt 1):967-76.
Winters-Hilt, Machine learning methods for channel current cheminformatics, biophysical analysis, and bioinformatics. University of California Santa Cruz. Mar. 2003. Dissertation. 176 pages.
Zeng et al., PyroHMMvar: a sensitive and accurate method to call short indels and SNPs for Ion Torrent and 454 data. Bioinformatics. Nov. 15, 2013;29(22):2859-68. doi: 10.1093/bioinformatics/btt512. Epub Aug. 31, 2013.
Zerbino et al., Velvet: algorithms for de novo short read assembly using de Bruijn graphs. Genome Res. May 2008;18(5):821-9. doi: 10.1101/gr.074492.107. Epub Mar. 18, 2008.
Zhu et al., Bayesian adaptive sequence alignment algorithms. Bioinformatics. 1998;14(1):25-39.
[No Author Listed], Chapter 2: Polymerizer Module from Polymer. 1997. 14 pages.
Ainsleigh et al., Hidden Gauss-Markov Models for Signal Classification. IEEE Trans Sig Proc. Jun. 2002;50(6):1355-1367.
Churbanov et al., Duration learning for analysis of nanopore ionic current blockades. BMC Bioinformatics. Nov. 1, 2007;8 Suppl 7(Suppl 7):S14. doi: 10.1186/1471-2105-8-S7-S14.

(56) References Cited

OTHER PUBLICATIONS

Pylkkönen et al., Duration Modeling Techniques for Continuous Speech Recognition. Eighth International Conference on Spoken Language Processing. 2004. 4 pages.

R Development Core Team, R: A Language and Environment for Statistical Computing. R Foundation for Statistical Computing. Vienna, Austria. 2011. 3079 pages.

Cabello-Aguilar et al., Experimental and simulation studies of unusual current blockade induced by translocation of small oxidized PEG through a single nanopore. Phys Chem Chem Phys. Sep. 7, 2014;16(33):17883-92. doi: 10.1039/c4cp01954g.

Chu et al., Real-time monitoring of DNA polymerase function and stepwise single-nucleotide DNA strand translocation through a protein nanopore. Angew Chem Int Ed Engl. Dec. 27, 2010;49(52):10106-9. doi: 10.1002/anie.201005460.

Fennouri et al., Single molecule detection of glycosaminoglycan hyaluronic acid oligosaccharides and depolymerization enzyme activity using a protein nanopore. ACS Nano. Nov. 27, 2012;6(11):9672-8. doi: 10.1021/nn3031047. Epub Oct. 17, 2012.

Branton et al., The potential and challenges of nanopore sequencing. Nat Biotechnol. Oct. 2008;26(10):1146-53. doi: 10.1038/nbt.1495.

Hornblower et al., Single-molecule analysis of DNA-protein complexes using nanopores. Nat Methods. Apr. 2007;4(4):315-7. doi: 10.1038/nmeth1021. Epub Mar. 4, 2007.

Howorka et al., Nanopore analytics: sensing of single molecules. Chem Soc Rev. Aug. 2009;38(8):2360-84. doi: 10.1039/b813796j. Epub Jun. 1, 20095.

Panwar et al., Enzyme-modulated DNA translocation through a nanopore. J Am Chem Soc. Dec. 30, 2009;131(51):18563-70. doi: 10.1021/ja904047q.

\* cited by examiner

Time (s)

Fig. 38

Reference: GCTACTGCAAAGGATATTTCTAAATGTCGTCACTGATGCTGCTTCGTGTGGTTGATATTTTTCATGGTATTGATAAAGCTGTTGCCGATACTTGGAACA
Calls:     *#####* *#############* * *############* *##* *##
           CATACTGCCCGAGATATTTCTAAATGTCGTCAATTATGCTGCTTCGTGGTTCCTGGTATTCCTCAGGCTGTTGCCGAATATTGAGACA

Fig. 39

Sense
Reference: GCTACTGCAAAGGATATTTCTAAATGTCGTCACTGATGCTGCTTCGTGTGGTTGATATTTTTCATGGTATTGATAAAGCTGTTGCCGATACTTGGAACA
Calls:     *#####* *#############* * *############* *##* *##
           CATACTGCCCGAGATATTTCTAAATGTCGTCAATTATGCTGCTTCGTGGTTCCTATTTTCCTCAGGCTGTTGCCGAATATTGAGACA AntiSense (Reversed)
Reference: CGATGACGTTCCTATAAAGATTACGACCAGTGACTACCACGAAGACCACACCAACTATAAAAGTACCATAACTATTTCGACAACGCTATGAACCTTGT
Calls:     * *###* * *### * *### * *### * *### *## *###
           ACAAAGCGTTTAGTCAAAGGGTCCGAAATGATTCAGAAGAAAGAAAACTCCAGGGCAACCAAATAATTTCCGGCACGCACATAAAAAATTTGT ↓ More than the Sum of the Parts Sense-AntiSense
Reference: GCTACTGCAAAGGATATTTCTAAATGTCGTCACTGATGCTGCTTCGTGTGGTTGATATTTTTCATGGTATTGATAAAGCTGTTGCCGATACTTGGAACA
Calls:     *##############################* *###############* *#####
           GCTACTGCAAAGGATATTTCTAAATGTCGTCAGTGATGCTGCTTCGTGTGGTTGATATTTTTCATGGTATTGATAAAGCTGTTGCCGATACTTGGAACA

SEQUENCE LISTING

<160> NUMBER OF SEQ ID NOS: 84

<210> SEQ ID NO 1
<211> LENGTH: 558
<212> TYPE: DNA
<213> ORGANISM: Artificial Sequence
<220> FEATURE:
<223> OTHER INFORMATION: Synthetic Polynucleotide

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80
```

```
Ser Tyr Thr Thr Pro Asn Ile Leu Ile Asn Asn Gly Asn Ile Thr Ala
            85                  90                  95

Pro Pro Phe Gly Leu Asn Ser Val Ile Thr Pro Asn Leu Phe Pro Gly
        100                 105                 110

Val Ser Ile Ser Ala Arg Leu Gly Asn Gly Pro Gly Ile Gln Glu Val
            115                 120                 125

Ala Thr Phe Ser Val Arg Val Ser Gly Ala Lys Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 558
<212> TYPE: DNA
<213> ORGANISM: Artificial Sequence
<220> FEATURE:
<223> OTHER INFORMATION: Synthetic Polynucleotide

<400> SEQUENCE: 3

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattaacatc aacaatggta acattaccgc accgccgttt     300
ggcctgaaca gcgtgattac gccgaacctg tttccgggtg ttagcatctc tgcccgtctg     360
ggcaatggtc cgggcattca gaagtggca accттттagтg tgcgcgttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 4
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 4

```
Gly Leu Asp Asn Glu Leu Ser Leu Val Asp Gly Gln Asp Arg Thr Leu
1               5                  10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Asn Ile Asn Asn Gly Asn Ile Thr Ala
            85                  90                  95
```

```
Pro Pro Phe Gly Leu Asn Ser Val Ile Thr Pro Asn Leu Phe Pro Gly
                100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
                180

<210> SEQ ID NO 5
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 5
ataagaacat tatgatcagt aggagcacta cgacctttgt tctggtgctc gtccgggcgc    60
ccaaat                                                              66

<210> SEQ ID NO 6
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 6
ctctctctct cctctctctc aaataagaac attatgatca gtagg                   45

<210> SEQ ID NO 7
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 7
ctctctctct cctctctctc aataagaaca ttatgatcag tagga                   45

<210> SEQ ID NO 8
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 8
ctctctctct cctctctctc ataagaacat tatgatcagt aggag                   45

<210> SEQ ID NO 9
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 9
ctctctctct cctctctctc taagaacatt atgatcagta ggagc                   45
```

<210> SEQ ID NO 10
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 10
ctctctctct cctctctctc aagaacatta tgatcagtag gagca           45

<210> SEQ ID NO 11
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 11
ctctctctct cctctctctc agaacattat gatcagtagg agcac           45

<210> SEQ ID NO 12
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 12
ctctctctct cctctctctc gaacattatg atcagtagga gcact           45

<210> SEQ ID NO 13
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 13
ctctctctct cctctctctc aacattatga tcagtaggag cacta           45

<210> SEQ ID NO 14
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 14
ctctctctct cctctctctc acattatgat cagtaggagc actac           45

<210> SEQ ID NO 15
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 15
ctctctctct cctctctctc cattatgatc agtaggagca ctacg           45

<210> SEQ ID NO 16
<211> LENGTH: 45
<212> TYPE: DNA
<213> ORGANISM: Artificial Sequence
<220> FEATURE:

<223> OTHER INFORMATION: Synthetic Polynucleotide

<400> SEQUENCE: 16
ctctctctct cctctctctc attatgatca gtaggagcac tacga         45

<210> SEQ ID NO 17
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 17
ctctctctct cctctctctc ttatgatcag taggagcact acgac         45

<210> SEQ ID NO 18
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 18
ctctctctct cctctctctc tatgatcagt aggagcacta cgacc         45

<210> SEQ ID NO 19
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 19
ctctctctct cctctctctc atgatcagta ggagcactac gacct         45

<210> SEQ ID NO 20
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 20
ctctctctct cctctctctc tgatcagtag gagcactacg acctt         45

<210> SEQ ID NO 21
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 21
ctctctctct cctctctctc gatcagtagg agcactacga ccttt         45

<210> SEQ ID NO 22
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 22
ctctctctct cctctctctc atcagtagga gcactacgac ctttg         45

```
<210> SEQ ID NO 23
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 23
ctctctctct cctctctctc tcagtaggag cactacgacc tttgt            45

<210> SEQ ID NO 24
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 24
ctctctctct cctctctctc cagtaggagc actacgacct tgtt             45

<210> SEQ ID NO 25
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 25
ctctctctct cctctctctc agtaggagca ctacgacctt tgttc            45

<210> SEQ ID NO 26
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 26
ctctctctct cctctctctc gtaggagcac tacgaccttt gttct            45

<210> SEQ ID NO 27
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 27
tttttttttt tttttttttt taggagcact acgaccttttg ttctg           45

<210> SEQ ID NO 28
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 28
tttttttttt tttttttttt aggagcacta cgacctttgt tctgg            45

<210> SEQ ID NO 29
<211> LENGTH: 45
<212> TYPE: DNA
<213> ORGANISM: Artificial Sequence
<220> FEATURE:
<223> OTHER INFORMATION: Synthetic Polynucleotide
```

<400> SEQUENCE: 29
ctctctctct cctctctctc ggagcactac gacctttgtt ctggt    45

<210> SEQ ID NO 30
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 30
ctctctctct cctctctctc gagcactacg acctttgttc tggtg    45

<210> SEQ ID NO 31
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 31
ctctctctct cctctctctc agcactacga cctttgttct ggtgc    45

<210> SEQ ID NO 32
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 32
ctctctctct cctctctctc gcactacgac ctttgttctg gtgct    45

<210> SEQ ID NO 33
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 33
tttttttttt tttttttttt cactacgacc tttgttctgg tgctc    45

<210> SEQ ID NO 34
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 34
tttttttttt tttttttttt actacgacct tgttctggt gctcg    45

<210> SEQ ID NO 35
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 35
ctctctctct cctctctctc ctacgacctt tgttctggtg ctcgt    45

<210> SEQ ID NO 36
<211> LENGTH: 45

```
<212> TYPE: DNA
<213> ORGANISM: Artificial Sequence
<220> FEATURE:
<223> OTHER INFORMATION: Synthetic Polynucleotide

<400> SEQUENCE: 36
ctctctctct cctctctctc tacgaccttt gttctggtgc tcgtc            45

<210> SEQ ID NO 37
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 37
ctctctctct cctctctctc acgacctttg ttctggtgct cgtcc            45

<210> SEQ ID NO 38
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 38
ctctctctct cctctctctc cgacctttgt tctggtgctc gtccg            45

<210> SEQ ID NO 39
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 39
ctctctctct cctctctctc gacctttgtt ctggtgctcg tccgg            45

<210> SEQ ID NO 40
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 40
ctctctctct cctctctctc acctttgttc tggtgctcgt ccggg            45

<210> SEQ ID NO 41
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 41
ctctctctct cctctctctc cctttgttct ggtgctcgtc cgggc            45

<210> SEQ ID NO 42
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 42
```
ctctctctct cctctctctc ctttgttctg gtgctcgtcc gggcg         45

<210> SEQ ID NO 43
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 43
ctctctctct cctctctctc tttgttctgg tgctcgtccg ggcgc         45

<210> SEQ ID NO 44
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 44
ctctctctct cctctctctc ttgttctggt gctcgtccgg gcgcc         45

<210> SEQ ID NO 45
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 45
ctctctctct cctctctctc tgttctggtg ctcgtccggg cgccc         45

<210> SEQ ID NO 46
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 46
ctctctctct cctctctctc gttctggtgc tcgtccgggc gccca         45

<210> SEQ ID NO 47
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 47
ctctctctct cctctctctc ttctggtgct cgtccgggcg cccaa         45

<210> SEQ ID NO 48
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 48
ctctctctct cctctctctc tctggtgctc gtccgggcgc ccaaa         45

<210> SEQ ID NO 49
<211> LENGTH: 45
<212> TYPE: DNA
<213> ORGANISM: Artificial Sequence

```
<220> FEATURE:
<223> OTHER INFORMATION: Synthetic Polynucleotide

<400> SEQUENCE: 49
ctctctctct cctctctctc ctggtgctcg tccgggcgcc caaat           45

<210> SEQ ID NO 50
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 50
ctctctctct cctctctctc tggtgctcgt ccgggcgccc aaata           45

<210> SEQ ID NO 51
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 51
ctctctctct cctctctctc ggtgctcgtc cgggcgccca aataa           45

<210> SEQ ID NO 52
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 52
ctctctctct cctctctctc gtgctcgtcc gggcgcccaa ataag           45

<210> SEQ ID NO 53
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 53
ctctctctct cctctctctc tgctcgtccg ggcgcccaaa taaga           45

<210> SEQ ID NO 54
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 54
ctctctctct cctctctctc gctcgtccgg gcgcccaaat aagaa           45

<210> SEQ ID NO 55
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 55
ctctctctct cctctctctc ctcgtccggg cgcccaaata agaac           45
```

<210> SEQ ID NO 56
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 56
ctctctctct cctctctctc tcgtccgggc gcccaaataa gaaca           45

<210> SEQ ID NO 57
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 57
ctctctctct cctctctctc cgtccgggcg cccaaataag aacat           45

<210> SEQ ID NO 58
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 58
ctctctctct cctctctctc gtccgggcgc ccaaataaga acatt           45

<210> SEQ ID NO 59
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 59
ctctctctct cctctctctc tccgggcgcc caaataagaa catta           45

<210> SEQ ID NO 60
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 60
ctctctctct cctctctctc ccgggcgccc aaataagaac attat           45

<210> SEQ ID NO 61
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 61
ctctctctct cctctctctc cgggcgccca aataagaaca ttatg           45

<210> SEQ ID NO 62
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 62
ctctctctct cctctctctc gggcgcccaa ataagaacat tatga            45

<210> SEQ ID NO 63
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 63
ctctctctct cctctctctc ggcgcccaaa taagaacatt atgat            45

<210> SEQ ID NO 64
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 64
ctctctctct cctctctctc gcgcccaaat aagaacatta tgatc            45

<210> SEQ ID NO 65
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 65
ctctctctct cctctctctc cgcccaaata agaacattat gatca            45

<210> SEQ ID NO 66
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 66
ctctctctct cctctctctc gcccaaataa gaacattatg atcag            45

<210> SEQ ID NO 67
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 67
ctctctctct cctctctctc cccaaataag aacattatga tcagt            45

<210> SEQ ID NO 68
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 68
ctctctctct cctctctctc ccaaataaga acattatgat cagta            45

<210> SEQ ID NO 69

<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 69
ctctctctct cctctctctc caaataagaa cattatgatc agtag                45

<210> SEQ ID NO 70
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 70
tttttttttt tttttttttt tttttttttt tttttttttt ttttt                45

<210> SEQ ID NO 71
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 71
ctctctctct cctctctctc gacgagcacc agaacaaagg tcgta                45

<210> SEQ ID NO 72
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 72
tttttttttt tttttttttt gcccggacga gcaccagaac aaagg                45

<210> SEQ ID NO 73
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 73
ctctctctct cctctctctc gggcgcccgg acgagcacca gaaca                45

<210> SEQ ID NO 74
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 74
ctctctctct cctctctctc tttgggcgcc cggacgagca ccaga                45

<210> SEQ ID NO 75
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 75

```
ctctctctct cctctctctc gctcctactg atcataatgt tctta        45
```

<210> SEQ ID NO 76
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 76

```
ctctctctct cctctctctc tgctcctact gatcataatg ttctt        45
```

<210> SEQ ID NO 77
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 77

```
tttttttttt tttttttttt tccccccccc ccccaaataa gaacattatg atcagtagga     60
gcactacgac ctttgttctg gtgctcgtcc gggcgcccaa agtggagcga gtgcgagagg    120
cgagcggtca a                                                         131
```

<210> SEQ ID NO 78
<211> LENGTH: 112
<212> TYPE: DNA
<213> ORGANISM: Artificial Sequence
<220> FEATURE:
<223> OTHER INFORMATION: Synthetic Polynucleotide

<400> SEQUENCE: 78

```
gtatctccat cgctgttgac cgctcgcctc tcgcactcgc tccactttgg gcgcccggac     60
gagcaccaga acaaaggtcg tagtgctcct actgatcata atgttcttat tt            112
```

<210> SEQ ID NO 79
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 79

```
cagcgatgga gatac                                         15
```

<210> SEQ ID NO 80
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 80

```
gctactgcaa aggatatttc taatgtcgtc actgatgctg cttctggtgt ggttgatatt     60
tttcatggta ttgataaagc tgttgccgat acttggaaca                          100
```

<210> SEQ ID NO 81
<211> LENGTH: 100
<212> TYPE: DNA
<213> ORGANISM: Artificial Sequence
<220> FEATURE:
<223> OTHER INFORMATION: Synthetic Polynucleotide

```
<400> SEQUENCE: 81
catactgccc gagatatttc taatgtcgtc aattatgctg cttctggtgt ggttcctatt      60
tttcctggta ttcctcaggc tgttgccgaa tattgagaca                          100

<210> SEQ ID NO 82
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 82
acaaggttca tagccgttgt cgaaatagtt atggtacttt ttatagttgg tgtggtcttc      60
gtcgtagtca ctgctgtaat ctttatagga aacgtcatcg                          100

<210> SEQ ID NO 83
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 83
acaaattttt tatgcgtgcc ggaaattatt tgggttgccc ctggagtttg ggttttcttt      60
cttctgaatc attccggacc cttttgacta aacgctttgt                          100

<210> SEQ ID NO 84
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 84
cgatgacgtt tcctataaag attacagcag tcactacgac gaagaccaca ccaactataa      60
aaagtaccat aactatttcg acaacggcta tgaaccttgt                          100
```

METHOD OF OPERATING A MEASUREMENT SYSTEM TO ANALYZE A POLYMER

RELATED APPLICATIONS

This application is a continuation which claims the benefit under 35 U.S.C. § 120 of U.S. application Ser. No. 15/487,329, filed Apr. 13, 2017, entitled "ANALYSIS OF A POLYMER COMPRISING POLYMER UNITS", which is a continuation which claims the benefit under 35 U.S.C. § 120 of U.S. application Ser. No. 14/346,549, filed Mar. 21, 2014, entitled "ANALYSIS OF A POLYMER COMPRISING POLYMER UNITS", now abandoned, which is a 35 U.S.C. 371 national stage filing of International Application PCT/GB2012/052343, filed Sep. 21, 2012, entitled "ANALYSIS OF A POLYMER COMPRISING POLYMER UNITS", which claims priority to U.S. Provisional Patent Application 61/538,721, filed Sep. 23, 2011 entitled "ANALYSIS OF A POLYMER COMPRISING POLYMER UNITS", and U.S. Provisional Patent Application 61/617,880 filed on Mar. 30, 2012, entitled "ANALYSIS OF A POLYMER COMPRISING POLYMER UNITS". The contents of the aforementioned applications are hereby incorporated by reference in their entirety.

The present invention relates generally to the field of analysing a polymer comprising polymer units, for example but without limitation a polynucleotide, by making measurements related to the polymer. The first aspect of the present invention relates specifically to the estimation of a sequence of polymer units in the polymer. The second and third aspects of the present invention relate to the measurement of ion current flowing through a nanopore during translocation of a polymer for analysis of the polymer.

There are many types of measurement system that provide measurements of a polymer for the purpose of analysing the polymer and/or determining the sequence of polymer units.

For example but without limitation, one type of measurement system utilises a nanopore through which the polymer is translocated. Some property of the system depends on the polymer units in the nanopore, and measurements of that property are taken. For example, a measurement system may be created by placing a nanopore in an insulating membrane and measuring voltage-driven ionic transport through the nanopore in the presence of analyte molecules. Depending on the nature of the nanopore, the identity of an analyte may be revealed through its distinctive ion current signature, notably the duration and extent of current block and the variance of current levels. Such types of measurement system using a nanopore has considerable promise, particularly in the field of sequencing a polynucleotide such as DNA or RNA, and has been the subject of much recent development.

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required.

The present invention relates to a situation where the value of each measurement is dependent on a group of k polymer units where k is a positive integer (i.e a 'k-mer').

Furthermore, it is typical of many types of measurement system, including the majority of currently known biological nanopores, for the value of each measurement to be dependent on a k-mer where k is a plural integer. This is because more than one polymer unit contributes to the observed signal and might be thought of conceptually as the measurement system having a "blunt reader head" that is bigger than the polymer unit being measured. In such a situation, the number of different k-mers to be resolved increases to the power of k. For example, if there are n possible polymer units, the number of different k-mers to be resolved is $n^k$. While it is desirable to have clear separation between measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polymer, for example an estimate of the underlying sequence of polymer units.

Accordingly, much of the development work has been directed towards the design of a measurement system that improves the resolution of measurements. This is difficult in practical measurement systems, due to variation in measurements that can arise to varying extents from inherent variation in the underlying physical or biological system and/or measurement noise that is inevitable due the small magnitude of the properties being measured.

Much research has aimed at design of a measurement system that provides resolvable measurements that are dependent on a single polymer unit. However, this has proved difficult in practice.

Other work has accepted measurements that are dependent on k-mers where k is a plural integer, but has aimed at design of a measurement system in which the measurements from different k-mers are resolvable from each other. However practical limitations mean again that this is very difficult. Distributions of signals produced by some different k-mers can often overlap.

In principle, it might be possible to combine information from k measurements, where k is a plural integer, that each depend in part on the same polymer unit to obtain a single value that is resolved at the level of a polymer unit. However, this is difficult in practice. Firstly, this relies on the possibility of identifying a suitable transform to transform a set of k measurements. However, for many measurements systems, due to the complexity of the interactions in the underlying physical or biological system, such a transform either does not exist or is impractical to identify. Secondly, even if such a transform might exist in principle for a given measurement system, the variation in measurements makes the transform difficult to identify and/or the transform in might still provide values that cannot be resolved from each other. Thirdly, with such techniques it is difficult or impossible to take account of missed measurements, that is where a measurement that is dependent on a given k-mer is missing in the sequence of polymer units, as can sometimes be the case in a practical measurement system, for example due to the measurement system failing to take the measurement or due to an error in the subsequent data processing.

The first aspect of the present invention is concerned with the provision of techniques that improve the accuracy of estimating a sequence of polymer units in a polymer from such measurements that are dependent on a k-mer.

According to the first aspect of the present invention, there is provided a method of estimating a sequence of polymer units in a polymer from at least one series of measurements related to the polymer, wherein the value of each measurement is dependent on a k-mer, a k-mer being a group of k polymer units where k is a positive integer, the method comprising:

provided a model comprising, for a set of possible k-mers:
transition weightings representing the chances of transitions from origin k-mers to destination k-mers; and
emission weightings in respect of each k-mer that represent the chances of observing given values of measurements for that k-mer; and
analysing the series of measurements using an analytical technique that refers to the model and estimating at least one estimated sequence of polymer units in the polymer based on the likelihood predicted by the model of the series of measurements being produced by sequences of polymer units.

Further according to first aspect of the present invention, there is provided an analysis apparatus that implements a similar method.

Therefore, the first aspect of the present invention makes use of a model of the measurement system that produces the measurements. Given any series of measurements, the model represents the chances of different sequences of k-mers having produced those measurements. The first aspect of the present invention is particularly suitable for situations in which the value of each measurement is dependent on a k-mer, where k is a plural integer.

The model considers the possible k-mers. For example, in a polymer where each polymer unit may be one of 4 polymer units (or more generally n polymer units) there are $4^k$ possible k-mers (or more generally $n^k$ possible k-mers), unless any specific k-mer does not exist physically. For all k-mers that may exist, the emissions weightings take account of the chance of observing given values of measurements. The emission weightings in respect of each k-mer represent the chances of observing given values of measurements for that k-mer.

The transition weightings represent the chances of transitions from origin k-mers to destination k-mers, and therefore take account of the chance of the k-mer on which the measurements depend transitioning between different k-mers. The transition weightings may therefore take account of transitions that are more and less likely. By way of example, where k is a plural integer, for a given origin k-mer this may represent that a greater chance of a preferred k-mer transitions, being transitions to destination k-mers that have a sequence in which the first (k−1) polymer units are the final (k−1) polymer unit of the origin k-mer, than non-preferred transitions, being transitions to destination k-mers that have a sequence different from the origin k-mer and in which the first (k−1) polymer units are not the final (k−1) polymer units of the origin k-mer. For example, for 3-mers where the polymer units are naturally occurring DNA bases, state CGT has preferred transitions to GTC, GTG, GTT and GTA. By way of example without limitation, the model may be a Hidden Markov Model in which the transition weightings and emission weightings are probabilities.

This allows the series of measurements to be analysed using an analytical technique that refers to the model. At least one estimated sequence of polymer units in the polymer is estimated based on the likelihood predicted by the model of the series of measurements being produced by sequences of polymer units. For example but without limitation, the analytical technique may be a probabilistic technique.

In particular, the measurements from individual k-mers are not required to be resolvable from each other, and it is not required that there is a transform from groups of k measurements that are dependent on the same polymer unit to a value in respect of that transform, i.e. the set of observed states is not required to be a function of a smaller number of parameters (although this is not excluded). Instead, the use of the model provides accurate estimation by taking plural measurements into account in the consideration of the likelihood predicted by the model of the series of measurements being produced by sequences of polymer units. Conceptually, the transition weightings may be viewed as allowing the model to take account, in the estimation of any given polymer unit, of at least the k measurements that are dependent in part on that polymer unit, and indeed also on measurements from greater distances in the sequence. The model may effectively take into account large numbers of measurements in the estimation of any given polymer unit, giving a result that may be more accurate.

Similarly, the use of such a model may allow the analytical technique to take account of missing measurements from a given k-mer and/or to take account of outliers in the measurement produced by a given k-mer. This may be accounted for in the transition weightings and/or emission weightings. For example, the transition weightings may represent non-zero chances of at least some of the non-preferred transitions and/or the emission weightings may represent non-zero chances of observing all possible measurements.

The second and third aspects of the present invention are concerned with the provision of techniques that assist the analysis of polymers using measurements of ion current flowing through a nanopore while the polymer is translocated through the nanopore.

According to the second aspect of the present invention, there is provided a method of analysing a polymer comprising polymer units, the method comprising:

during translocation of a polymer through a nanopore while a voltage is applied across the nanopore, making measurements that are dependent on the identity of k-mers in the nanopore, a k-mer being k polymer units of the polymer, where k is a positive integer, wherein the measurements comprise, in respect of individual k-mers, separate measurements made at different levels of said voltage applied across the nanopore; and
analysing the measurements at said different levels of said voltage to determine the identity of at least part of the polymer.

The method involves making measurements that are dependent on the identity of k-mers in the nanopore, a k-mer being k polymer units of the polymer, where k is a positive integer. In particular, the measurements comprise, in respect of individual k-mers, separate measurements made at different levels of said voltage applied across the nanopore. The present inventors have appreciated and demonstrated that such measurements at different levels of said voltage applied across the nanopore provide additional information, rather than being merely duplicative. For example, the measurements at different voltages allow resolution of different states. For example, some k-mers that cannot be resolved at a given voltage can be resolved at another voltage.

The third aspect of the present invention provides a method of making measurements made under the application of different levels of voltage across the nanopore, that may optionally be applied in the second aspect of the invention. In particular, according to the third aspect of the present invention, there is provided a method of making measurements of a polymer comprising polymer units, the method comprising:

performing a translocation of said polymer through a nanopore while a voltage is applied across the nanopore;

during said translocation of the polymer through the nanopore, applying different levels of said voltage in a cycle, and making measurements that are dependent on the identity of k-mers in the nanopore, a k-mer being k polymer units of the polymer, where k is a positive integer, the measurements comprising separate measurements in respect of individual k-mers at said different levels of said voltage in said cycle, the cycle having a cycle period shorter than states in which said measurements are dependent on said individual k-mers.

Thus the third aspect of the present invention provides the same advantages as the second aspect of the present invention, in particular that the measurements provide additional information, rather than being merely duplicative. The measurements at different voltages allow resolution of different states in a subsequent analysis of the measurements. For example, some states that cannot be resolved at a given voltage can be resolved at another voltage.

This is based on an innovation in which measurements at different voltages are acquired during a single translocation of a polymer through a nanopore. This is achieved by changing the level of said voltage in a cycle, selected so that the cycle period is shorter than the duration of states that are measured.

However, it is not essential to use this method within the second aspect of the invention. As an alternative, the ion current measurements at different magnitudes of the voltage may be made during different translocations of the polymer through the nanopore which may be translocations in the same direction, or may include translocations in opposite directions.

Thus, the methods of the second aspect and third aspect of the present invention can provide additional information that improves subsequent analysis of the measurements to derive information about the polymer. Some examples of the types of information that may be derived are as follows.

The analysis may be to derive the timings of transitions between states. In this case, the additional info, Illation provided by the measurements of each state at different potentials improves the accuracy. For example, in the case that a transition between two states cannot be resolved at one voltage, the transition may be identified by the change in the level of the ion current measurement at another voltage. This potentially allows identification of a transition that would not be apparent working only at one voltage or a determination with a higher degree of confidence that a transition did not in fact occur. This identification may be used in subsequent analysis of the measurements.

In general, carrying out measurements at the different voltage levels provides more information than may be obtained at one voltage level. For example in the measurement of ion flow through the nanopore, information that may be obtained from the measurements includes the current level and the signal variance (noise) for a particular state. For example for translocation of DNA through a nanopore, k-mers comprising the nucleotide base G tend to give rise to states having increased signal variance. It may be difficult to determine whether a transition in states has occurred, for example due to respective states having similar current levels or where one or both of the respective states have high signal variance. The current level and signal variance for a particular state may differ for different voltage levels and thus measurement at the different voltage levels may enable the determination of high variance states or increase the level of confidence in determining a state. Consequently, it may be easier to determine a transition between states at one voltage level compared to another voltage level.

The analysis may be to estimate the identity of the polymer or to estimate a sequence of polymer units in the polymer. In this case, the additional information provided by the measurements of each state at different potentials improves the accuracy of the estimation.

In the case of estimating a sequence of polymer units, the analysis may use a method in accordance with the first aspect of the present invention. Accordingly, the features of the first aspect of the present invention may be combined with the features of the second aspect and/or third aspect of the present invention, in any combination.

Further according to second and third aspects of the present invention, there is provided an analysis apparatus that implements a similar method.

To allow better understanding, embodiments of the present invention will now be described by way of non-limitative example with reference to the accompanying drawings, in which:

FIG. 38 shows an estimated sequence of estimated k-mers aligned with the actual sequence;

FIG. 39 shows separate estimated sequences of sense and antisense regions of a polymer together with an estimated sequence derived by treating measurements from the sense and antisense regions as arranged in two respective dimensions;

Figure 1:
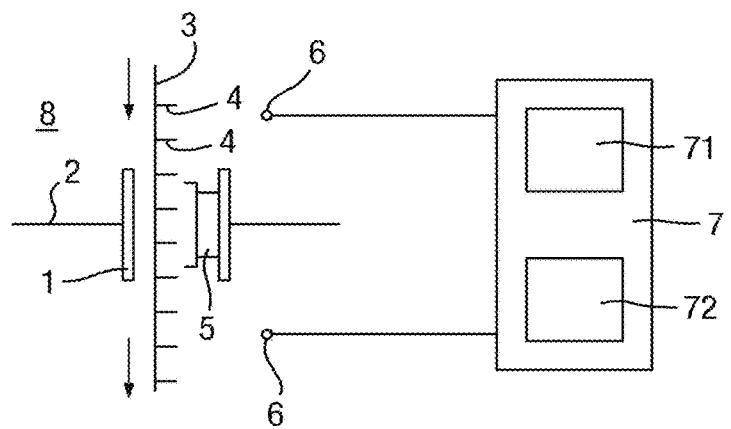
FIG. 1 is a schematic diagram of a measurement system comprising a nanopore.

The polymer may be a polynucleotide (or nucleic acid), a polypeptide such as a protein, a polysaccharide, or any other polymer. The polymer may be natural or synthetic.

In the case of a polynucleotide or nucleic acid, the polymer units may be nucleotides. The nucleic acid is typically deoxyribonucleic acid (DNA), ribonucleic acid (RNA), cDNA or a synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The nucleic acid may be single-stranded, be double-stranded or comprise both single-stranded and double-stranded regions. Typically cDNA, RNA, GNA, TNA or LNA are single stranded. The methods of the invention may be used to identify any nucleotide. The nucleotide can be naturally occurring or artificial. A nucleotide typically contains a nucleobase, a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

The nucleotide can be a damaged or epigenetic base. The nucleotide can be labelled or modified to act as a marker with a distinct signal. This technique can be used to identify the absence of a base, for example, an abasic unit or spacer in the polynucleotide. The method could also be applied to any type of polymer.

Of particular use when considering measurements of modified or damaged DNA (or similar systems) are the methods where complementary data are considered. The additional information provided allows distinction between a larger number of underlying states.

In the case of a polypeptide, the polymer units may be amino acids that are naturally occurring or synthetic.

In the case of a polysaccharide, the polymer units may be monosaccharides.

The present invention may be applied to measurements taken by a range of measurement systems, as discussed further below.

In accordance with all aspects of the present invention, the measurement system may be a nanopore system that comprises a nanopore. In this case, the measurements may be taken during translocation of the polymer through the nanopore. The translocation of the polymer through the nanopore generates a characteristic signal in the measured property that may be observed, and may be referred to overall as an "event".

The nanopore is a pore, typically having a size of the order of nanometres, that allows the passage of polymers therethrough. A property that depends on the polymer units translocating through the pore may be measured. The property may be associated with an interaction between the polymer and the pore. Interaction of the polymer may occur at a constricted region of the pore. The measurement system measures the property, producing a measurement that is dependent on the polymer units of the polymer.

The nanopore may be a biological pore or a solid state pore.

Where the nanopore is a biological pore, it may have the following properties.

The biological pore may be a transmembrane protein pore. Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is typically derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. The pore may also comprise one or more constructs that comprise two or more covalently attached monomers derived from Msp. Suitable pores are disclosed in U.S. Provisional Application No. 61/441,718 (filed 11 Feb. 2011). Preferably the pore is derived from MspA or a homolog or paralog thereof.

The biological pore may be a naturally occurring pore or may be a mutant pore. Typical pores are described in WO-2010/109197, Stoddart D et al., Proc Natl Acad Sci, 12; 106(19):7702-7, Stoddart D et al., Angew Chem Int Ed Engl. 2010; 49(3):556-9, Stoddart D et al., Nano Lett. 2010 Sep. 8; 10(9):3633-7, Butler T Z et al., Proc Natl Acad Sci 2008; 105(52):20647-52, and U.S. Provisional Application 61/441, 718.

The biological pore may be MS-(B1)8. The nucleotide sequence encoding B1 and the amino acid sequence of B1 are shown below (Seq ID: 1 and Seq ID: 2).

```
Seq ID 1:
MS-(B1)8 = MS-(D90N/D91N/D93N/D118R/D134R/E139K)8
ATGGGTCTGGATAATGAACTGAGCCTGGTGGACGGTCAAGATCGTACCCT

GACGGTGCAACAATGGGATACCTTTCTGAATGGCGTTTTTCCGCTGGATC

GTAATCGCCTGACCCGTGAATGGTTTCATTCCGGTCGCGCAAAATATATC

GTCGCAGGCCCGGGTGCTGACGAATTCGAAGGCACGCTGGAACTGGGTTA

TCAGATTGGCTTTCCGTGGTCACTGGGCGTTGGTATCAACTTCTCGTACA

CCACGCCGAATATTCTGATCAACAATGGTAACATTACCGCACCGCCGTTT

GGCCTGAACAGCGTGATTACGCCGAACCTGTTTCCGGGTGTTAGCATCTC

TGCCCGTCTGGGCAATGGTCCGGGCATTCAAGAAGTGGCAACCTTTAGTG

TGCGCGTTTCCGGCGCTAAAGGCGGTGTCGCGGTGTCTAACGCCCACGGT

ACCGTTACGGGCGCGGCCGGCGGTGTCCTGCTGCGTCCGTTCGCGCGCCT

GATTGCCTCTACCGGCGACAGCGTTACGACCTATGGCGAACCGTGGAATA

TGAACTAA

Seq ID 2:
MS-(B1)8 = MS-(D90N/D91N/D93N/D118R/D134R/E139K)8
GLDNELSLVDGQDRTLTVQQWDTFLNGVFPLDRNRLTREWFHSGRAKYIV

AGPGADEFEGTLELGYQIGFPWSLGVGINFSYTTPNILINNGNITAPPFG
```

```
LNSVITPNLFPGVSISARLGNGPGIQEVATFSVRVSGAKGGVAVSNAHGT

VTGAAGGVLLRPFARLIASTGDSVTTYGEPWNMN
```

The biological pore is more preferably MS-(B2)8. The amino acid sequence of B2 is identical to that of B1 except for the mutation L88N. The nucleotide sequence encoding B2 and the amino acid sequence of B2 are shown below (Seq ID: 3 and Seq ID: 4).

```
Seq ID 3:
MS-(B2)8 = MS-(L88N/D90N/D91N/D93N/D118R/D134R/E139K)8
ATGGGTCTGGATAATGAACTGAGCCTGGTGGACGGTCAAGATCGTACC

CTGACGGTGCAACAATGGGATACCTTTCTGAATGGCGTTTTTCCGCTG

GATCGTAATCGCCTGACCCGTGAATGGTTTCATTCCGGTCGCGCAAAA

TATATCGTCGCAGGCCCGGGTGCTGACGAATTCGAAGGCACGCTGGAA

CTGGGTTATCAGATTGGCTTTCCGTGGTCACTGGGCGTTGGTATCAAC

TTCTCGTACACCACGCCGAATATTAACATCAACAATGGTAACATTACC

GCACCGCCGTTTGGCCTGAACAGCGTGATTACGCCGAACCTGTTTCCG

GGTGTTAGCATCTCTGCCCGTCTGGGCAATGGTCCGGGCATTCAAGAA

GTGGCAACCTTTAGTGTGCGCGTTTCCGGCGCTAAAGGCGGTGTCGCG

GTGTCTAACGCCCACGGTACCGTTACGGGCGCGGCCGGCGGTGTCCTG

CTGCGTCCGTTCGCGCGCCTGATTGCCTCTACCGGCGACAGCGTTACG

ACCTATGGCGAACCGTGGAATATGAACTAA

Seq ID 4:
MS-(B2)8 = MS-(L88N/D90N/D91N/D93N/D118R/D134R/E139K)8
GLDNELSLVDGQDRTLTVQQWDTFLNGVFPLDRNRLTREWFHSGRAKY

IVAGPGADEFEGTLELGYQIGFPWSLGVGINFSYTTPNININNGNITA

PPFGLNSVITPNLFPGVSISARLGNGPGIQEVATFSVRVSGAKGGVAV

SNAHGTVTGAAGGVLLRPFARLIASTGDSVTTYGEPWNMN
```

The biological pore may be inserted into an amphiphilic layer such as a biological membrane, for example a lipid bilayer. An amphiphilic layer is a layer formed from amphiphilic molecules, such as phospholipids, which have both hydrophilic and lipophilic properties. The amphiphilic layer may be a monolayer or a bilayer. The amphiphilic layer may be a co-block polymer such as disclosed by (Gonzalez-Perez et al., Langmuir, 2009, 25, 10447-10450). Alternatively, a biological pore may be inserted into a solid state layer.

Alternatively, a nanopore may be a solid state pore comprising an aperture formed in a solid state layer.

A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as Si3N4, Al2O3, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO 2009/035647 and WO-2011/046706.

A solid state pore is typically an aperture in a solid state layer. The aperture may be modified, chemically, or otherwise, to enhance its properties as a nanopore. A solid state pore may be used in combination with additional components which provide an alternative or additional measurement of the polymer such as tunnelling electrodes (Ivanov A P et al., Nano Lett. 2011 Jan. 12; 11(1):279-85), or a field effect transistor (FET) device (International Application WO 2005/124888). Solid state pores may be formed by known processes including for example those described in WO 00/79257.

In one type of measurement system, there may be used measurements of the ion current flowing through a nanopore. These and other electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In order to allow measurements to be taken as the polymer translocates through a nanopore, the rate of translocation can be controlled by a polymer binding moiety. Typically the moiety can move the polymer through the nanopore with or against an applied field. The moiety can be a molecular motor using for example, in the case where the moiety is an enzyme, enzymatic activity, or as a molecular brake. Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, moieties that interact with that polymer type can be used. The polymer interacting moiety may be any disclosed in International Application No. PCT/GB10/000133 or U.S. 61/441,718, (Lieberman K R et al, J Am Chem Soc. 2010; 132(50):17961-72), and for voltage gated schemes (Lunn B et al., Phys Rev Lett. 2010; 104(23): 238103).

The polymer binding moiety can be used in a number of ways to control the polymer motion. The moiety can move the polymer through the nanopore with or against the applied field. The moiety can be used as a molecular motor using for example, in the case where the moiety is an enzyme, enzymatic activity, or as a molecular brake. The translocation of the polymer may be controlled by a molecular ratchet that controls the movement of the polymer through the pore. The molecular ratchet may be a polymer binding protein. For polynucleotides, the polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme may be derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 8), exonuclease III enzyme from *E. coli* (SEQ ID NO: 10), RecJ from *T. thermophilus* (SEQ ID NO: 12) and bacteriophage lambda exonuclease (SEQ ID NO: 14) and variants thereof. Three subunits comprising the sequence shown in SEQ ID NO: 14 or a variant thereof interact to form a trimer exonuclease. The enzyme is preferably derived from a Phi29 DNA polymerase. An enzyme derived from Phi29 polymerase comprises the sequence shown in SEQ ID NO: 6 or a variant thereof.

A variant of SEQ ID NOs: 6, 8, 10, 12 or 14 is an enzyme that has an amino acid sequence which varies from that of SEQ ID NO: 6, 8, 10, 12 or 14 and which retains polynucleotide binding ability. The variant may include modifications that facilitate binding of the polynucleotide and/or facilitate its activity at high salt concentrations and/or room temperature.

Over the entire length of the amino acid sequence of SEQ ID NO: 6, 8, 10, 12 or 14, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 6, 8, 10, 12 or 14 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to SEQ ID NO: 2. The enzyme may be covalently attached to the pore as discussed above.

The two strategies for single strand DNA sequencing are the translocation of the DNA through the nanopore, both cis to trans and trans to cis, either with or against an applied potential. The most advantageous mechanism for strand sequencing is the controlled translocation of single strand DNA through the nanopore under an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as molecular brake slowing down the movement of a polynucleotide through the pore. Any moieties, techniques or enzymes described in Provisional Application U.S. 61/441,718 or U.S. Provisional Application No. 61/402,903 could be used to control polymer motion.

However, alternative types of measurement system and measurements are also possible.

Some non-limiting examples of alternative types of measurement system are as follows.

The measurement system may be a scanning probe microscope. The scanning probe microscope may be an atomic force microscope (AFM), a scanning tunnelling microscope (STM) or another form of scanning microscope.

In the case where the reader is an AFM, the resolution of the AFM tip may be less fine than the dimensions of an individual polymer unit. As such the measurement may be a function of multiple polymer units. The AFM tip may be functionalised to interact with the polymer units in an alternative manner to if it were not functionalised. The AFM may be operated in contact mode, non-contact mode, tapping mode or any other mode.

In the case where the reader is a STM the resolution of the measurement may be less fine than the dimensions of an individual polymer unit such that the measurement is a function of multiple polymer units. The STM may be operated conventionally or to make a spectroscopic measurement (STS) or in any other mode.

Some examples of alternative types of measurement include without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (for example as disclosed in Ivanov A P et al., Nano Lett. 2011 Jan. 12; 11(1):279-85), and FET measurements (for example as disclosed in International Application WO2005/124888). Optical measurements may be combined with electrical measurements (Soni G V et al., Rev Sci Instrum. 2010 January; 81(1):014301). The measurement may be a trans-membrane current measurement such as measurement of ion current flow through a nanopore. The ion current may typically be the DC ion current, although in principle an alternative is to use the AC current flow (i.e. the magnitude of the AC current flowing under application of an AC voltage).

Herein, the term 'k-mer' refers to a group of k-polymer units, where k is a positive integer, including the case that k is one, in which the k-mer is a single polymer unit. In some contexts, reference is made to k-mers where k is a plural integer, being a subset of k-mers in general excluding the case that k is one.

Although ideally the measurements would be dependent on a single polymer unit, with many typical measurement systems, the measurement is dependent on a k-mer of the polymer where k is a plural integer. That is, each measurement is dependent on the sequence of each of the polymer units in a k-mer where k is a plural integer. Typically the measurements are of a property that is associated with an interaction between the polymer and the measurement system.

In some embodiments of the present invention it is preferred to use measurements that are dependent on small groups of polymer units, for example doublets or triplets of polymer units (i.e. in which k=2 or k=3). In other embodiments, it is preferred to use measurements that are dependent on larger groups of polymer units, i.e. with a "broad" resolution. Such broad resolution may be particularly useful for examining homopolymer regions.

Especially where measurements are dependent on a k-mer where k is a plural integer, it is desirable that the measurements are resolvable (i.e. separated) for as many as possible of the possible k-mers. Typically this can be achieved if the measurements produced by different k-mers are well spread over the measurement range and/or have a narrow distribution. This may be achieved to varying extents by different measurement systems. However, it is a particular advantage of the present invention, that it is not essential for the measurements produced by different k-mers to be resolvable.

FIG. 1 schematically illustrates an example of a measurement system 8 comprising a nanopore that is a biological pore 1 inserted in a biological membrane 2 such as an amphiphilic layer. A polymer 3 comprising a series of polymer units 4 is translocated through the biological pore 1 as shown by the arrows. The polymer 3 may be a polynucleotide in which the polymer units 4 are nucleotides. The polymer 3 interacts with an active part 5 of the biological pore 1 causing an electrical property such as the trans-membrane current to vary in dependence on a k-mer inside the biological pore 1. In this example, the active part 5 is illustrated as interacting with a k-mer of three polymer units 4, but this is not limitative.

Electrodes 6 arranged on each side of the biological membrane 2 are connected to a an electrical circuit 7, including a control circuit 71 and a measurement circuit 72.

The control circuit 71 is arranged to supply a voltage to the electrodes 6 for application across the biological pore 1.

The measurement circuit 72 is arranged to measures the electrical property. Thus the measurements are dependent on the k-mer inside the biological pore 1.

Figure 2:
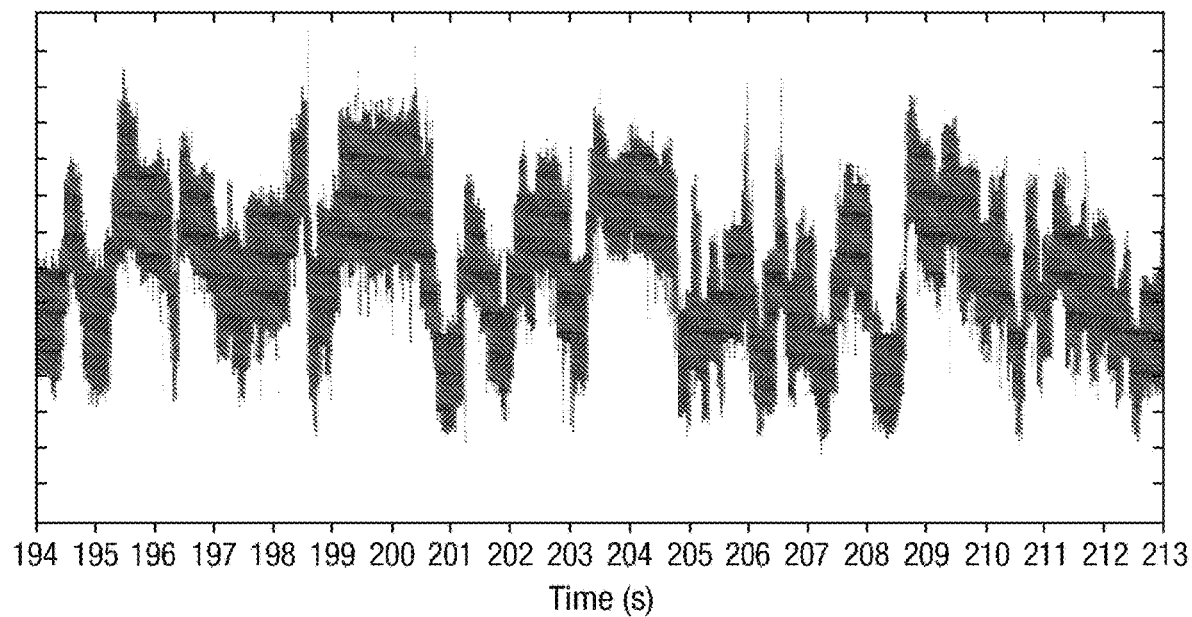
FIG. 2 is a plot of a signal of an event measured over time by a measurement system.

A typical type of signal output by a measurement system and which is an input signal to be analysed in accordance with the present invention is a "noisy step wave", although without limitation to this signal type. An example of an input signal having this form is shown in FIG. 2 for the case of an ion current measurement obtained using a measurement system comprising a nanopore.

This type of input signal comprises an input series of measurements in which successive groups of plural measurements are dependent on the same k-mer. The plural measurements in each group are of a constant value, subject to some variance discussed below, and therefore form a "level" in the signal, corresponding to a state of the measurement system. The signal moves between a set of levels, which may be a large set. Given the sampling rate of the instrumentation and the noise on the signal, the transitions between levels can be considered instantaneous, thus the signal can be approximated by an idealised step trace.

The measurements corresponding to each state are constant over the time scale of the event, but for most measurement systems will be subject to variance over a short time scale. Variance can result from measurement noise, for example arising from the electrical circuits and signal processing, notably from the amplifier in the particular case of electrophysiology. Such measurement noise is inevitable due the small magnitude of the properties being measured. Variance can also result from inherent variation or spread in the underlying physical or biological system of the measurement system. Most measurement systems will experience such inherent variation to greater or lesser extents. For any given measurement system, both sources of variation may contribute or one of these noise sources may be dominant.

In addition, typically there is no a priori knowledge of number of measurements in the group, which varies unpredictably.

These two factors of variance and lack of knowledge of the number of measurements can make it hard to distinguish some of the groups, for example where the group is short and/or the levels of the measurements of two successive groups are close to one another.

The signal takes this form as a result of the physical or biological processes occurring in the measurement system. Thus, each group of measurements may be referred to as a "state".

For example, in some measurement systems comprising a nanopore, the event consisting of translocation of the polymer through the nanopore may occur in a ratcheted manner During each step of the ratcheted movement, the ion current flowing through the nanopore at a given voltage across the nanopore is constant, subject to the variance discussed above. Thus, each group of measurements is associated with a step of the ratcheted movement. Each step corresponds to a state in which the polymer is in a respective position relative to the nanopore. Although there may be some variation in the precise position during the period of a state, there are large scale movements of the polymer between states. Depending on the nature of the measurement system, the states may occur as a result of a binding event in the nanopore.

The duration of individual states may be dependent upon a number of factors, such as the potential applied across the pore, the type of enzyme used to ratchet the polymer, whether the polymer is being pushed or pulled through the pore by the enzyme, pH, salt concentration and the type of nucleoside triphosphate present. The duration of a state may vary typically between 0.5 ms and 3 s, depending on the measurement system, and for any given nanopore system, having some random variation between states. The expected distribution of durations may be determined experimentally for any given measurement system.

The method may use plural input series of measurements each taking the form described above in which successive groups of plural measurements in each series arc dependent on the same k-mer. Such plural series might be registered so that it is known a priori which measurements from the respective series correspond and are dependent on the same k-mer, for example if the measurements of each series are taken at the same time. This might be the case, for example, if the measurements are of different properties measured by different measurement systems in synchronisation. Alternatively, such plural series might not be registered so that it is not known a priori which measurements from the respective series correspond and are dependent on the same k-mer. This might be the case, for example, if the series of measurements are taken at different times.

The method according to the third aspect discussed below in which measurements are made under the application of different levels of voltage across a nanopore, provides a series of measurements in respect of each level of voltage. In this case, the cycle period of the measurements is chosen having regard to the cycle period of the states for the measurement system in question. Ideally, the cycle period is shorter than the duration of all states, which is achieved by selecting a cycle period that is shorter than the minimum expected cycle period for the measurement system. However useful information may be obtained from measurements made during cycle periods that are shorter than the duration of only some states, for example shorter than the average, 60%, 70%, 80%, 90%, 95%, or 99% of the duration of states. Typically the cycle period may be at most 3 s, more typically at most 2 s or at most 1 s. Typically the cycle period may be at least 0.5 ms, more typically at least 1 ms or at least 2 ms.

More than one voltage cycle may be applied for the duration of a state, for example a number between 2 and 10.

Multiple measurements may be made at one voltage level (or multiple measurements in at each of plural voltage levels) in respect of each k-mer. In one possible approach, the different levels of voltage may each be applied continuously for a period of time, for example when the voltage waveform is a step wave, and during respective ones of the periods of time, a group of multiple measurements are made at the one of the voltages applied during that period.

The multiple measurements may themselves be used in the subsequent analysis. Alternatively, one or more summary measurements at the (or each) voltage level may be derived from each group of multiple measurements. The one or more summary measurements may be derived from the multiple measurements at any given voltage level in respect of any given k-mer in any manner, for example as an average or median, or as a measure of statistical variation, for example the standard deviation. The one or more summary measurements may then be used in the subsequent analysis.

The voltage cycle may be chosen from a number of different waveforms. The waveform may be asymmetric, symmetric, regular or irregular.

In one example of a cycle, the different levels of voltage may each be applied continuously for a period of time, i.e. for a partial period of the cycle, with a transition between those different levels, for example a square wave or stepped wave. The transitions between the voltage levels may be sharp or may be ramped over a period of time.

In another example of a cycle, the voltage level may vary continuously, for example being ramped between different levels, for example a triangular or sawtooth wave. In this case measurements at different levels may be made by making measurements at times within the cycle corresponding to the desired voltage level.

Information may be derived from measurement at a voltage plateau or from measurement of the slope. Further information may be derived in addition to measurements made at different voltage levels, for example by measurement of the shape of the transient between one voltage level and another.

In a stepped voltage scheme the transitions between voltage levels may be shaped such that any capacitive transients arc minimised. Considering the nanopore system as a simple RC circuit the current flowing, I, is given by the equation, $I=V/R+C\ dV/dt$, where V is the applied potential, R the resistance (typically of the pore), t time and C the capacitance (typically of the bilayer). In this model system the transition between two voltage levels would follow an exponential of time constant, $\tau=RC$ where $V=V2-(V2-V1)*\exp(-t/\tau)$.

Figure 52A:
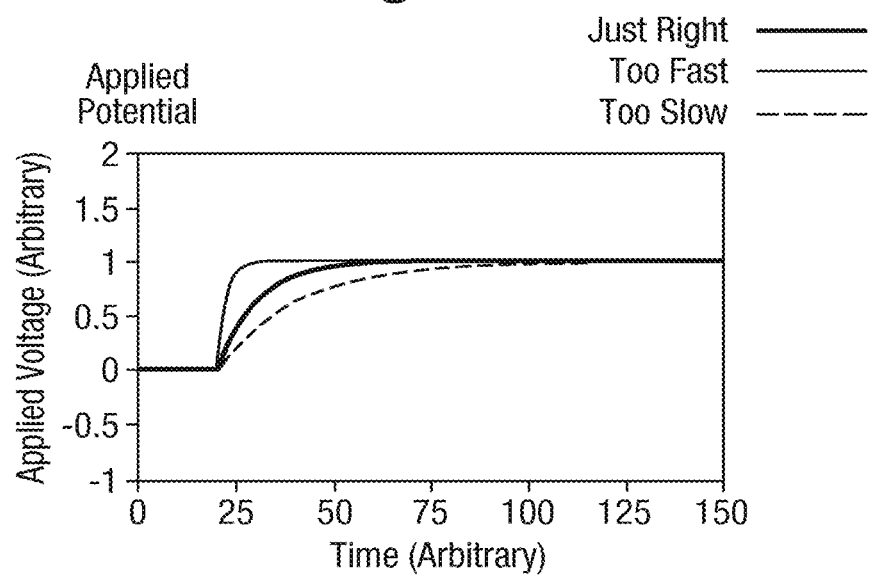
FIGS. 52a and 52b are plots over the same time scale of shaped voltage steps applied across a nanopore and the resultant current. All the aspects of the present invention may be applied to a range of polymers as follows.
Figure 52B:
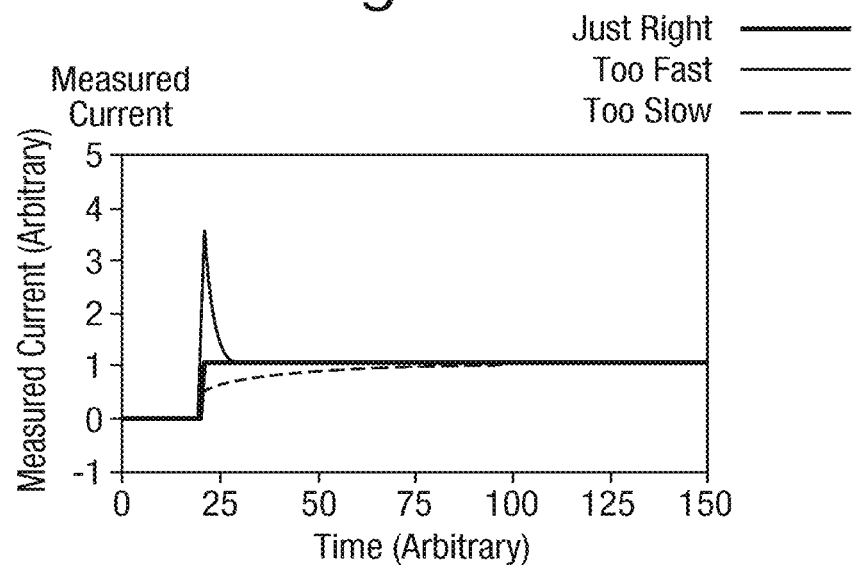

FIGS. 52a and 52b illustrates the cases where the time constant T of the transition between the voltage levels is chosen such that the transition speed is optimised, too fast and too slow. Where the voltage transition is too fast a spike (overshoot) is seen in the measured current signal, too slow and the measured signal does not flatten out quickly enough (undershoot). In the case where the transition speed is optimised the time where the measured current is distorted from the ideal sharp transition is minimised. The time constant T of the transition may be determined from measurement of the electrical properties of the measurement system, or from testing of different transitions.

Measurements may be made at any number of two or more levels of voltage. The levels of voltage are selected so that the measurements at each level of voltage provide information about the identities of the k-mers upon which the measurements depend. The choice of levels therefore depends on the nature of the measurement system. The extent of potential difference applied across the nanopore will depend upon factors such as the stability of the amphiphilic layer, the type of enzyme used and the desired speed of translocation. Typically each of the levels of voltage will be of the same polarity, although in general one or more of the levels of voltage could be of an opposite polarity to the others. In general, for most nanopore systems each level of voltage might typically be between 10 mV and 2V relative to ground. Thus the voltage difference between the voltage levels may typically be at least 10 mV, more preferably at least 20 mV. The voltage difference between the voltage levels may typically be at most 1.5V, more typically at most 400 mV. Greater voltage differences tend to give rise to greater differences in current between the voltage levels and therefore potentially a greater differentiation between respective states. However high voltage levels may give rise for example to more noise in the system or result in disruption of translocation by the enzyme. Conversely smaller voltage differences tend to give rise to smaller differences in current. An optimum potential difference may be chosen depending upon the experimental conditions or the type of enzyme ratchet.

A k-mer measured at one voltage level might not necessarily be the same k-mer as measured at a different voltage level. The value of k may differ between k-mers measured at different potentials. Should this be the case, it is likely however that there will be polymer units that are common to each k-mer measured at the different voltage levels. Without being bound by theory, it is thought that any differences in the k-mers being measured may be due to a change of conformation of the polymer within the nanopore at higher potential differences applied across the nanopore resulting in a change in the number of polymer units being measured by the reader head. The extent of this conformational change is likely to be dependent upon the difference in potential between one value and another.

There may be other information available either as part of the measurement or from additional sources that provides registration information. This other information may enable states to be identified.

Alternatively, the signal may take an arbitrary form. In these cases, the measurements corresponding to k-mers may also be described in terms of a set of emissions and transitions. For example, a measurement that is dependent on a particular k-mer may comprise of a series of measurements occurring in a fashion amenable to description by these methods.

The extent to which a given measurement system provides measurements that are dependent on k-mers and the size of the k-mers may be examined experimentally. For example, known polymers may be synthesized and held at predetermined locations relative to the measurement system to investigate from the resultant measurements how the measurements depend on the identity of k-mers that interact with the measurement system.

One possible approach is to use a set of polymers having identical sequences except for a k-mer at a predetermined position that varies for each polymer of the set. The size and identity of the k-mers can be varied to investigate the effect on the measurements.

Figure 3:
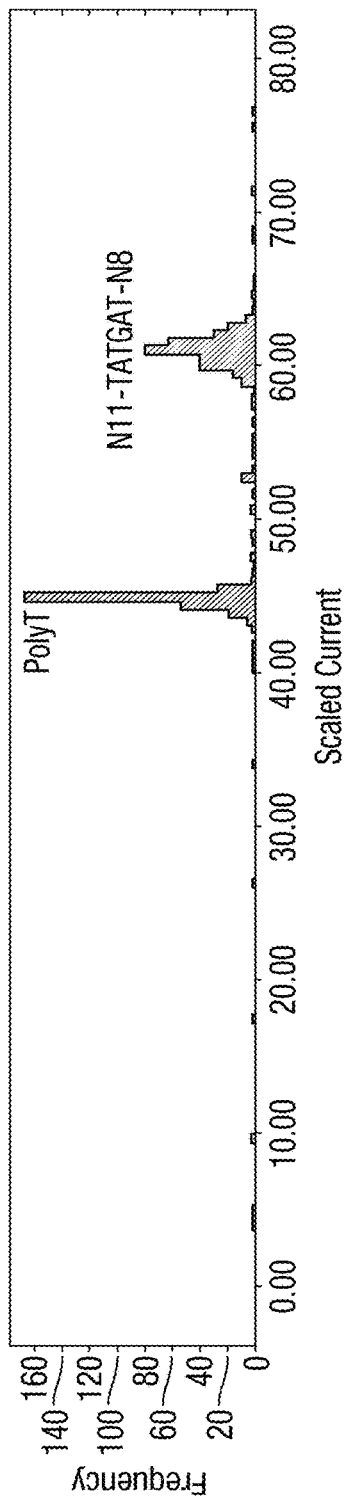
FIG. 3 is a graph of the frequency distributions of measurements of two different polynucleotides in a measurement system comprising a nanopore.

Another possible approach is to use a set of polymers in which the polymer units outside a k-mer under investigation at a predetermined position vary for each polymer of the set. As an example of such an approach, FIG. 3 is a frequency distribution of current measurements of two polynucleotides in a measurement system comprising a nanopore. In one of the polynucleotides (labelled polyT), every base in the region of the nanopore is a T (labelled polyT), and in the other of the polynucleotides (labelled N11-TATGAT-N8), 11 bases to the left and 8 to the right of a specific fixed 6-mer (having the sequence TATGAT) are allowed to vary. The example of FIG. 3 shows excellent separation of the two strands in terms of the current measurement. The range of values seen by the N11-TATGAT-N8 strand is also only slightly broader than that seen by the polyT. In this way and measuring polymers with other sequences also, it can be ascertained that, for the particular measurement system in question, measurements are dependent on 6-mers to a good approximation.

This approach, or similar, can be generalised for any measurement system enabling the location and a minimal k-mer description to be determined.

A probabilistic framework, in particular techniques applying multiple measurements under different conditions or via different detection methods, may enable a lower-k description of the polymer to be used. For example in the case of Sense and Antisense DNA measurements discussed below, a 3mer description may be sufficient to determine the underlying polymer k-mers where a more accurate description of each k-mer measurement would be a 6-mer. Similarity, in the case of measurement at multiple potentials, a k-mer description, wherein k has a lower value may be sufficient to determine the underlying polymer k-mers where a more accurate description of each k-mer measurement would be a kmer or k-mers wherein k has a higher value.

Similar methodology may be used to identify location and width of well-approximating k-mers in a general measurement system. In the example of FIG. 3, this is achieved by changing the position of the 6-mer relative to the pore (e.g. by varying the number of Ns before and after) to detect location of the best approximating k-mer and increasing and decreasing the number of fixed bases from 6. The value of k can be minimal subject to the spread of values being sufficiently narrow. The location of the k-mer can be chosen to minimise peak width.

For typical measurement systems, it is usually the case that measurements that are dependent on different k-mers are not all uniquely resolvable. For example, in the measurement system to which FIG. 3 relates, it is observed that the range of the measurements produced by DNA strands with a fixed 6-mer is of the order of 2 pA and the approximate measurement range of this system is between 30 pA and 70 pA. For a 6-mer, there are 4096 possible k-mers. Given that each of these has a similar variation of 2 pA, it is clear that in a 40 pA measurement range these signals will not be uniquely resolvable. Even where measurements of some k-mers are resolvable, it is typically observed that measurements of many other k-mers are not.

For many actual measurement systems, it is not possible to identify a function that transforms k measurements, that each depend in part on the same polymer unit, to obtain a single value that is resolved at the level of a polymer unit, or more generally the k-mer measurement is not describable by a set of parameters smaller than the number of k-mers.

Figure 4:
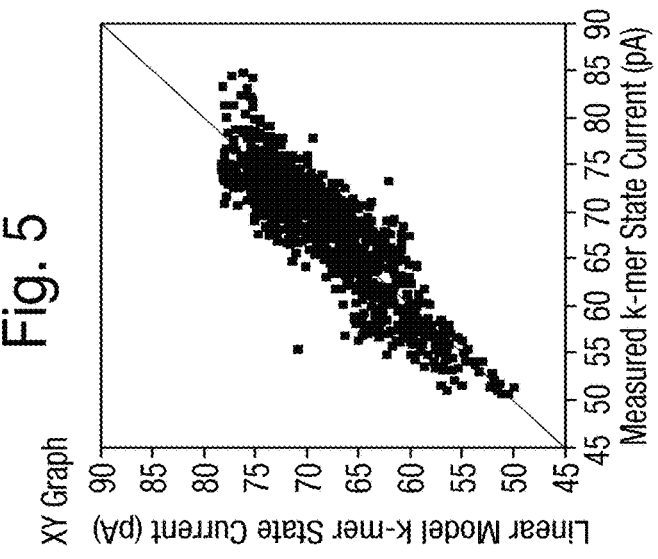
FIGS. 4 and 5 are plots of 64 3-mer coefficients and 1024 5-mer coefficients, respectively, against predicted values from a first order linear model applied to sets of experimentally derived current measurements.
Figure 5:
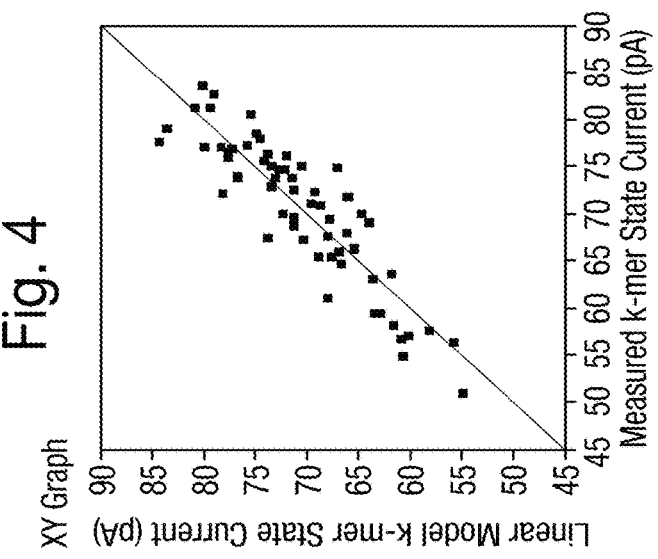

By way of example, it will now be demonstrated for a particular measurement system comprising a nanopore experimentally derived ion current measurements of polynucleotides are not accurately describable by a simple first order linear model. This is demonstrated for the two training sets described in more detail below. The simple first order linear model used for this demonstration is:

$$\text{Current}=\text{Sum}[fn(Bn)]+E$$

where fn are coefficients for each base Bn occurring at each position n in the measurement system and E represents the random error due to experimental variability. The data are fit to this model by a least squares method, although any one of many methods known in the art could alternatively be used. FIGS. 4 and 5 are plots of the best model fit against the current measurements. If the data was well described by this model, then the points should closely follow the diagonal line within a typical experimental error (for example 2 pA). This is not the case showing that the data is not well described by this linear model for either set of coefficients.

There will now be described a specific method of analysing an input signal that is a noisy step wave, that embodies the first aspect of the present invention. The following method relates to the case that measurements are dependent on a k-mer where k is two or more, but the same method may be applied in simplified form to measurements that are dependent on a k-mer where k is one.

Figure 6:
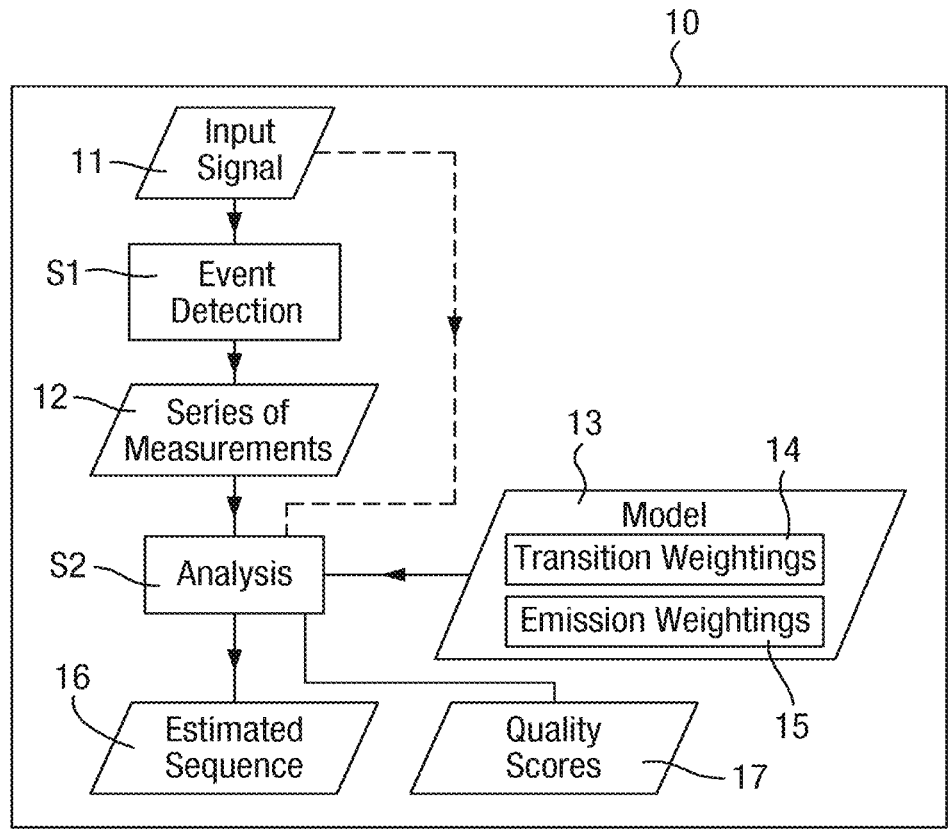
FIG. 6 is a flowchart of a method of analyzing an input signal comprising measurements of a polymer.

The method is illustrated in FIG. 6 and may be implemented in an analysis unit 10 illustrated schematically in FIG. 6. The analysis unit 10 receives and analyses an input signal that comprises measurements from the measurement circuit 72. The analysis unit 10 and the measurement system 8 are therefore connected and together constitute an apparatus for analysing a polymer. The analysis unit 10 may also provide control signals to the control circuit 7 to select the voltage applied across the biological pore 1 in the measurement system 8, and may analyse the measurements from the measurement circuit 72 in accordance with applied voltage.

The apparatus including the analysis unit 10 and the measurement system 8 may be arranged as disclosed in any of WO-2008/102210, WO-2009/07734, WO-2010/122293 and/or WO-2011/067559.

The analysis unit 10 may be implemented by a computer program executed in a computer apparatus or may be implemented by a dedicated hardware device, or any combination thereof. In either case, the data used by the method is stored in a memory in the analysis unit 10. The computer apparatus, where used, may be any type of computer system but is typically of conventional construction. The computer program may be written in any suitable programming language. The computer program may be stored on a computer-readable storage medium, which may be of any type, for example: a recording medium which is insertable into a drive of the computing system and which may store information magnetically, optically or opto-magnetically; a fixed recording medium of the computer system such as a hard drive; or a computer memory.

The method is performed on an input signal 11 that comprises a series of measurements (or more generally any number of series, as described further below) of the type described above comprising successive groups of plural measurements that are dependent on the same k-mer without a priori knowledge of number of measurements in any group. An example of such an input signal 11 is shown in FIG. 2 as previously described.

In a state detection step S1, the input signal 11 is processed to identify successive groups of measurements and to derive a series of measurements 12 consisting of a predetermined number, being one or more, of measurements in respect of each identified group. An analysis step S2 is performed on the thus derived series of measurements 12. The purpose of the state detection step S1 is to reduce the input signal to a predetermined number of measurements associated with each k-mer state to simplify the analysis step S2. For example a noisy step wave signal, as shown in FIG. 2 may be reduced to states where a single measurement associated with each state may be the mean current. This state may be termed a level.

Figure 7:
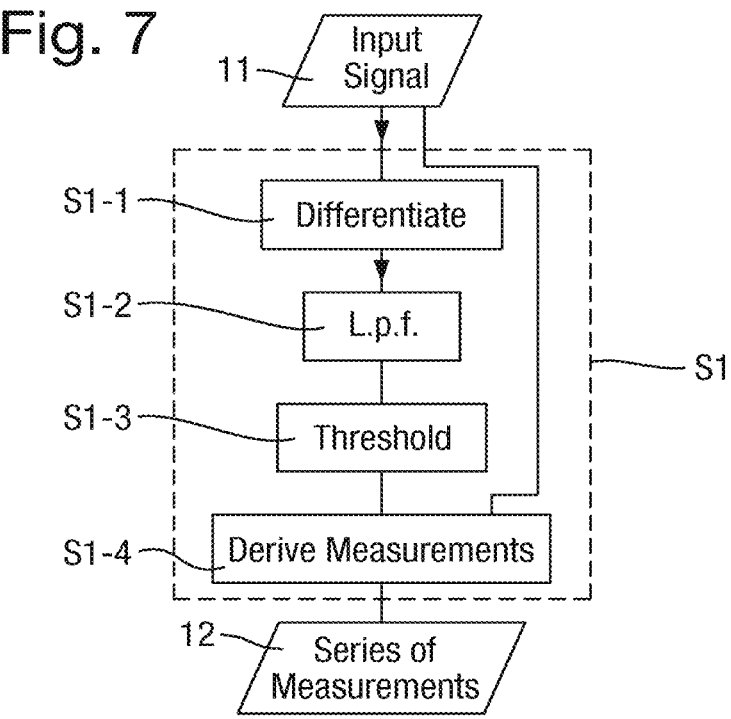
FIG. 7 is a flowchart of a state detection step of FIG. 6.

The state detection step S1 may be performed using the method shown in FIG. 7 that looks for short-term increases in the derivative of the input signal 11 as follows.

In step S1-1, the input signal 11 is differentiated to derive its derivative.

In step S1-2, the derivative from step S1-1 is subjected to low-pass filtering to suppress high-frequency noise (which the differentiation tends to amplify).

In step S1-3, the filtered derivative from step S1-2 is thresholded to detect transition points between the groups of measurements, and thereby identify the groups of data.

In step S1-4, a predetermined number of measurements is derived from the input signal 11 in each group identified in step S1-3. In the simplest approach, a single measurement is derived, for example as the mean, median, or other measure of location, of the measurements in each identified group. The measurements output from step S1-4 form the series of measurements 12. In other approaches, plural measurements in respect of each group are derived.

A common simplification of this technique is to use a sliding window analysis whereby one compares the means of two adjacent windows of data. A threshold can then be either put directly on the difference in mean, or can be set based on the variance of the data points in the two windows (for example, by calculating Student's t-statistic). A particular advantage of these methods is that they can be applied without imposing many assumptions on the data.

Other information associated with the measured levels can be stored for use later in the analysis. Such information may include without limitation any of: the variance of the signal; asymmetry information; the confidence of the observation; the length of the group.

Figure 9:
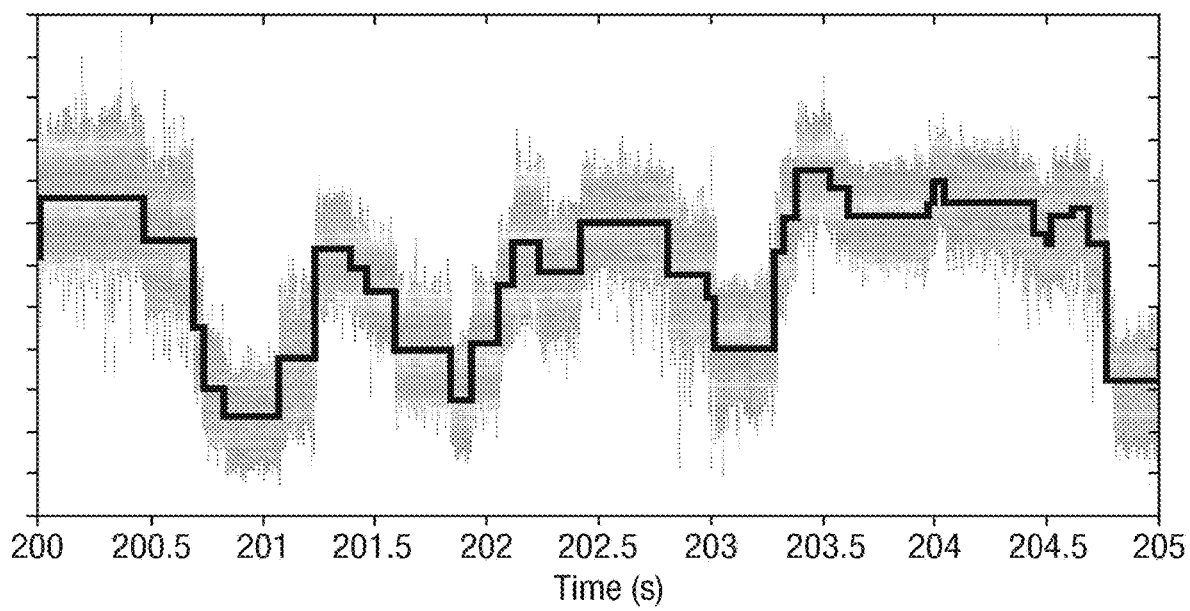
FIGS. 9 and 10 are plots, respectively, of an input signal subject to the state detection step and of the resultant series of measurements.
Figure 10:
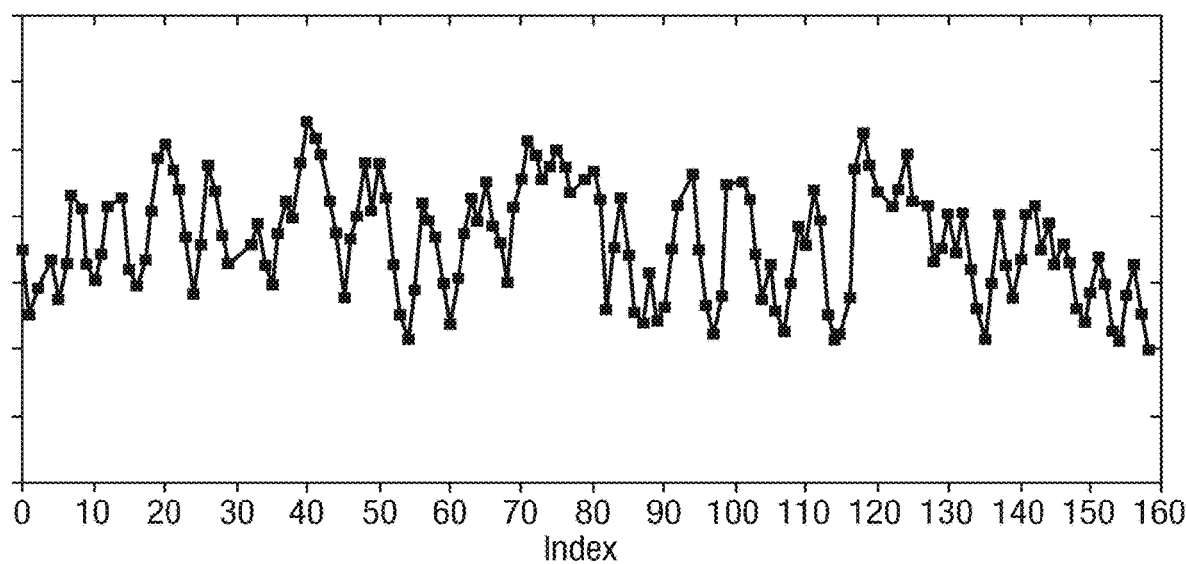

By way of example, FIG. 9 illustrates an experimentally determined input signal 11 reduced by a moving window t-test. In particular, FIG. 9 shows the input signal 11 as the light line. Levels following state detection are shown overlayed as the dark line. FIG. 10 shows the series of measurements 12 derived for the entire trace, calculating the level of each state from the mean value between transitions.

However, as described in more detail below, the state detection step S1 is optional and in an alternative described further below, may be omitted. In this case, as shown schematically by the dotted line in FIG. 6, the analysis step S2 is performed on the input signal 11 itself, instead of the series of measurements 12.

The analysis step S2 will now be described.

The analysis step S2 uses an analytical technique that refers to a model 13 stored in the analysis unit 10. The analysis step S2 estimates an estimated sequence 16 of polymer units in the polymer based on the likelihood predicted by the model 13 of the series of measurements 12 being produced by sequences of polymer units. In the simplest case, the estimated sequence 16 may be a representation that provides a single estimated identity for each polymer unit. More generally, the estimated sequence 16 may be any representation of the sequence of polymer units according to some optimality criterion. For example, the estimated sequence 16 may comprise plural sequences, for example including plural estimated identities of one or more polymer units in part or all of the polymer.

The mathematical basis of the model 13 will now be considered. The analysis step S2 also provides quality scores 17 that are described further below.

The relationship between a sequence of random variables $\{X_1, X_2, \ldots, X_n\}$ from which currents are sampled may be represented by a simple graphical model A, which represents the conditional independence relationships between variables:

$$X_1\text{-}X_2\text{-}X_3\text{-}\ldots\text{-}X_n$$

Each current measurement is dependent on a k-mer being read, so there is an underlying set of random variables $\{S_1, S_2, \ldots, S_n\}$ representing the underlying sequence of k-mers and with a corresponding graphical model B:

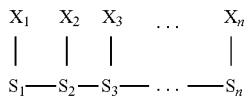

These models as applied to the current area of application take advantage of the Markov property. In model A, if $f(X_i)$ is taken to represent the probability density function of the random variable $X_i$, then the Markov property can be represented as:

$$f(X_m|X_{m-1}) = f(X_m|X_1, X_2, \ldots, X_{m-1})$$

In model B, the Markov property can be represented as:

$$P(S_m|S_{m-1}) = P(S_m|S_1, S_2, \ldots, S_{m-1})$$

Depending on exactly how the problem is encoded, natural methods for solution may include Bayesian networks, Markov random fields, Hidden Markov Models, and also including variants of these models, for example conditional or maximum entropy formulations of such models. Methods of solution within these slightly different frameworks are often similar. Generally, the model 13 comprises transition weightings 14 representing the chances of transitions from origin k-mers to destination k-mers; and emission weightings 15 in respect of each k-mer that represent the chances of observing given values of measurements for that k-mer. An explanation will now be given in the case that the model 13 is a Hidden Markov Model.

The Hidden Markov Model (HMM) is a natural representation in the setting given here in graphical model B. In a HMM, the relationship between the discrete random variables $S_m$ and $S_{m+1}$ is defined in terms of a transition matrix of transition weightings 14 that in this case are probabilities representing the probabilities of transitions between the possible states that each random variable can take, that is from origin k-mers to destination k-mers. For example, conventionally the (i,j)th entry of the transition matrix is a transition weighting 14 representing the probability that $S_{m+1} = s_{m+1,j}$, given that $S_m = s_{m,i}$, i.e. the probability of transitioning to the j'th possible value of $S_{m+1}$ given that $S_m$ takes on its i'th possible value.

Figure 11:
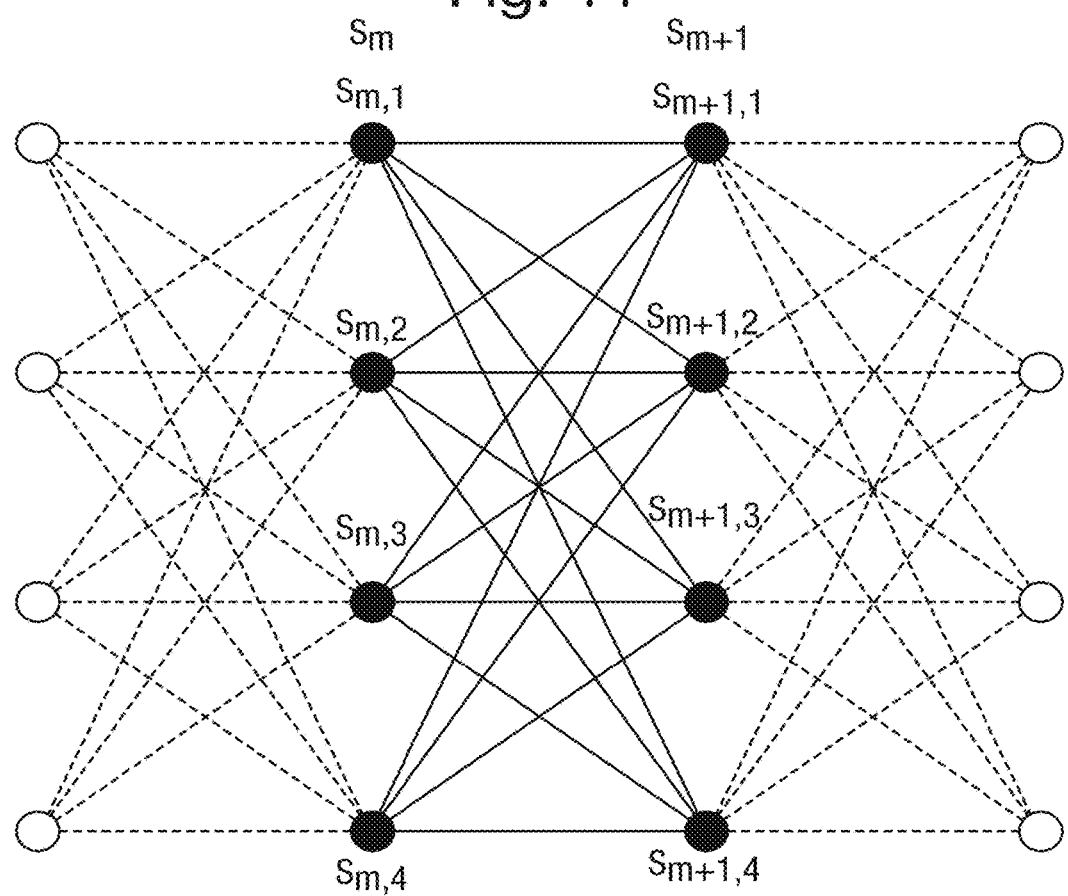
FIG. 11 is a pictorial representation of a transition matrix.

FIG. 11 is a pictorial representation of the transition matrix from $S_m$ to $S_{m+1}$. Here $S_m$ and $S_{m+1}$ only show 4 values for sake of illustration, but in reality there would be as many states as there are different k-mers. Each edge represents a transition, and may be labelled with the entry from the transition matrix representing the transition probability. In FIG. 11, the transition probabilities of the four edges connecting each node in the $S_m$ layer to the $S_{m+1}$ layer would classically sum to one, although non-probabilistic weightings may be used.

In general, it is desirable that the transition weightings 14 comprise values of non-binary variables (non-binary values). This allows the model 13 to represent the actual probabilities of transitions between the k-mers.

Considering that the model 13 represents the k-mers, any given k-mer has k preferred transitions, being transitions from origin k-mers to destination k-mers that have a sequence in which the first (k−1) polymer units are the final (k−1) polymer unit of the origin k-mer. For example in the case of polynucleotides consisting of the 4 nucleotides G, T, A and C, the origin 3-mer TAC has preferred transitions to the 3-mers ACA, ACC, ACT and ACG. To a first approximation, conceptually one might consider that the transition probabilities of the four preferred transitions are equal being (0.25) and that the transition probabilities of the other non-preferred transitions are zero, the non-preferred transitions being transitions from origin k-mers to destination k-mers that have a sequence different from the origin k-mer and in which the first (k−1) polymer units are not the final) polymer units of the origin k-mer. However, whilst this approximation is useful for understanding, the actual chances of transitions may in general vary from this approximation in any given measurement system. This can be reflected by the transition weightings 14 taking values of non-binary variables (non-binary values). Some examples of such variation that may be represented are as follows.

One example is that the transition probabilities of the preferred transitions might not be equal. This allows the model 13 to represent polymers in which there is an inter-relationship between polymers in a sequence.

One example is that the transition probabilities of at least some of the non-preferred transitions might be non-zero. This allows the model 13 to take account of missed measurements, that is in which there is no measurement that is dependent on one (or more) of the k-mers in the actual polymer. Such missed measurements might occur either due to a problem in the measurement system such that the measurement is not physically taken, or due to a problem in the subsequent data analysis, such as the state detection step S1 failing to identify one of the groups of measurements, for example because a given group is too short or two groups do not have sufficiently separated levels.

Notwithstanding the generality of allowing the transition weightings 14 to have any value, typically it will be the case that the transition weightings 14 represent non-zero chances of the preferred transitions from origin k-mers to destination k-mers that have a sequence in which the first (k−1) polymer units are the final (k−1) polymer unit of the origin k-mer, and represent lower chances of non-preferred transitions. Typically also, the transition weightings 14 represent non-zero chances of at least some of said non-preferred transitions, even though the chances may be close to zero, or may be zero for some of the transitions that are absolutely excluded.

To allow for single missed k-mers in the sequence, the transition weightings 14 may represent non-zero chances of non-preferred transitions from origin k-mers to destination k-mers that have a sequence wherein the first (k−2) polymer units are the final (k−2) polymer unit of the origin k-mer. For example in the case of polynucleotides consisting of 4 nucleotides, for the origin 3-mer TAC these are the transitions to all possible 3-mers starting with C. We may define the transitions corresponding to these single missed k-mers as "skips."

In the case of analysing the series of measurements 12 comprising a single measurement in respect of each k-mer, then the transition weightings 14 will represent a high chance of transition for each measurement 12. Depending on the nature of the measurements, the chance of transition from an origin k-mer to a destination k-mer that is the same as the origin k-mer may be zero or close to zero, or may be similar to the chance of the non-preferred transitions.

Similarly in the case of analysing a series of measurements 12 comprising a predetermined number of measurements in respect of each k-mer, then the transition weightings 14 may represent a low or zero chance of transition between the measurements 12 in respect of the same k-mer. It is possible to change the transition weightings 14 to allow the origin k-mer and destination k-mer to be the same k-mer. This allows, for example, for falsely detected state transitions. We may define the transitions corresponding to these repeated same k-mers as "stays." We note that in the case where all of the polymer units in the k-mer are identical, a homopolymer, a preferred transition would be a stay transition. In these cases the polymer has moved one position but the k-mer remains the same.

Similarly, in the case that in the case of analysing a series of measurements 12 in which there are typically plural measurements in respect of each k-mer but of unknown quantity (which may be referred to as "sticking"), the transition weightings 14 may represent a relatively high probability of the origin k-mer and destination k-mer being the same k-mer, and depending on the physical system may in some cases be larger than the probability of preferred transitions as described above being transitions from origin k-mers to destination k-mers in which the first (k−1) polymer units are the same as the final (k−1) polymer units of the origin k-mer Furthermore, in the case of analysing the input signal 11 without using the state detection step S1, then this may be achieved simply by adapting the transition weightings 14 to represent a relatively high probability of the origin k-mer and destination k-mer to be the same k-mer. This allows fundamentally the same analysis step S2 to be performed, the adaptation of the model 13 taking account implicitly of state detection.

Associated with each k-mer, there is an emission weighting 15 that represents the probability of observing given values of measurements for that k-mer. Thus, for the k-mer state represented by the node $S_{m,i}$ in FIG. 11, the emission weighting 15 may be represented as a probability density function $g(X_m|s_{m,i})$ which describes the distribution from which current measurements are sampled. It is desirable that the emission weightings 15 comprise values of non-binary variables. This allows the model 13 to represent the probabilities of different current measurements, that might in general not have a simple binary form.

In the case that the state detection step S1 derives a series of measurements 12 consisting of plural measurement in respect of each identified group (for example a mean and a variance), the emission weightings 15 represent probabilities of observing given values of each type of measurement for that k-mer. Similarly, in the more general case that the method is performed on plural series of measurements 12 that are registered so that it is known a priori which measurements from the respective series correspond and are dependent on the same k-mer, the emission weightings 15 again represent probabilities of observing given values of the measurements of each series for that k-mer. In these cases, the model 13 may be applied using the emission weightings 15 as a probability density function in plural dimensions which describes the distribution of the plural measurements for each k-mer state. In general, the emission weightings 15 for any given k-mer may take any form that reflects the probability of measurements. Different k-mers are not required to have emission weightings 15 with the same emission distributional form or parameterisation within a single model 13.

For many measurement systems, the measurement of a k-mer has a particular expected value that can be spread either by a spread in the physical or biological property being measured and/or by a measurement error. This can be modelled in the model 13 by using emission weightings 15 that have a suitable distribution, for example one that is unimodal.

However, for some measurement systems, the emission weightings 15 for any given k-mer may be multimodal, for example arising physically from two different types of binding in the measurement system and/or from the k-mer adopting multiple conformations within the measurement system.

Advantageously, the emission weightings 15 may represent non-zero chances of observing all possible measurements. This allows the model 13 to take account of unexpected measurements produced by a given k-mer, that are outliers. For example the emission weightings 15 probability density function may be chosen over a wide support that allows outliers with non-zero probability. For example in the case of a unimodal distribution, the emission weightings 15 for each k-mer may have a Gaussian or Laplace distribution which have non-zero weighting for all real numbers.

It may be advantageous to allow the emission weightings 15 to be distributions that are arbitrarily defined, to enable elegant handling of outlier measurements and dealing with the case of a single state having multi-valued emissions.

It may be desirable to determine the emission weightings 15 empirically, for example during a training phase as described below.

The distributions of the emission weightings 15 can be represented with any suitable number of bins across the measurement space. For example, in a case described below the distributions are defined by 500 bins over the data range. Outlier measurements can be handled by having a non-zero probability in all bins (although low in the outlying bins) and a similar probability if the data does not fall within one of the defined bins. A sufficient number of bins can be defined to approximate the desired distribution.

Thus particular advantages may be derived from the use of transition weightings 14 that represent non-zero chances of at least some of said non-preferred transitions and/or the use of emission weightings 15 that represent non-zero chances of observing all possible measurements. Particular advantages may also be derived from the use of emission weightings that correspond to the relative chance of observing a range of measurements for a given k-mer.

To emphasise these advantages, a simple non-probabilistic method for deriving sequence is considered as a comparative example. In this comparative example, k-mers producing measurements outside a given range of the observed value are disallowed and transitions corresponding to missed measurements (skips) are disallowed, for example reducing the number of transitions in FIG. 11 by deleting edges and nodes. In the comparative example a search is then made for the unique connected sequence of k-mer states, containing exactly one node for each $S_t$, and corresponding to an underlying sequence of polymer units. However, as this comparative example relies on arbitrary thresholds to identify disallowed nodes and edges, it fails to find any path in the case of a skipped measurement since the appropriate edge does not exist in the graph. Similarly in the case of an outlying measurement, the comparative example will result in the corresponding node being deleted in FIG. 11, and again the correct path through the graph becomes impossible to ascertain.

In contrast a particular advantage of the use of a model 13 and an analytical technique in the analysis step S2, such as a probabilistic or weighted method, is that this breakdown case can be avoided. Another advantage is that in the case where multiple allowed paths exist, the most likely, or set of likely paths can be determined.

Another particular advantage of this method relates to detection of homopolymers, that is a sequence of identical polymer units. The model-based analysis enables handling of homopolymer regions up to a length similar to the number of polymer units that contribute to the signal. For example a 6-mer measurement could identify homopolymer regions up to 6 polymer units in length.

Figure 8:
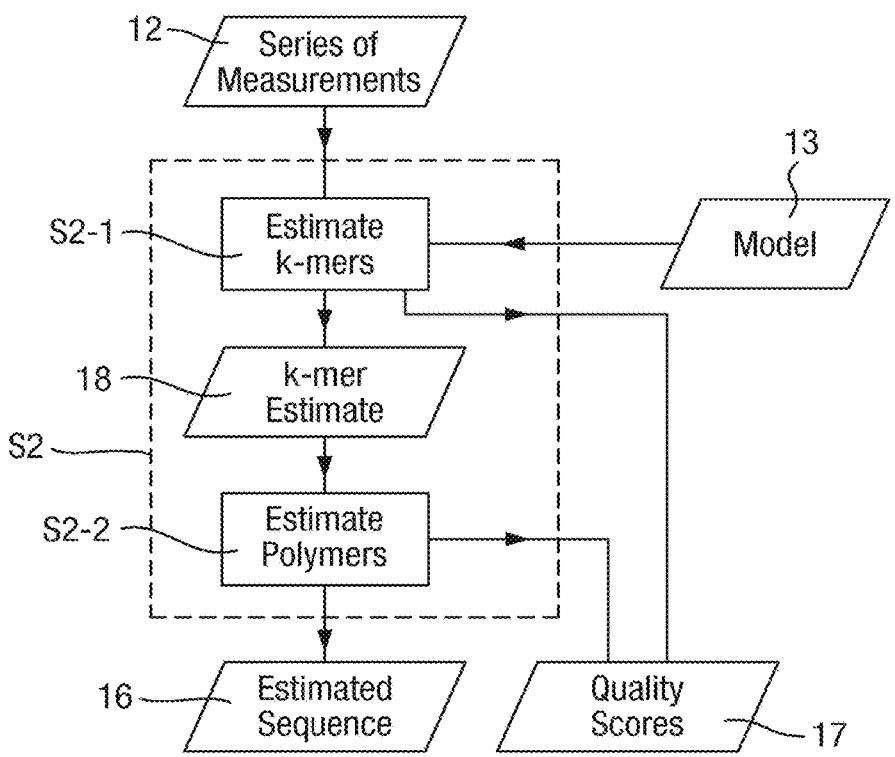
FIG. 8 is a flowchart of an analysis step of FIG. 6.

One possible form of the analysis step S2 is shown in FIG. 8 and operates as follows.

In step S2-1, an estimated sequence 18 of k-mers is estimated with reference to the model 13 based on the likelihood predicted by the model 13 of the series of measurements 12 being produced by sequences of k-mers.

In step S2-2, the estimated sequence 16 of polymer units is estimated from the estimated sequence 18 of k-mers estimated in step S2-1.

In both steps S2-1 and S2-2, there are also provided quality scores that represent the quality of, respectively, the estimated sequence 18 of k-mers and the estimated sequence 16 of polymer units, as discussed further below.

The analytical technique applied in the analysis step S2 may take a variety of forms that are suitable to the model 13 to provide the estimated sequence 16 of polymer units in the polymer based on the likelihood predicted by the model 13 of the series of measurements 12 being produced by sequences of polymer units. For example in the case that the model is an HMM, the analysis technique may use in step S2-1 any known algorithm, for example the Forwards Backwards algorithm or the Viterbi algorithm. Such algorithms in general avoid a brute force calculation of the likelihood of all possible paths through the sequence of states, and instead identify state sequences using a simplified method based on the likelihood.

In one alternative, step S2-1 may identify the sequence 18 of k-mers by estimating individual k-mers of the sequence, or plural k-mer estimates for each k-mer in the sequence, based on the likelihood predicted by the model of the series of measurements being produced by the individual k-mers. As an example, where the analysis technique use the Forwards Backwards algorithm in step S2-1, the analysis technique estimates the sequence 18 of k-mers based on the likelihood predicted by the model of the series of measurements being produced by the individual k-mers. The Forwards-Backwards algorithm is well known in the art. For the forwards part: the total likelihood of all sequences ending in a given k-mer is calculated recursively forwards from the first to the last measurement using the transition and emission weightings. The backwards part works in a similar manner but from the last measurement through to the first. These forwards and backwards probabilities are combined and along with the total likelihood of the data to calculate the probability of each measurement being from a given k-mer.

From the Forwards-Backwards probabilities, an estimate of each k-mer in the sequence 18 is derived. This is based on the likelihood associated with each individual k-mer. One simple approach is to take the most likely k-mer at each measurement, because the Forwards-Backwards probabilities indicate the relative likelihood of k-mers at each measurement.

In step S2-1, quality scores also are derived in respect of individual k-mers in the sequence 18, that represent the likelihoods predicted by the model 13 of the series of measurements 12 being produced by a sequence including the individual k-mers. This may be obtained from the analysis performed in step S2-1, and provides additional useful information.

In another alternative, step S2-1 may identify the sequences 18 of k-mers by estimating the overall sequence, or plural overall sequences, based on the likelihood predicted by the model of the series of measurements being produced by overall sequences of k-mers. As another example, where the analysis technique uses the Viterbi algorithm in step S2-1, the analysis technique estimates the sequence 18 of k-mers based on the likelihood predicted by the model of the series of measurements being produced by an overall sequences of k-mers. The Viterbi algorithm is well known in the art.

In step S2-1, quality scores also are derived in respect of individual k-mers in the sequence 18, that represent the likelihoods predicted by the model 13 of the series of measurements 12 being produced by the overall sequence of k-mers. This may be obtained from the analysis performed in step S2-1, and provides additional useful information.

As another alternative, step S2-1 may be broken into two stages, comprising: a first stage of identifying overall sequences of k-mers, based on the likelihood predicted by the model of the series of measurements being produced by the overall sequences of k-mers; and a second stage of identifying the sequence 18 of k-mers by estimating, from the results of the first stage, individual k-mers of the sequence, or plural k-mer estimates for each k-mer in the sequence. As an example, this alternative may use brute force calculations.

In step S2-2, the estimated sequence 16 of polymer units is estimated from the estimated sequence 18 of k-mers estimated in step S2-1 using any suitable technique. One straightforward approach is to relate k-mers to polymer units in a one-to-one relationship and to simply take a single polymer unit from the related k-mer. More complicated approaches estimate each polymer unit using a combination of information from the group of estimated k-mers in the sequence 18 that contain each given polymer unit. For example the polymer unit may be taken from most probable of those estimated k-mers. Each polymer unit may be estimated making use of the quality scores 17 derived in respect of the estimated k-mer sequence in step S2-1.

In step S2-2, quality scores also are derived in respect of each polymer unit in the sequence 16, that represent the likelihoods predicted by the model 13 of the series of measurements 12 being produced by a sequence including the polymer units. This may be obtained from the analysis performed in step S2-2, for example based on the relative probability of each k-mer and the associated polymer units, and provides additional useful information.

The above techniques in the analysis step S2 are not limitative. There are many ways to utilise the model using a probabilistic or other analytical technique. The process of estimating an overall sequence of k-mers, individual k-mers or underlying polymer units can be tailored to a specific application. It is not necessary to make ally "hard" k-mer sequence, k-mer or polymer unit calls. There can be considered all k-mer sequences, or a sub-set of likely k-mer sequences. There can be considered k-mers or sets of k-mers either associated with k-mer sequences or considered independently of particular k-mer sequences, for example a weighted sum over all k-mer sequences. Polymer units or sets of polymer units associated with k-mers or considered independently of particular k-mers, for example a weighted sum over all k-mers, those k-mers either dependent on, or independent of k-mer sequences or sets of k-mer sequences.

By way of example a 3-mer polynucleotide system may be considered. There are several ways to derive a set of likely base estimates. A first alternative is to consider the most likely path (Viterbi algorithm), derive the set of 3-mer states associated with that path and use one base from the k-mer, for example the central base, as the base call. A second alternative is to consider all paths to derive the most likely k-mer at each point (Forwards-Backwards algorithm). One base from the most likely k-mer (for example the central base) could then be the base estimate. An alternative way to derive the base estimate from the k-mers would be to sum over all k-mers considering contributions of one of the bases (for example the central base) and taking the most likely base as the estimate. An alternative way to derive the base estimate from the k-mers would be to sum the contributions from all positions in all k-mers to determine the most likely estimate at each position.

Similarly, the analysis step S2 may estimate plural sequences 18 of k-mers and/or plural sequences 16 of polymer units. In this case, there may be derived quality scores in respect of each of the plural sequences 18 of k-mers and/or each of the plural sequences 16 of polymer units. In this way, the analysis step S2 provides information on less likely sequences, that may nonetheless be useful in some applications.

The above description is given in terms of a model 13 that is a HMM in which the transition weightings 14 and emission weightings 15 are probabilities and the analysis step S2 uses a probabilistic technique that refers to the model 13. However, it is alternatively possible for the model 13 to use a framework in which the transition weightings 14 and/or the emission weightings 15 are not probabilities but represent the chances of transitions or measurements in some other way. In this case, the analysis step S2 may use an analytical technique other than a probabilistic technique that is based on the likelihood predicted by the model 13 of the series of measurements being produced by sequences of polymer units. The analytical technique used by the analysis step S2 may explicitly use a likelihood function, but in general this is not essential. Thus in the context of the present invention, the term "likelihood" is used in a general sense of taking account of the chance of the series of measurements being produced by sequences of polymer units, without requiring calculation or use of a formal likelihood function.

For example, the transition weightings 14 and/or the emission weightings 15 may be represented by costs (or distances) that represent the chances of transitions or emissions, but are not probabilities and so for example are not constrained to sum to one. In this case, the analysis step S2 may use an analytical technique that handles the analysis as a minimum cost path or minimum path problem, for example as seen commonly in operations research. Standard methods such as Dijkstra's algorithm (or other more efficient algorithms) can be used for solution.

There will now be discussed a specific example in which the model 13 is a HMM that is used to model and analyse data from a blunt reader head system. Here, the input data 11 is first processed by the state detection step S1 as described previously. For simplicity, but without limitation, this specific example relates to a 3-mer model for a polynucleotide having 4 possible bases such that there are 64 possible k-mers. A simulated case is presented to enable illustration of the key points with reference to the underlying model 13 and states.

In this simulated case, the 3-mer current levels are selected randomly, such that the simplest description of the emission weightings 15 of the 64 k-mer states requires the 64 coefficients. Determination of the underlying sequence of k-mers from a measurement is achieved by a model-based analysis, as described.

Figure 12:
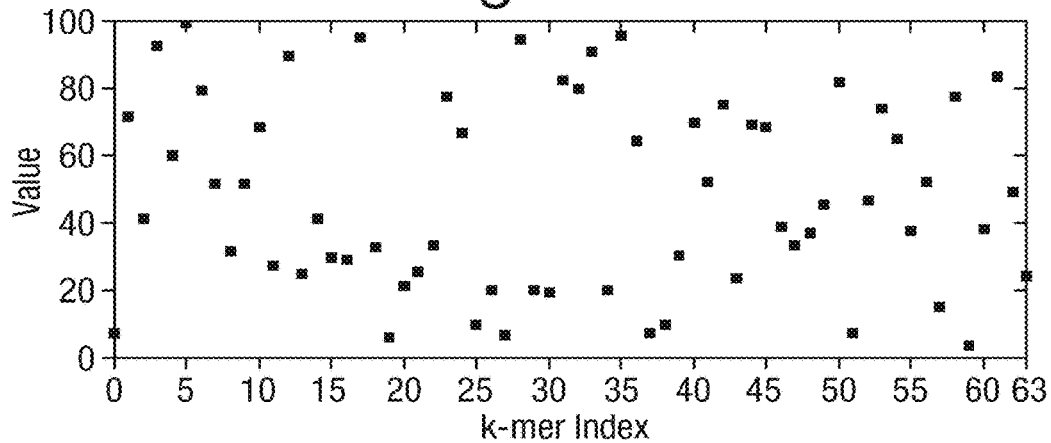
FIG. 12 is a graph of the expected measurements in respect of k-mer states in a simulated example.

FIG. 12 shows for each k-mer, the most likely value of the measurement. These values are therefore also the central values of the distributions for the emission weightings 15 of each k-mer. In FIG. 12, k-mer state indices run sequentially in order G, T, A, C, i.e. state 0="GGG", state 1="GGT", . . . state 62="CCA", state 63="CCC". K-mer state indices are used during the analysis with conversion back to "base space" as a final step.

Figure 13:
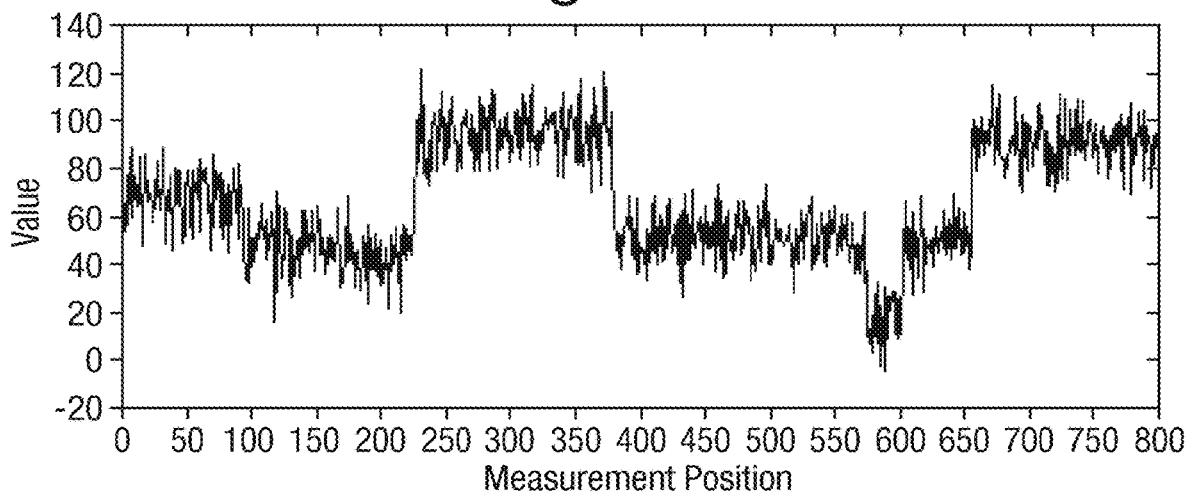
FIG. 13 shows an input signal simulated from the expected measurements illustrated in FIG. 12.
Figure 14:
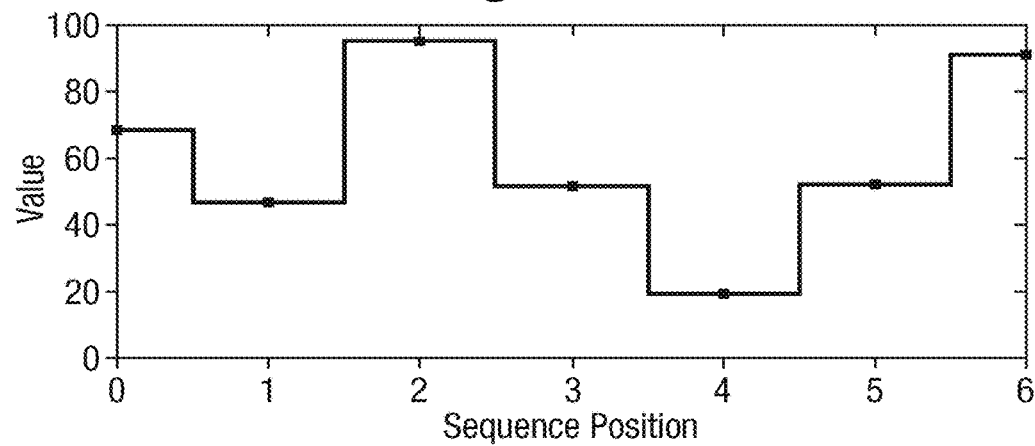
FIG. 14 shows a series of measurements derived from the input signal of FIG. 13.

Measurements from a given sequence are simulated using the previously described coefficients. For example the sequence ACTGTCAG, is made up of the 3mers: ACT, CTG, TGT, GTC, TCA, CAG. These correspond to state indices 45, 52, 17, 7, 30, 56 which give expected measurements of 68.5, 46.5, 94.9, 51.3, 19.5, 52.1. Simulated measurements are illustrated in FIG. 13 as the input signal 12 and in FIG. 14 as the series of measurements 12 produced by the state detection step S1.

In practice, any measurements made have an error associated with them. In the simulated case, account for this is taken by adding noise to the expected measurements.

There is also the chance of missing a measurement or of inserting a false positive measurement. These can be accounted for in the transition matrix as will now be described.

The transition matrix of transition weightings 14 for the simulated case will now be considered.

Given a series of measurements 12 and the set of emission weightings 15, the analysis step S2 determines an estimate of the underlying sequence. Conceptually, this may be considered as the analysis step S2 modelling all possible transitions against which the observed sequence is compared (although in fact the analysis step S2 may use a more efficient algorithm that does not require this). For example in the 3-mer case under consideration, each of the 64 states has preferred transitions to four other states.

Figure 15:
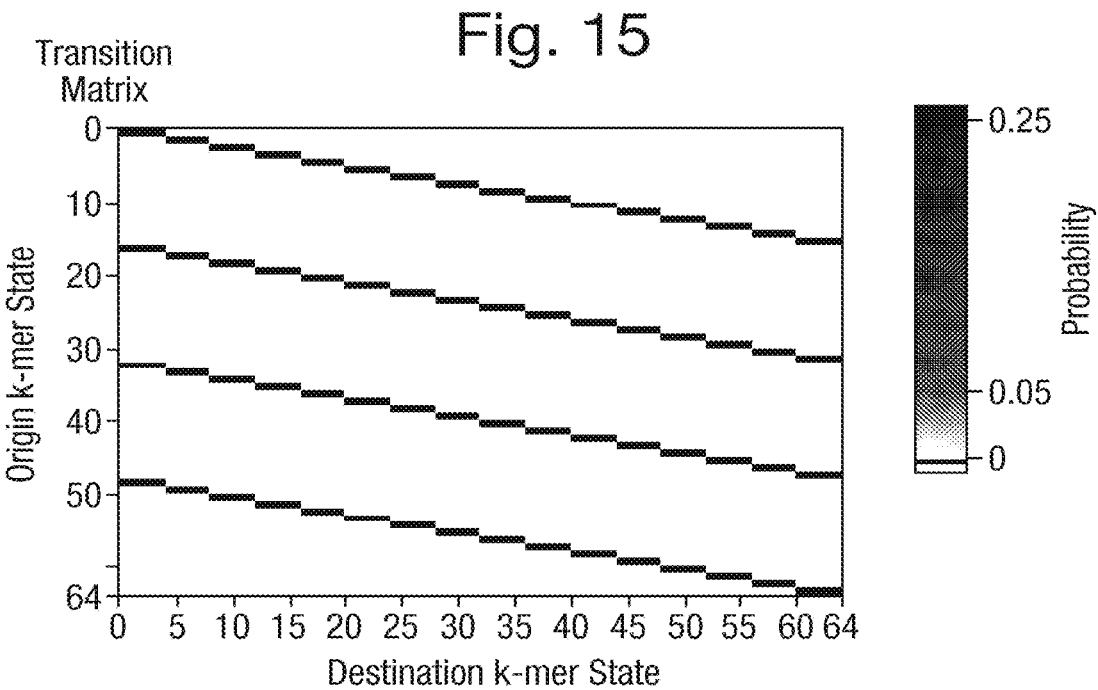
FIGS. 15 and 16 show respective transition matrices of transition weightings.

FIG. 15 illustrates a transition matrix of transition weightings 14 for the simulated model in which the transition weightings 14 for preferred transitions are each 0.25 and the transition weightings 14 for non-preferred transitions are each zero. For example it can be seen that origin state 0 (GGG) can transition to states, 0 (GGG), 1 (GGT), 2 (GGA) or 3 (GGC) with equal probabilities.

Figure 16:
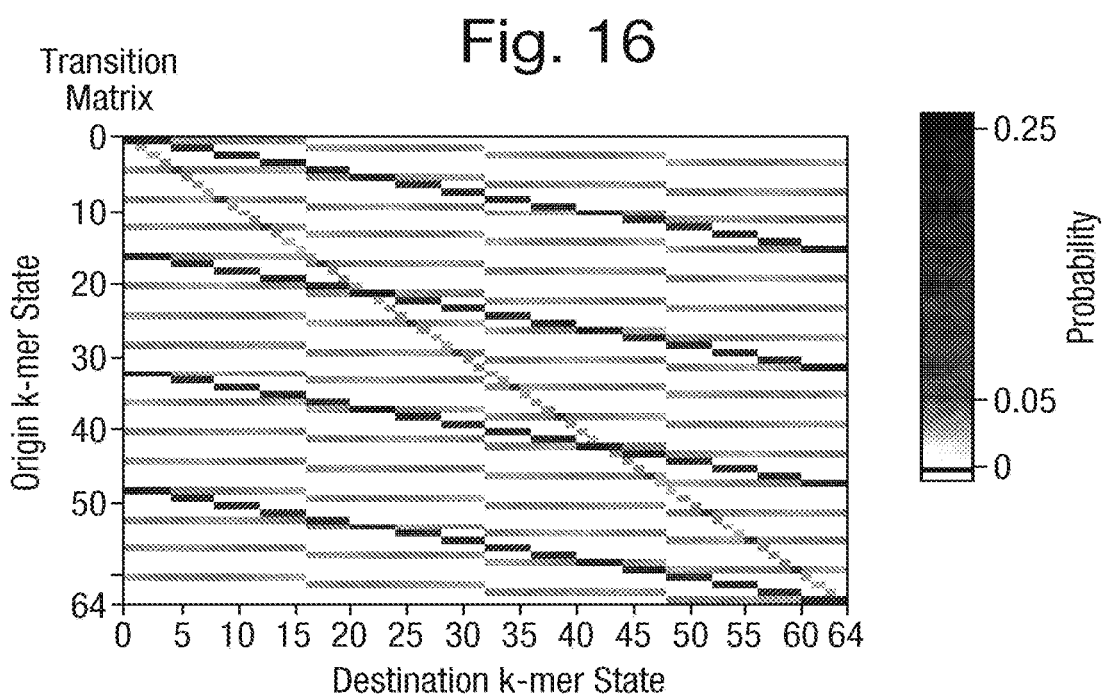

FIG. 16 illustrates a more complicated case of a transition matrix of transition weightings 14 for the simulated model modified from that of FIG. 15 by allowing non-zero transition weightings 14 for non-preferred transitions that represent a missed measurement, i.e. in which a transition is skipped. In general terms, the transition matrix can be arbitrarily complex as needed to model the underlying measurement system.

In the case of operating on the series of measurements 12, where we have performed state detection S1, transition probabilities away from any given origin k-mer are typically high, in sum approaching 1. In the first example of FIG. 15, transition matrix requires a transition, except in the four homopolymer cases where one of the preferred "transitions" is to the same k-mer. The probability of each of the four preferred transitions from any state is 0.25. This matrix is unlikely to be able to handle "real world" data unless other appropriate mitigation is made, for example outlier handling in the emission weightings 15.

However, non-zero transitions can be allowed for any case that it is required to deal with or is likely to occur. In the second example of FIG. 16, the probabilities of the preferred transitions are less than 0.25, with the remainder made up from the stay and skip probabilities. Multiple skips may also be permitted in a similar manner up to an arbitrary level of complexity.

Transition probabilities can be tuned to take into account the ease with which a transition between k-mers can be measured. For example in the case of the signal from two sequential k-mers being very close together, it is possible for the state detection step S1 to miss this transition. In this case, the transition matrix elements between these two k-mers may be weighted in the direction of skipping the second k-mer.

The matrix may be tuned to take into account any sequence bias in a given sample.

In the above examples, the emission and transition weightings are fixed at a constant value but this is not essential. As an alternative the emission weightings and/or transition weightings may be varied for different sections of the measurement series to be analysed, perhaps guided by additional information about the process. As an example, an element of the matrix of transition weightings which has an interpretation as a "stay" could be adjusted depending on the confidence that a particular event ( ) reflects an actual transition of the polymer. As a further example, the emission weightings could be adjusted to reflect systematic drift in the background noise of the measuring device or changes made to the applied voltage. The scope of adjustments to the weightings is not limited to these examples.

In the above example, there is a single representation of each k-mer, but this is not essential. As an alternative, the model may have plural distinct representations of some or all of the k-mers, so that in respect of any given k-mer there may be plural sets of transition and/or emission weightings. The transition weightings here could be between distinct origin and distinct destination k-mers, so each origin-destination pair may have plural weightings depending on the number of distinct representations of each k-mer. One of many possible interpretations of these distinct representations is that the k-mers are tagged with a label indicating some behaviour of the system that is not directly observable, for example different conformations that a polymer may adopt during translocation through a nanopore or different dynamics of translocation behaviour.

For a model 13 operating on the raw input signal 11 without performing the state detection step S1, the method is applied directly to the input series of measurements in which groups of plural measurements are dependent on the same k-mer without a priori knowledge of the the number of measurements in a group. In this case, very similar techniques can be applied, but with a significant adjustment to the model 13 in that the sum of the transition probabilities away from any given origin k-mer state is now much less than 1. For example, if on average the system spends 100 measurements at the same k-mer the probability on the diagonals in the transition matrix (representing no transition or a transition in which the origin k-mer and destination k-mer are the same k-mer)) will be 0.99 with 0.01 split between all the other preferred and non-preferred transitions. The set of preferred transitions may be similar to those for the state detection case.

Figure 17:
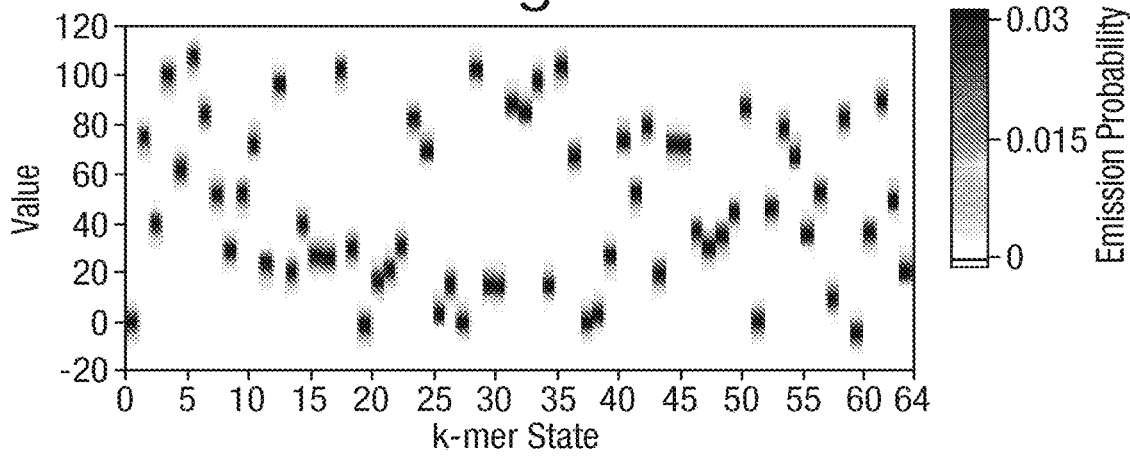
FIGS. 17 to 19 are graphs of emission weightings having possible distributions that are, respectively, Gaussian, triangular and square.
Figure 18:
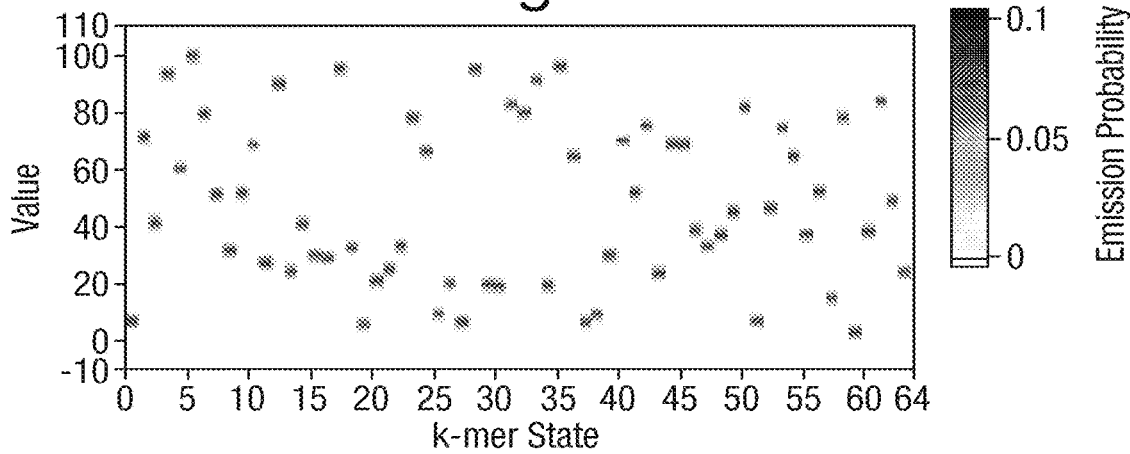
Figure 19:
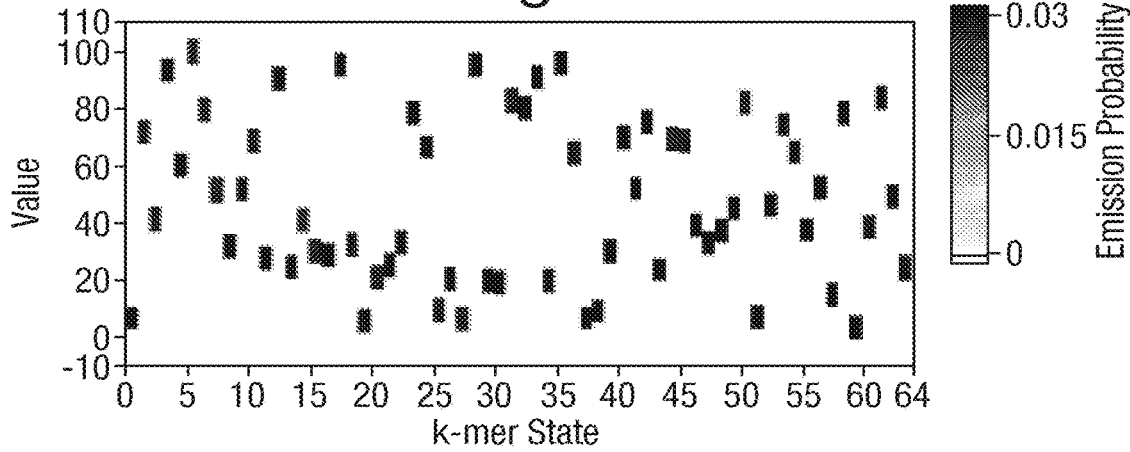

Considering the emission weightings 15, FIGS. 17 to 19 show emission distributions for the simulated coefficients that are, respectively, Gaussian, triangular and square distributions, although any arbitrary distribution (including non-parametric distributions) can be defined in this manner.

To demonstrate the robustness of these methods to noise, a noise perturbation is added to the simulated measurements. In this example, a random noise, sampled from a Gaussian distribution of standard deviation 5 pA, is added to the expected k-mer measurements shown in FIG. 12.

Figure 20:
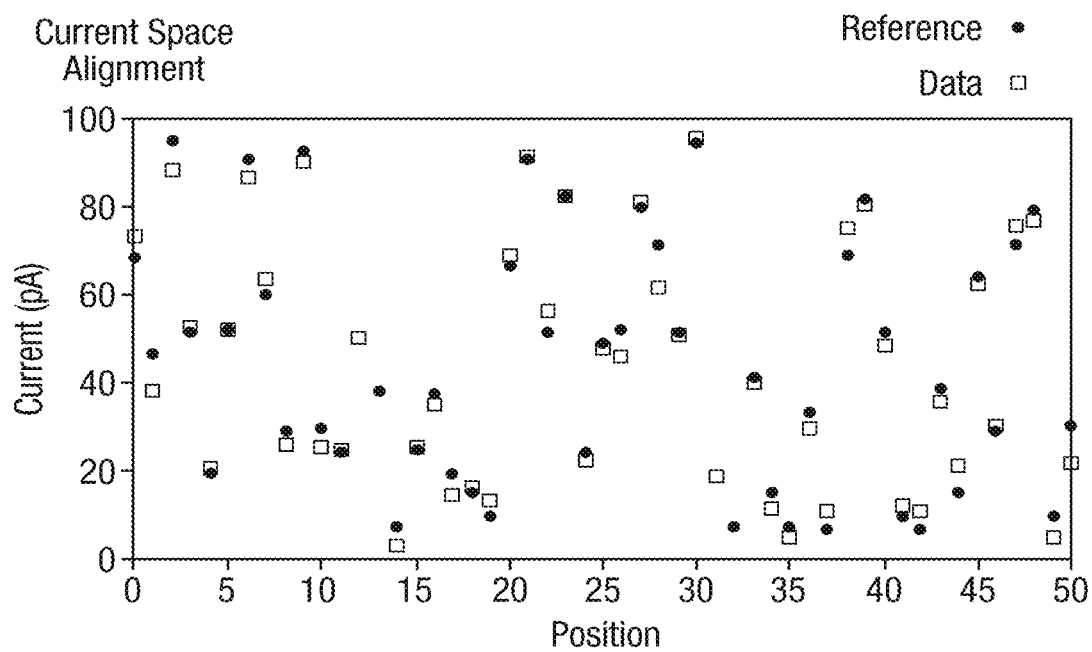
FIG. 20 is a graph of the current space alignment between a set of simulated measurements and the expected measurements shown in FIG. 12.

FIG. 20 shows the simulated measurements (series of measurements 12) compared to the expected measurements shown in FIG. 12, illustrating the added noise which can be seen to be severe.

Figure 21:
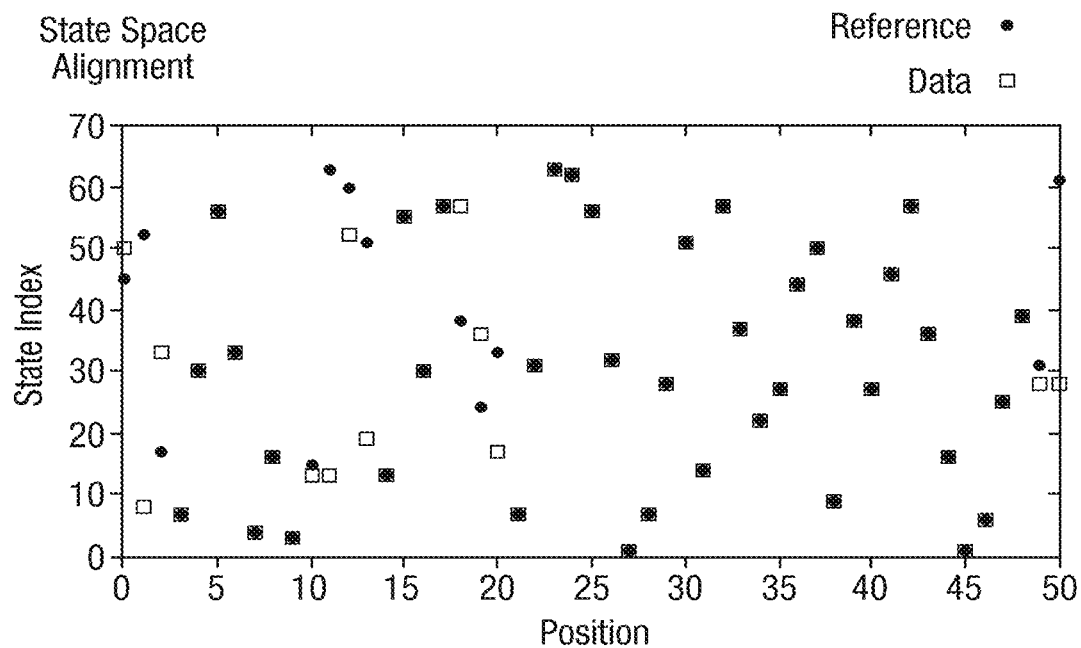
FIG. 21 is a graph of the k-mer space alignment between the actual k-mers and the k-mers, estimated from the simulated measurements of FIG. 20.

The model 13 is applied with an appropriate transition matrix of transition weightings, for example that shown in FIG. 16, and appropriate distribution for the emission weightings 15, in this case a Gaussian distribution. The Forwards-Backwards algorithm is used as an analytical technique to estimate the most likely k-mer at each point in the series of measurements. The estimated k-mer calls are compared against the known k-mer sequence, as shown in FIG. 21. It can be seen that even in this severe case, the majority of states are estimated correctly.

Figure 22:
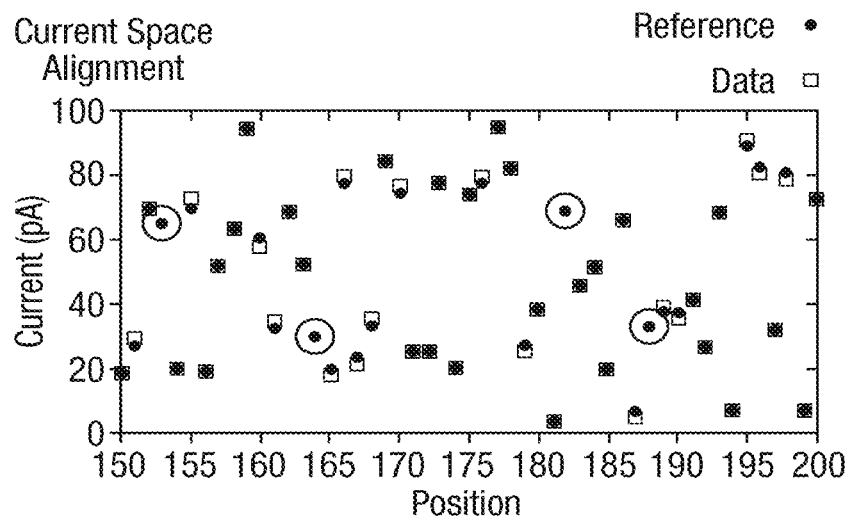
FIG. 22 is a graph of the current space alignment between a further set of simulated measurements and the expected measurements shown in FIG. 12.

The robustness to missing measurements associated with the k-mers in the sequence is now illustrated. In this case, a series of measurements 12 is simulated in which, in addition to adding noise to the expected k-mer measurements (in this example we use a less severe case of noise with 1 pA standard deviation), k-mer measurements are also deleted at random from the data, in this case with a probability of deletion of 0.1. FIG. 22 shows the simulated measurements (series of measurements 12) compared to the expected measurements shown in FIG. 12. The missing k-mer states can be seen, circled, in FIG. 22.

Again, the model 13 of the expected k-mer measurements is applied with an appropriate transition matrix of transition weightings, in this case with both those shown in FIGS. 15 and 16, and appropriate distribution for the emission weightings 15, in this case a Gaussian distribution. The Forwards-Backwards algorithm is used as an analytical technique to estimate the most likely k-mer at each point in the series of measurements 12.

Figure 23:
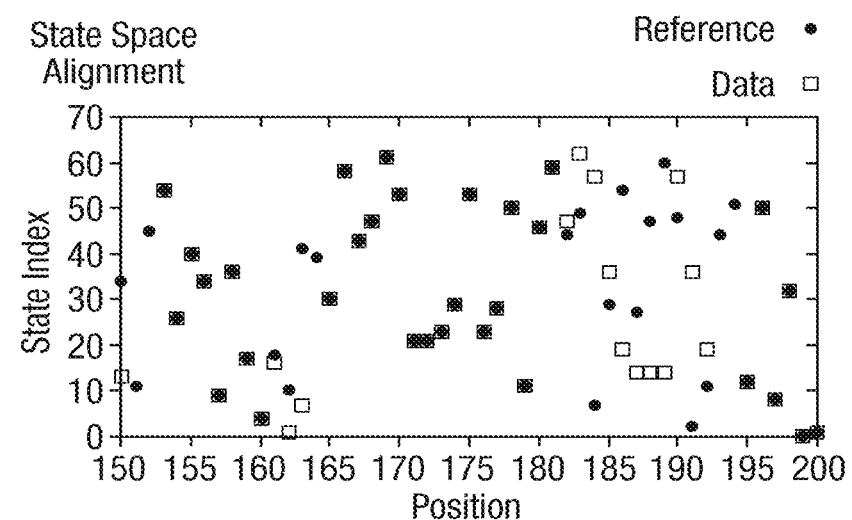
FIGS. 23 and 24 are graphs of the k-mer space alignment between the actual k-mers and the k-mers estimated from the simulated measurements of FIG. 22 with the transition matrices of FIGS. 15 and 16, respectively.
Figure 24:
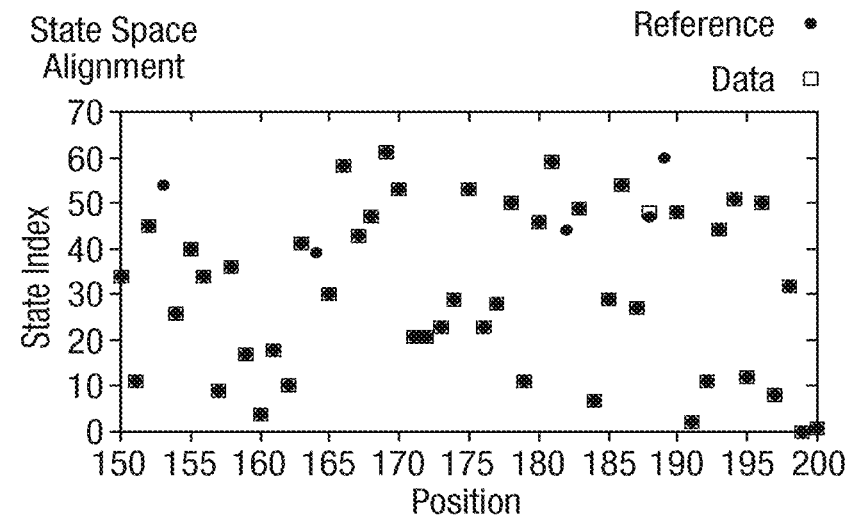

The estimated k-mer calls are compared against the known k-mer sequence, as shown in FIGS. 23 and 24 for the transition matrices of FIGS. 15 and 16, respectively. Here, the improvement in number of correctly called k-mers by allowing skips in the model transitions can be seen in FIG. 24, as compared to FIG. 23. In the case where there is a missing k-mer measurement surrounded by high confidence estimates, the missing k-mer can be estimated from the surrounding k-mers. In contrast for the case of skips not being permitted missing data is accommodated by emission weightings 15 having distributions that do not reach zero in order for the analysis to find a path through the series of k-mers. The non-zero background in emission distributions is further discussed in the next section.

The robustness to outlying measurements associated with given k-mers in the sequence is now illustrated. In the previous illustration concerning missing measurements, where the transition weightings 14 did not permit skipped states (i.e. with the transition matrix of FIG. 15), it was required to use emission weightings 15 with distributions that did not reach zero, to enable the analysis to find a path (albeit a very unlikely one) through the sequence of k-mers. The advantage of emission weightings 15 with non-zero values for all measurements is illustrated in the simple case of square emission distributions. This example uses the simulated series of measurements 12 shown in FIG. 20 in which noise with a standard deviation of 5 pA is added.

Again, the model 13 of the expected k-mer measurements is applied in this case with a transition matrix of transition weightings 14 in which non-preferred transitions are not permitted, as shown in FIG. 15, and with two different distributions for the emission weightings 15. The Forwards-Backwards algorithm is used as an analytical technique to estimate the most likely k-mer at each point in the series of measurements 12.

Figure 25:
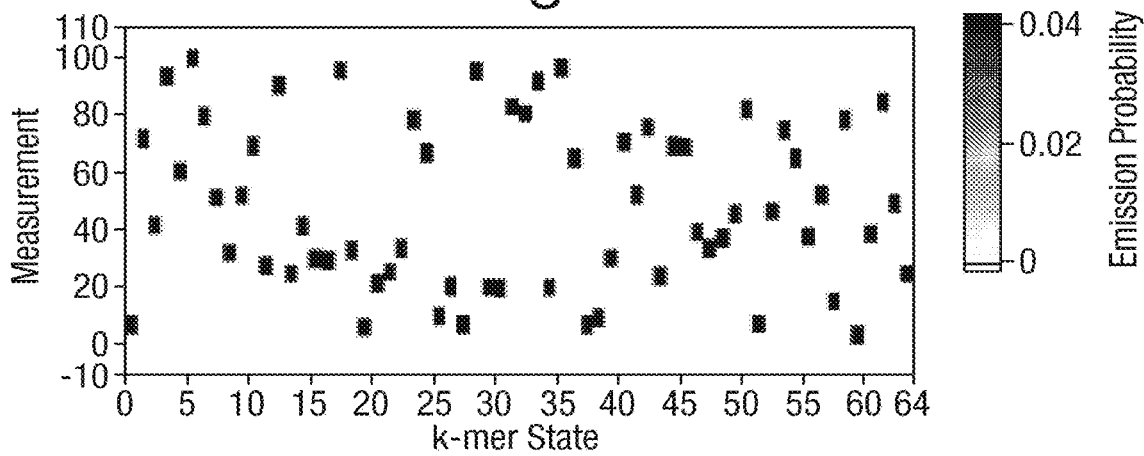
FIG. 25 is a graph of emission weightings having a square distribution with a small non-zero background with distributions centred on the expected measurements of FIG. 12.
Figure 26:
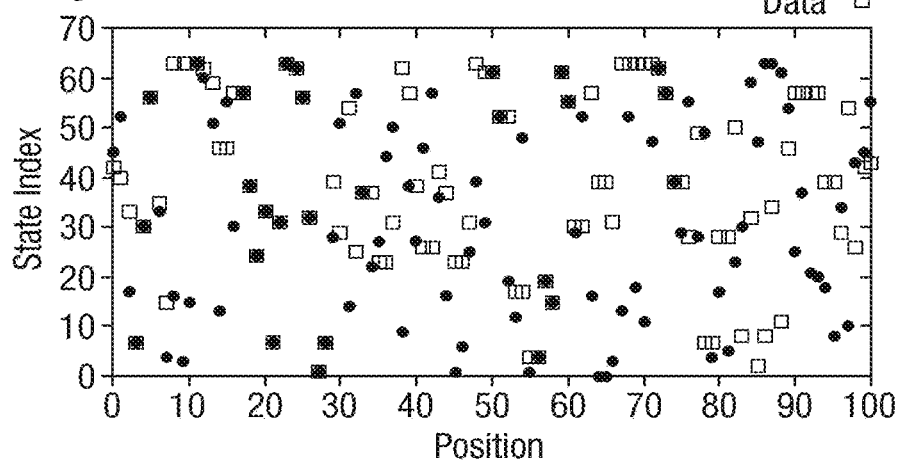
FIG. 26 is a graph of the k-mer space alignment between the actual k-mers and the k-mers estimated from the simulated measurements of FIG. 20 with the transition matrix of FIG. 15 and the emission weightings of FIG. 25.

In a first case, the emission weightings 15 have a square distribution with a small non-zero background (in this case $1 \times 10^{-10}$) as shown in FIG. 25, for which the estimated k-mer calls are compared against the known k-mer sequence in FIG. 26.

Figure 27:
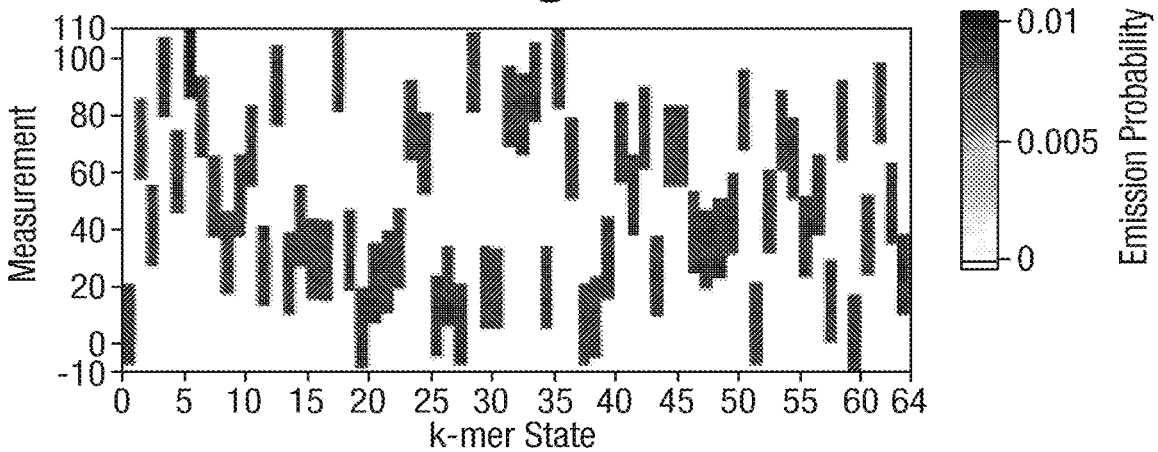
FIG. 27 is a graph of emission weightings having a square distribution with a zero background with distributions centred on the expected measurements of FIG. 12.
Figure 28:
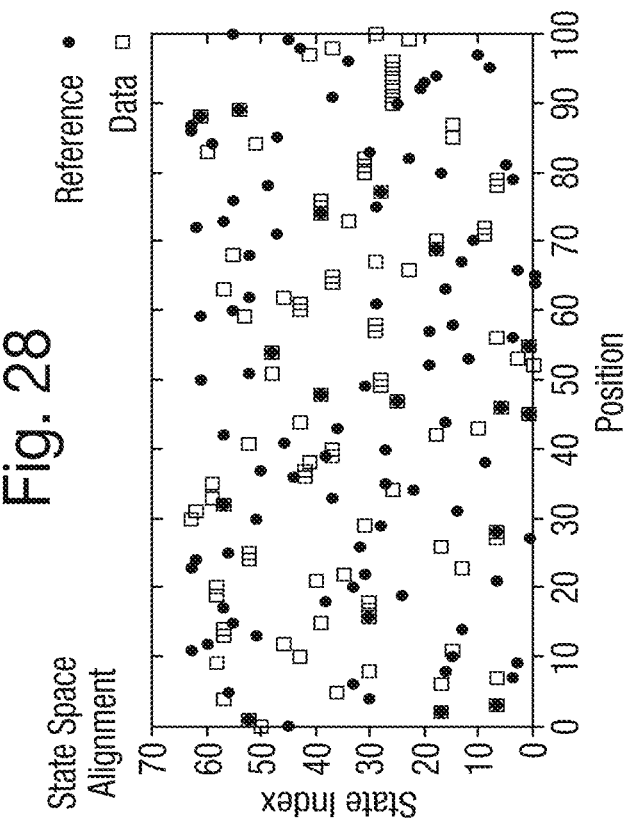
FIG. 28 is a graph of the k-mer space alignment between the actual k-mers and the k-mers estimated from the simulated measurements of FIG. 20 with the transition matrix of FIG. 15 and the emission weightings of FIG. 27.

In a second case, the emission weightings 15 have a square distribution with a zero background as shown in FIG. 27, for which the estimated k-mer calls are compared against the known k-mer sequence in FIG. 28.

In the second case with a zero background in the distributions of the emission weightings 15, no paths through the k-mer sequence exist with emission distributions where the widths of those distributions are too narrow. For this example we have used emission distributions with a width of +/−14 pA such that the analysis can find paths through the measurements, as shown in FIG. 27. In this case, rather than a small number of paths existing, each with a high number of correct states, a large number of paths exist, containing many incorrectly called states. A set of k-mer calls for this example are shown in FIG. 28.

In the first case where a small non-zero emission in the background is permitted as shown in FIG. 25, much more narrow distributions can be tolerated, enabling a higher number of k-mer states to be correctly estimated as shown in FIG. 27 which provides better results than FIG. 28.

Additionally, this example illustrates the advantage of a probabilistic method by comparing the square distribution case to the Gaussian emissions used for the example shown in FIGS. 20 and 21 which provides a better results than the use of square distributions as shown in FIGS. 27 and 28.

There will now be discussed training of the model 13, that is derivation of the emission weightings 15 for a given measurement system.

In contrast to the above simulations, in a real measurement system the individual measurements from each k-mer are not known in advance but can be derived from a training set. In general terms, this involves taking measurements from known polymers and using training techniques that are of themselves conventional for a HMM.

In these training methods, there may be exploited a specific type of sequence, that is a deBruijn sequence being the minimum length sequence containing all k-mers for a given k. use of a deBruijn sequence is an efficient way to minimise the number of experiments required.

Two training methods are described for a measurement system comprising a nanopore used to measure a polynucleotide. The first method uses measurements from "static" DNA strands, held at a particular position within the nanopore by a biotin/streptavidin system. The second method uses measurements from DNA strands translocated through the nanopore and estimates or "trains" the coefficients by exploiting a similar probabilistic framework to that described for k-mer estimation.

The first static training method is performed as follows.

These experiments involved attaching a DNA strand to a streptavidin "anchor" using a biotin molecule in a similar manner to those described by Stoddart D et al., Proc Natl Acad Sci, 12; 106(19):7702-7. In this system the value of k is 3. The DNA strand represents the k=3 deBruijn sequence (Seq TD: 3) using MS-(B2)8 in 400 mM KCl. The strand is captured in the nanopore under an applied potential and the current is recorded. The experiment can be repeated with a series of DNA strands where the sequence is advanced by one nucleotide, as listed in Table 1 below. In this way, measurements of the current levels at a particular applied potential such as 180 mV corresponding to those expected from a moving strand were obtained, as listed in the Table below.

Seq ID 3 (k3 De Bruijn):
ATAAGAACATTATGATCAGTAGGAGCACTACGACCTTTGTTCTGGTGC

TCGTCCGGGCGCCCAAAT

TABLE 1

| Strand | Sequence | Measurement (pA) |
|---|---|---|
| SD01 | CTCTCTCTCTCCTCTCTCTCAAATAAGAACATTATGATCAGTAGG/3BioTEG/ | 63.3 |
| SD02 | CTCTCTCTCTCCTCTCTCTCAATAAGAACATTATGATCAGTAGGA/3BioTEG/ | 72.6 |
| SD03 | CTCTCTCTCTCCTCTCTCTCATAAGAACATTATGATCAGTAGGAG/3BioTEG/ | 68.2 |
| SD04 | CTCTCTCTCTCCTCTCTCTCTAAGAACATTATGATCAGTAGGAGC/3BioTEG/ | 56.7 |
| SD05 | CTCTCTCTCTCCTCTCTCTCAAGAACATTATGATCAGTAGGAGCA/3BioTEG/ | 55.3 |
| SD06 | CTCTCTCTCTCCTCTCTCTCAGAACATTATGATCAGTAGGAGCAC/3BioTEG/ | 75.6 |
| SD07 | CTCTCTCTCTCCTCTCTCTCGAACATTATGATCAGTAGGAGCACT/3BioTEG/ | 69.0 |
| SD08 | CTCTCTCTCTCCTCTCTCTCAACATTATGATCAGTAGGAGCACTA/3BioTEG/ | 64.5 |
| SD09 | CTCTCTCTCTCCTCTCTCTCACATTATGATCAGTAGGAGCACTAC/3BioTEG/ | 57.8 |
| SD10 | CTCTCTCTCTCCTCTCTCTCCATTATGATCAGTAGGAGCACTACG/3BioTEG/ | 64.3 |
| SD11 | CTCTCTCTCTCCTCTCTCTCATTATGATCAGTAGGAGCACTACGA/3BioTEG/ | 80.4 |

TABLE 1-continued

| Strand | Sequence | Measurement (pA) |
|---|---|---|
| SD12 | CTCTCTCTCTCCTCTCTCTCTTATGATCAGTAGGAGCACTACGAC/3BioTEG/ | 77.5 |
| SD13 | CTCTCTCTCTCCTCTCTCTCTATGATCAGTAGGAGCACTACGACC/3BioTEG/ | 65.3 |
| SD14 | CTCTCTCTCTCCTCTCTCTCATGATCAGTAGGAGCACTACGACCT/3BioTEG/ | 68.9 |
| SD15 | CTCTCTCTCTCCTCTCTCTCTGATCAGTAGGAGCACTACGACCTT/3BioTEG/ | 67.1 |
| SD16 | CTCTCTCTCTCCTCTCTCTCGATCAGTAGGAGCACTACGACCTTT/3BioTEG/ | 67.3 |
| SD17 | CTCTCTCTCTCCTCTCTCTCATCAGTAGGAGCACTACGACCTTTG/3BioTEG/ | 66.6 |
| SD18 | CTCTCTCTCTCCTCTCTCTCAGTAGGAGCACTACGACCTTTGT/3BioTEG/ | 77.7 |
| SD19 | CTCTCTCTCTCCTCTCTCTCCAGTAGGAGCACTACGACCTTTGTT/3BioTEG/ | 67.3 |
| SD20 | CTCTCTCTCTCCTCTCTCTCAGTAGGAGCACTACGACCTTTGTTC/3BioTEG/ | 71.6 |
| SD21 | CTCTCTCTCTCCTCTCTCTCGTAGGAGCACTACGACCTTTGTTCT/3BioTEG/ | 76.9 |
| SD22 | TTTTTTTTTTTTTTTTTTTTAGGAGCACTACGACCTTTGTTCTG/3BioTEG/ | 58.2 |
| SD23 | TTTTTTTTTTTTTTTTTTTTAGGAGCACTACGACCTTTGTTCTGG/3BioTEG/ | 68.8 |
| SD24 | CTCTCTCTCTCCTCTCTCTCGGAGCACTACCACCTTTGTTCTGGT/3BioTEG/ | 57.7 |
| SD25 | CTCTCTCTCTCCTCTCTCTCGAGCACTACGACCTTTGTTCTGGTG/3BioTEG/ | 49.1 |
| SD26 | CTCTCTCTCTCCTCTCTCTCAGCACTACGACCTTTGTTCTGGTGC/3BioTEG/ | 50.4 |
| SD27 | CTCTCTCTCTCCTCTCTCTCGCACTACGACCTTTGTTCTGGTGCT/3BioTEG/ | 65.8 |
| SD28 | TTTTTTTTTTTTTTTTTTTCACTACGACCTTTGTTCTGGTGCTC/3BioTEG/ | 50.3 |
| SD29 | TTTTTTTTTTTTTTTTTTTTACTACGACCTTTGTTCTGGTGCTCG/3BioTEG/ | 53.0 |
| SD30 | CTCTCTCTCTCCTCTCTCTCCTACGACCTTTGTTCTGGTCCTCGT/3BioTEG/ | 52.6 |
| SD31 | CTCTCTCTCTCCTCTCTCTCTACGACCTTTGTTCTGGTGCTCGTC/3BioTEG/ | 60.4 |
| SD32 | CTCTCTCTCTCCTCTCTCTCACGACCTTTGTTCTGGTGCTCGTCC/3BioTEG/ | 69.9 |
| SD33 | CTCTCTCTCTCCTCTCTCTCCGACCTTTGTTCTGGTGCTCGTCCG/3BioTEG/ | 59.5 |
| SD34 | CTCTCTCTCTCCTCTCTCTCGACCTTTGTTCTGGTGCTCGTCCGG/3BioTEG/ | 50.7 |
| SD35 | CTCTCTCTCTCCTCTCTCTCACCTTTGTTCTGGTGCTCGTCCGGG/3BioTEG/ | 50.5 |
| SD36 | CTCTCTCTCTCCTCTCTCTCCCTTTGTTCTGGTGCTCGTCCGGGC/3BioTEG/ | 57.1 |
| SD37 | CTCTCTCTCTCCTCTCTCTCCTTTGTTCTGGTGCTCGTCCGGGCG/3BioTEG/ | 67.6 |
| SD38 | CTCTCTCTCTCCTCTCTCTCTTTGTTCTGGTGCTCGTCCGGGCGC/3BioTEG/ | 58.7 |
| SD39 | CTCTCTCTCTCCTCTCTCTCTTGTTCTGGTGCTCGTCCGGGCGCC/3BioTEG/ | 66.8 |
| SD40 | CTCTCTCTCTCCTCTCTCTCTGTTCTGGTGCTCGTCCGGGCGCCC/3BioTEG/ | 49.6 |
| SD41 | CTCTCTCTCTCCTCTCTCTCGTTCTGGTGCTCGTCCGGGCGCCCA/3BioTEG/ | 58.7 |
| SD42 | CTCTCTCTCTCCTCTCTCTCTTCTGGTGCTCGTCCGGGCGCCCAA/3BioTEG/ | 57.3 |
| SD43 | CTCTCTCTCTCCTCTCTCTCTCTGGTGCTCGTCCGGGCGCCCAAA/3BioTEG/ | 69.4 |
| SD44 | CTCTCTCTCTCCTCTCTCTCCTGGTGCTCGTCCGGGCGCCCAAAT/3BioTEG/ | 57.0 |
| SD45 | CTCTCTCTCTCCTCTCTCTCTGGTGCTCGTCCGGGCGCCCAAATA/3BioTEG/ | 54.0 |
| SD46 | CTCTCTCTCTCCTCTCTCTCGGTGCTCGTCCGGGCGCCCAAATAA/3BioTEG/ | 65.3 |
| SD47 | CTCTCTCTCTCCTCTCTCTCGTGCTCGTCCGGGCGCCCAAATAAG/3BioTEG/ | 66.2 |
| SD48 | CTCTCTCTCTCCTCTCTCTCTGCTCGTCCGGGCGCCCAAATAAGA/3BioTEG/ | 61.3 |
| SD49 | CTCTCTCTCTCCTCTCTCTCGCTCGTCCGGGCGCCCAAATAAGAA/3BioTEG/ | 75.5 |

TABLE 1-continued

| Strand | Sequence | Measurement (pA) |
|---|---|---|
| SD50 | CTCTCTCTCTCCTCTCTCTCCTCGTCCGGGCGCCCAAATAAGAAC/3BioTEG/ | 69.4 |
| SD51 | CTCTCTCTCTCCTCTCTCTCTCGTCCGGGCGCCCAAATAAGAACA/3BioTEG/ | 74.5 |
| SD52 | CTCTCTCTCTCCTCTCTCTCCGTCCGGGCGCCCAAATAAGAACAT/3BioTEG/ | 71.6 |
| SD53 | CTCTCTCTCTCCTCTCTCTCGTCCGGGCGCCCAAATAAGAACATT/3BioTEG/ | 79.2 |
| SD54 | CTCTCTCTCTCCTCTCTCTCTCCGGGCGCCCAAATAAGAACATTA/3BioTEG/ | 58.5 |
| SD55 | CTCTCTCTCTCCTCTCTCTCCCGGGCGCCCAAATAAGAACATTAT/3BioTEG/ | 78.2 |
| SD56 | CTCTCTCTCTCCTCTCTCTCCGGGCGCCCAAATAAGAACATTATG/3BioTEG/ | 81.5 |
| SD57 | CTCTCTCTCTCCTCTCTCTCGGGCGCCCAAATAAGAACATTATGA/3BioTEG/ | 84.7 |
| SD58 | CTCTCTCTCTCCTCTCTCTCGGCGCCCAAATAAGAACATTATGAT/3BioTEG/ | 71.7 |
| SD59 | CTCTCTCTCTCCTCTCTCTCGCGCCCAAATAAGAACATTATGATC/3BioTEG/ | 67.7 |
| SD60 | CTCTCTCTCTCCTCTCTCTCCGCCCAAATAAGAACATTATGATCA/3BioTEG/ | 59.7 |
| SD61 | CTCTCTCTCTCCTCTCTCTCGCCCAAATAAGAACATTATGATCAG/3BioTEG/ | 65.6 |
| SD62 | CTCTCTCTCTCCTCTCTCTCCCCAAATAAGAACATTATGATCAGT/3BioTEG/ | 66.5 |
| SD63 | CTCTCTCTCTCCTCTCTCTCCCAAATAAGAACATTATGATCAGTA/3BioTEG/ | 63.8 |
| SD64 | CTCTCTCTCTCCTCTCTCTCCAAATAAGAACATTATGATCAGTAG/3BioTEG/ | 70.6 |

Figure 29:
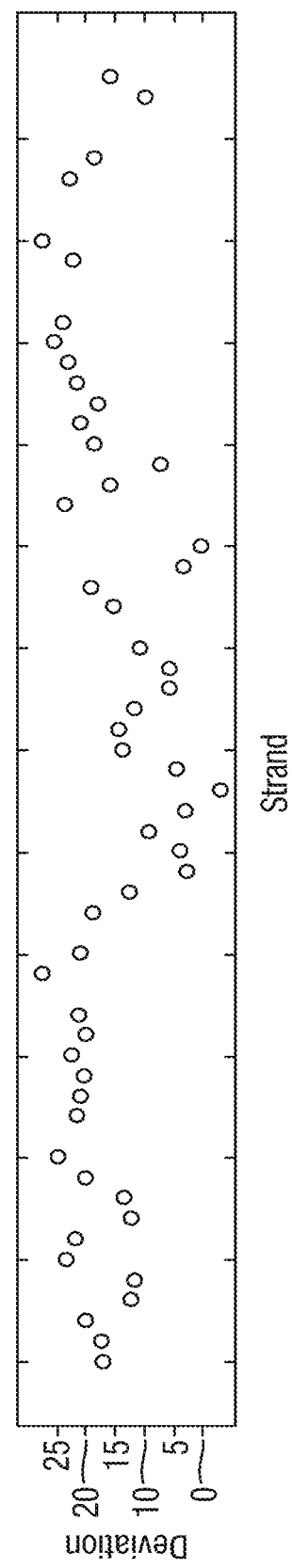
FIG. 29 is a scatter plot of current measurements obtained from DNA strands held in a MS-(B2)8 nanopore using streptavidin.

The data from each individual strand was plotted sequentially to produce a map of the current states (a scatter plot) as shown in FIG. 29, wherein each point represents a DNA strand from SD01 (left), to SD64 (right)). The data is plotted as the deflection from a PolyT strand.

These measurements may be used to derive the emission weightings 15 as distributions for each k-mer centred on the measurements shown in FIG. 29. Gaussian distributions may be used with a standard deviation obtained from the measurements shown in FIG. 29. The transition weightings 14 may be selected manually.

The second dynamic training method is performed as follows.

Static strand training provides many advantages, however it can be laborious and also for some measurement systems might not accurately reflect the complete sequencing system. The model 13 can alternatively be trained by exploiting a similar framework (and therefore similar algorithms) to those we use in analysis step S2. One such implementation of this is now described, although many variations can be applied. Since the process described is an iterative one, it is useful to have a reasonable estimate of the parameters to begin with (in Bayesian terms, a prior). The 3-mer static coefficients provide a reasonable starting point for training higher k-mer models.

Since training is applied, a model is used with considerably less flexibility than the state calling model. A major constraint can be applied since the sequence of the training strand(s) is known. Rather than modelling the allowed transitions between all k-mers, only those transitions allowed by our training sequence are modelled. To further constrain the training, each position in the training strand is modelled independently and only transitions to the immediately following states are preferred. Hence we could call this a "forced path" model.

Figure 30:
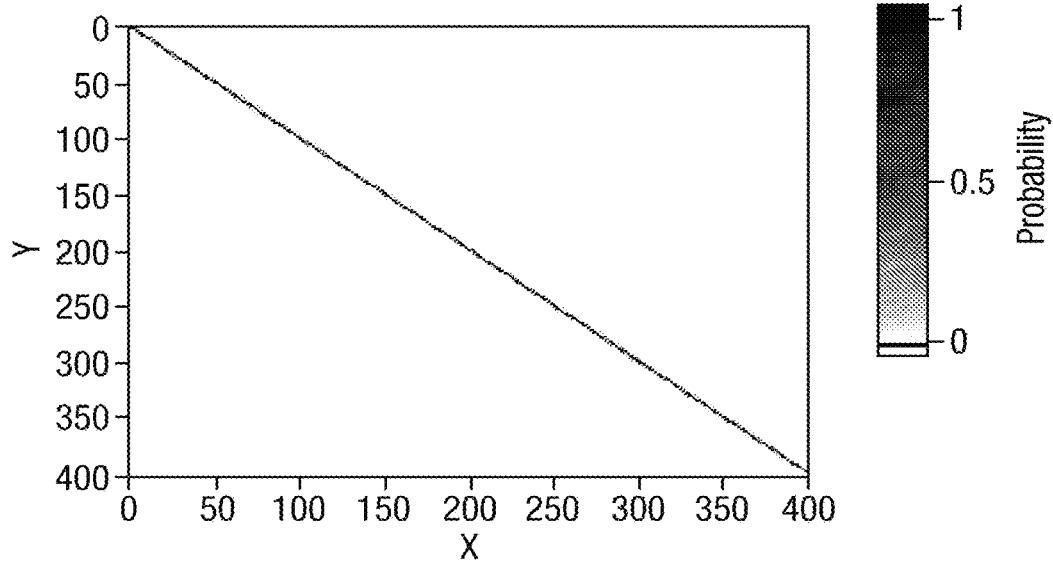
FIG. 30 is a transition matrix for an example training process.
Figure 31:
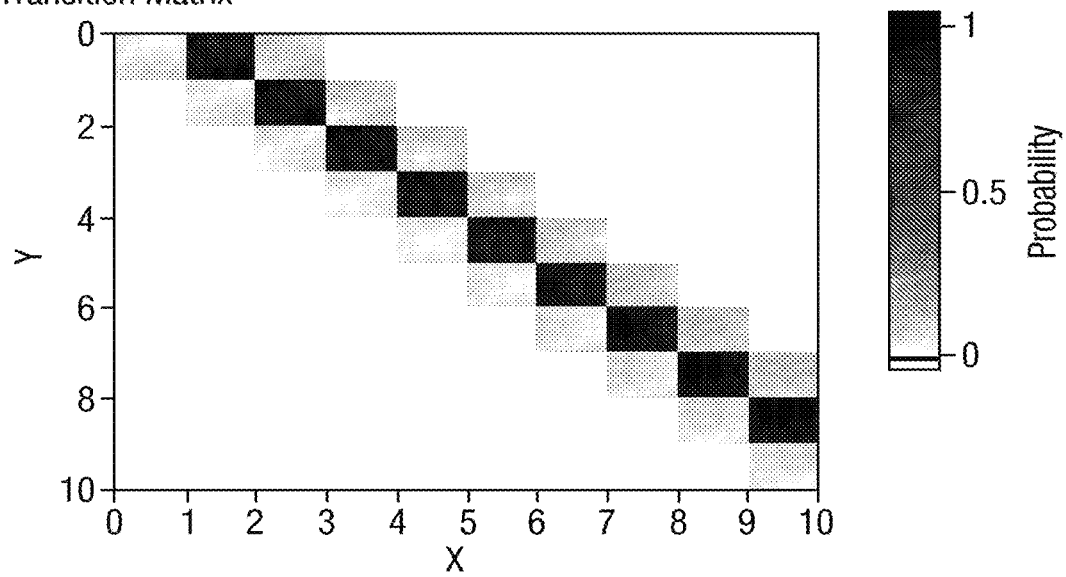
FIG. 31 is an enlarged portion of the transition matrix of FIG. 30.

Given a polymer of approx. 400 units, for example, a separate state index for each position in that polymer can be defined. A transition matrix is then constructed that allows transitions within the polymer, as shown in FIGS. 30 and 31, FIG. 30 showing a transition matrix for 408 k-mer states and FIG. 31 showing a close-up of the first 10 transition weightings.

As with the k-mer estimation transition matrix of transition weightings 14 in the model 13 described above, flexibility can be added to allow for the fact that this is a real-world system. In this example, the absence of a transition (or a transition in which the origin state index and destination state index are the same state) is permitted, and a missed measurement is accommodated by using non-zero probabilities for non-preferred transitions that skip a state. An advantage of the probabilistic (or weighted) framework is that known artefacts of the measurement system can be specifically handled in the transition weightings and/or the emission weightings.

Figure 32:
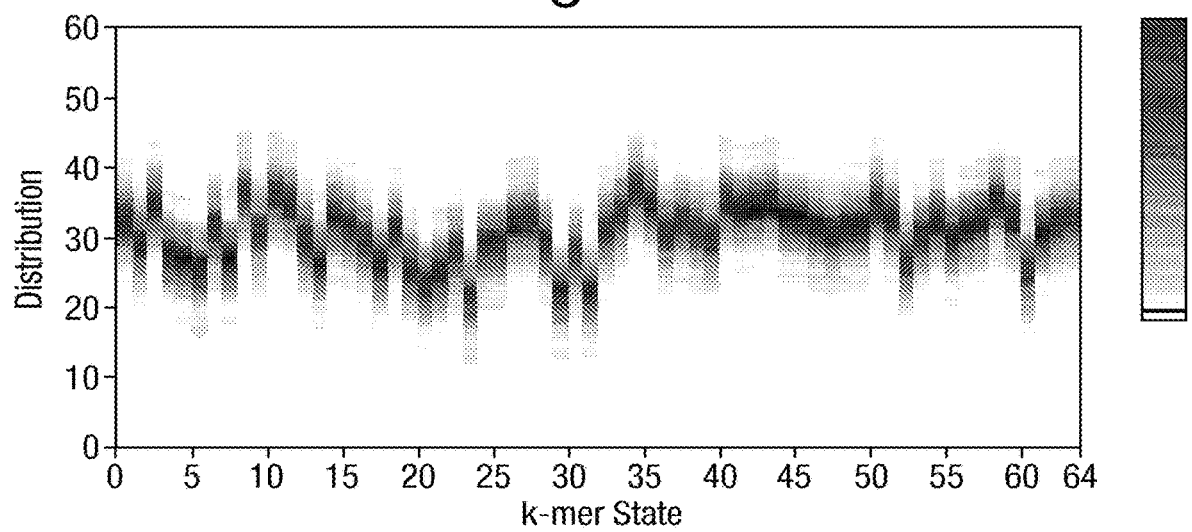
FIGS. 32 and 33 are graphs of emission weightings for, respectively, a model of 64 k-mers derived from a static training process and a translation of that model into a model of approximately 400 states.
Figure 33:
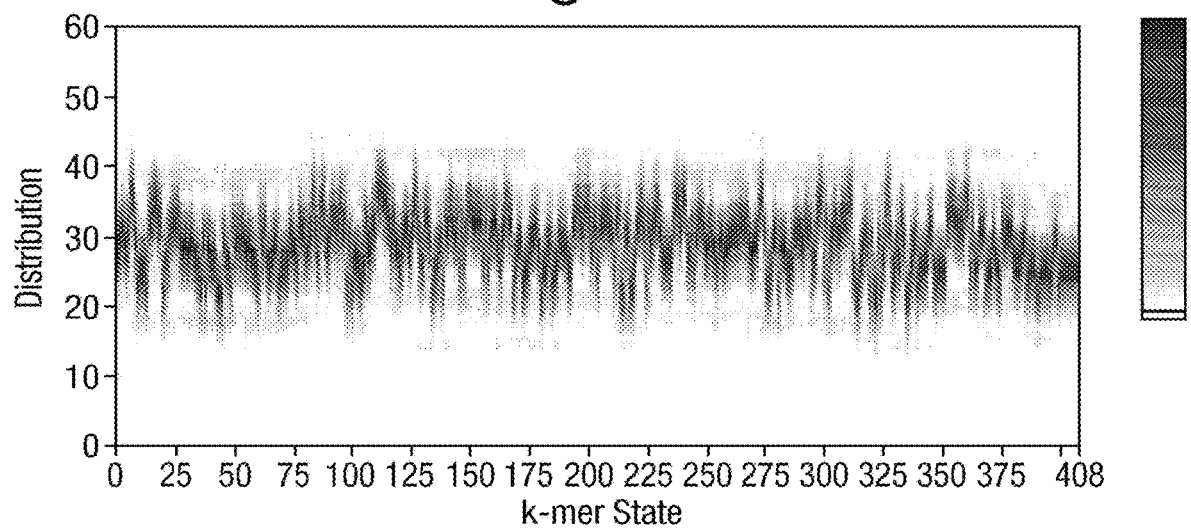

The training of the emission weightings is now described. The distributions of the emission weightings can be similar to those used for the analysis step S2 described above. However since, in this example, each position in the polymer is dealt with separately an emission distribution is defined for each position. FIG. 32 shows an example of a 64 k-mer model derived from a static training process as described above. FIG. 33 shows an example of the 64 k-mer model of FIG. 32 translated into a sequence of approximately 400 states. As described previously, outlier data can be accommodated within the distributions of the emission weightings having a non-zero probability for all possible measurement values.

Figure 34:
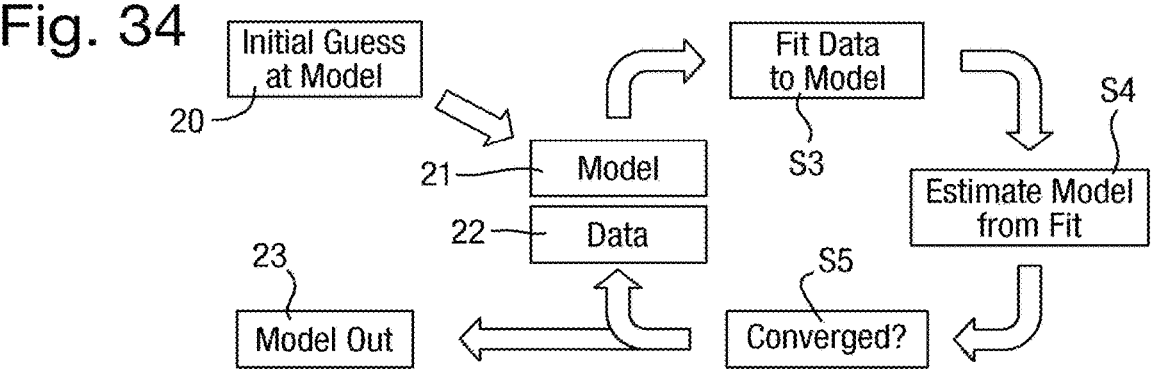
FIG. 34 is a flow chart of a training process.

The training process is shown in FIG. 34 and is now described. The training process is iterative and first uses the initial estimate of the model 20, as described above, as an estimate of the model 21. The training process also uses the measurements 22.

Given the estimate of the model 21 and the measurements 22, in step S3 it is calculated how the measurements 22 fit to the model by applying any one of a range of known algorithms. In the case of an HMM, one suitable algorithm is the Forwards-Backwards algorithm.

In step S4, the data fit to the model calculated in step S3 is then used to estimate what the underlying state emission distribution would be under that fit and to re-estimate the k-mer state centres, thereby to update the estimate of the model 21.

In step S5, it is determined if the training process has converged, i.e. if the updated estimate of the model 21 from step S4 has not changed significantly from the previous iteration. If not converged, the process is iterated using the updated estimate of the model 21.

Such iterations occur until convergence is determined in step S5. At this point, the updated estimate of the model 21 has converged to a description of the measurements 22 and is output as the output model 23.

Whilst this is one possible implementation of a machine learning algorithm for the training process, other machine learning methods as are known in the art could be used.

There will now be described an example of the analysis method of FIG. 6 being applied to the experimentally determined input signal 11 of FIG. 9. As described above, the series of measurements 12 derived by the state detection step S1 are shown in FIG. 10.

The polymer is a polynucleotide and the k-mer model used to describe the measurements is a 3-mer.

The model 13 comprises transition weightings 14 as shown in FIG. 16 and described above.

Figure 35:
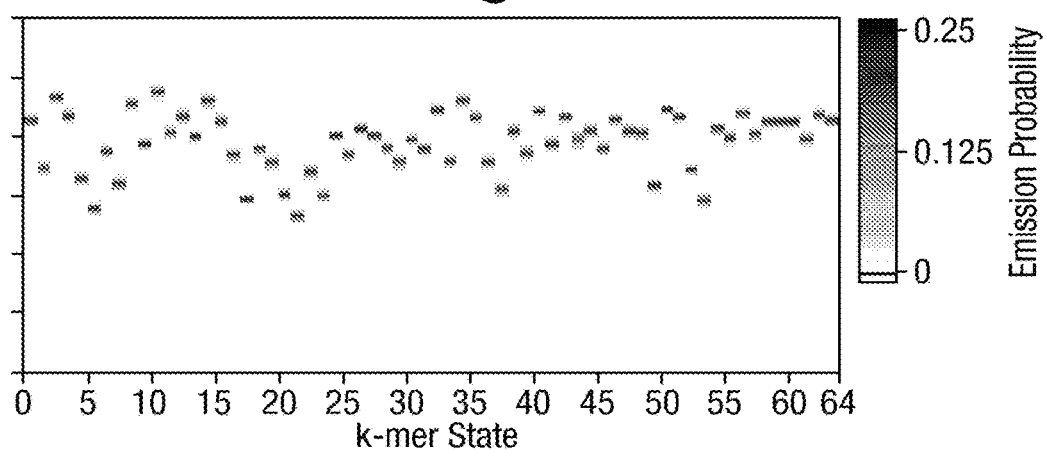
FIG. 35 is a graph of emission weightings determined by the training process of FIG. 34.

The model comprises emission weightings 15 determined using the training process of FIG. 34 as described above. FIG. 35 shows the resultant emission weightings 15 which are Gaussian distributions having a small non-zero background.

Figure 36:
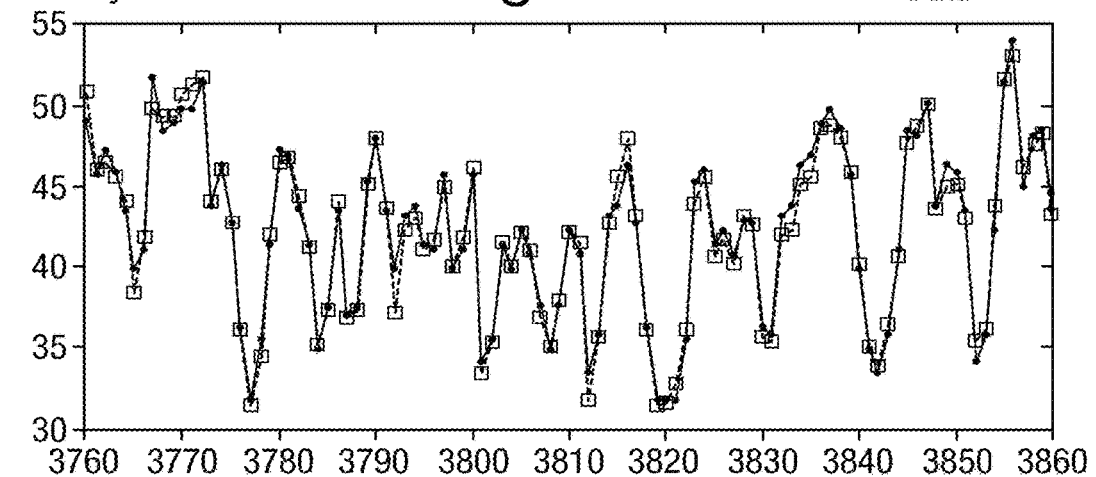
FIG. 36 is a graph of current measurements aggregated over several experiments with the expected measurements from a model.

FIG. 36 shows an overlay of current measurements from a section of state data, aggregated over several experiments, with the expected measurements from the model 13.

Figure 37:
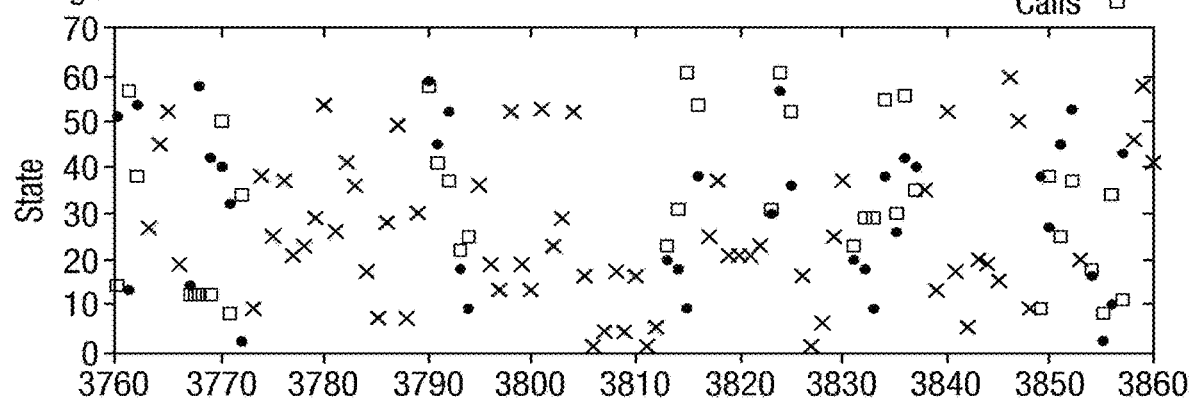
FIG. 37 is a graph of the k-mer space alignment between the actual k-mers and the estimated k-mers.

FIG. 37 shows the state space alignment of the known sequence (reference) and the estimated sequence of k-mer states estimated by the analysis step S2 (calls). Correctly estimated k-mer states are shown as large points. As can be seen, a good estimation of k-mer states is provided.

FIG. 38 shows the estimated sequence 16 of nucleotides estimated by the analysis step S2 and shown aligned with the actual sequence. Correct k-mer state estimates are illustrated as a '#' (since we have related k-mer state directly to base, this can be shown). Correct base estimates but incorrect k-mer state estimates are illustrated as a '*'.

The above description relates to the case that the method is based on a single input signal 11 and a single series of measurements 12.

Alternatively, the first aspect of the present invention may use plural series of measurements each related to the same polymer. In this context, the "same" polymer is a polymer having the same identity or composition, being physically the same polymer or being physically a different polymer having the same identity. The plural series of measurements may be made on the same polymer or may be made on different polymers having related sequences.

The plural series of measurements may each be made by the same technique or may be made by different techniques. The plural series of measurements may be made using the same or different measurement systems.

The plural series of measurements may be of different types made concurrently on the same region of the same polymer, for example being a trans-membrane current measurement and a FET measurement made at the same time, or being an optical measurement and an electrical measurement made at the same time (Heron A J et al., J Am Chem Soc. 2009; 131(5):1652-3). Multiple measurements can be made one after the other by translocating a given polymer or regions thereof through the pore more than once. These measurements can be the same measurement or different measurements and conducted under the same conditions, or under different conditions.

The plural series of measurements may be made on regions of polymers that are related. In this case, the series of measurements may be measurements of separate polymers having related sequences, or may be measurements of different regions of the same polymer having related sequences. As an example of the latter, there may be used techniques proposed for polynucleotides, where the relation is that sequences are complementary. In this case the sense and the antisense strand may be read sequentially using a polynucleotide binding protein or via polynucleotide sample preparation. Any method presented in Provisional Application 61/511,436 or WO-2010/086622 may be used to allow the sense and antisense strand to be read.

As an example of this, the method illustrated in FIG. 6 may be applied to plural input signals 11 that may be processed in the state detection step S1 to provide plural series of measurements 12. In this case, each input signal 11 and series of measurements 12 is related to said polymer, either by being measurements of the same region of the same polymer or by being measurements of different but related regions of the same or different polymers (e.g. a DNA strand and the complementary DNA strand), as described in detail above.

In this case, the analysis method is fundamentally the same, but the measurements from respective series of measurements 12 are treated by the analytical technique in step S2 as arranged in plural, respective dimensions.

This provides considerable advantage over processing each input signal 11 and series of measurements 12 separately in analysis step S2. By combining the information from the series of measurements 12 at this early stage in the analysis, it is possible to make a more accurate estimation of the underlying polymer units. The combination of information earlier in the analysis process enables a more accurate output than independent treatment of the series of measurements 12 and combination at the end of the analysis process. This may be achieved without any requirement that the series of measurements 12 are related, other than through the underlying polymer relation. The probabilistic or other analytical technique also enables the analysis to estimate registration or alignment of the related series of measurements 12. It is important to note that the registration of any series of measurements to any other might or might not be known a priori. In cases where there is no registration, then each measurement within a series is not a priori paired with a measurement from another series.

Mathematically speaking, the extension of the analysis step S2 to treat the series of measurements 12 as arranged in two respective dimensions is straightforward. The emission weightings 15 occur in plural dimensions, one dimension for each series of measurements 12. In the case that the method is performed on plural series of measurements 12 that are registered, so that it is known a priori which measurements from the respective series correspond and are dependent on the same k-mer, the model 13 may be applied using the emission weightings 15 as a probability density function in plural dimensions which describes the distribution of the plural measurements for each k-mer state.

In contrast, in the case that the method is performed on plural series that are not registered so that it is not known a priori which measurements from the respective series correspond and are dependent on the same k-mer, the method treats the plural series of measurements as a whole as arranged in plural, respective dimensions, as follows.

Each dimension of the emission distribution is augmented with a skip state, with multidimensional weights representing their chance of occurrence. Where skips occur in individual series, the emission distribution is taken to emit a "skip" signal state rather than a measurement value in the corresponding dimension. These "skip" states are not observable, and the unknown number and location of these states causes registration problems. The analysis step S2 is performed based on the likelihood of the plural series of measurements 12 being derived from different sequences of k-mers and polymer units and with different registrations between those measurements, the chance of each registration being implicit in the emission distribution.

In both the registered and unregistered cases, where the plural series of measurements 12 are equivalent measurements of the same property (e.g. for repeated measurement of the same polymer) the emission weightings 15 in respect of each series 12 may be identical. Where the plural series of measurements 12 are measurements of the different properties (e.g. for different measurement of the same polymer, or for measurements of different, but related regions of a polymer) the emission weightings 15 in respect of each series 12 may be different.

Considering graphical model B above, conceptually the model is the same except that $X_i$ now represents a vector of values rather than a single value. In the case of an HMM, rather than a state emitting values from a one-dimensional probability density function g( ), values are emitted from a plural dimensional density function, for example in the case of measurements of a sense and antisense strand, $X_i$ emits a current pair $(x_{is}, x_{ia})$ where $x_{is}$ is the current read from the sense strand and $x_{ia}$ is the reading from the antisense strand for the complementary k-mer. This emitted current pair may contain unobserved skip states as well as real current measurements. Just as in the basic one-dimensional case, outliers and missing data, or skipped states, can be modelled.

Advantageously, skips in one of the polymers may be bridged using information from the related polymer. For example, with sense-antisense data, a skip may be emitted in sense but not antisense (or vice-versa) by allowing the two dimensional density g( ) to emit a skip in one dimension with non-zero probability while sampling a current from the other dimension, so $X_1$ may emit current pairs of the form $(x_{1s}, x_{1a})$, $(x_{1s},-)$ or $(-,x_{1a})$ where - represents an unobserved skip. In addition skips in both polymers can also be modelled and corrected for as in the 1D case. Here, "stays" in one series of measurements may also be modelled by emitting skip states for the others.

All the advantages from the one dimensional HMM transfer to this plural dimensional HMM. There is similarly an advantage over running two separate one-dimensional HMMs and then aligning in base space through alignment techniques.

Merely by way of example an application of the Viterbi algorithm to measurements arranged in plural dimensions will be discussed. The Viterbi algorithm is well known in the art. For a one-dimensional HMM, the likelihood $L_i(k)$ of the most likely path ending in each possible k-mer K is calculated for each state i moving forwards through the state sequence from the first to the last state (i=1 . . . n). All such paths must be considered because of the lack of registration between the plural series of measurements. The values $L_i(K)$ can be calculated using only the values $L_{i-1}(.)$ from the immediately preceding state along with the transition and emission probabilities, forming a recursion. In an m-dimensional HMM, a similar scheme may be used. If skips are to be incorporated, then we have m indices, so $L_{i1,i2,\ldots,im}(K)$ is the maximum likelihood describing state i1 in dimension 1, state i2 in dimension 2 and so on. It may be calculated recursively by looking at all possible quantities $L_{j1,j2,\ldots,jm}(K)$ where j1=i1 if a skip is emitted in dimension 1 or (i1−1) if a state is emitted in dimension 1—similarly for j2, j3 etc.

This analysis method may be applied where each input signal 11 and series of measurements 12 are measurements of the same region of the same polymer. For example, in a system where the polymer, or regions of the polymer, are re-read, these readings can be combined and the registration or alignment estimated to make a more accurate determination of the underlying k-mer state. The method also allows measurements made under different conditions or by different methods to be combined.

As discussed above multiple measurements may also be made concurrently, for example, where the multiple series of measurements comprise multiple electrical measurements or an electrical and an optical measurement. These readings can be combined and/or the registration or alignment estimated to make a more accurate estimation of the underlying polymer sequence.

Alternatively, plural series of measurements 12 are aggregated to provide a summary series of measurements, that is used by the analysis step S2 as one-dimensional measurements. Where there are multiple measurement series' of m different types, aggregation may be applied to all series' of the same type, and an m-dimensional HMM employed on the summary state series'. Alternatively, where there are multiple series', a one-dimensional HMM may be run on each series, or on each summary measurement series, and a consensus call made based on the output from these analyses.

This analysis method may also be applied to input signals 11 and series of measurements 12 that comprise two series of measurements, wherein the first series of measurements are measurements of a first region of a polymer and the second series of measurements are measurements of a second region of a polymer that is related to said first region, for example complementary regions of the same or different polymers.

This technique has particular application to a complementary pair of DNA sequences, that is the "sense" strand and its complementary "antisense" strand.

The advantage of a two dimensional approach over two separate one-dimensional HMMs and then aligning in base space through alignment techniques will now be illustrated.

As a simplistic illustration, it is supposed that Pr(AAACAAA)=0.6, Pr(AAAGAAA)=0.39, Pr(AAAAAAA)=0.01 from an HMM on the sense strand, and that Pr(TTTTTTT)=0.6, Pr(TTTCTTT)=0.39, Pr(TTTGTT)=0.01 from an HMM on the antisense strand. If the most likely sequences for sense and antisense are taken and attempted to be aligned as a sense-antisense pair, then a clash is obtained at the middle base of the sequence. A 2-dimensional HMM would find that by far the most likely consistent pair of sequences was (AAAGAAA,TTTCTTT), and would assign low probabilities to the sequence pairs (AAACAAA,TTTGTTT) and (AAAAAAA,TTTTTTT).

While in this simplistic illustration, the second most likely sequences may be considered by each one-dimensional HMM to resolve the problem, it quickly becomes unrealistic to look through all necessary polymer unit estimations for longer sequences. Also, some methods for estimating polymer units (for instance Viterbi) only emit the most probable path, making combination of less likely sequences after estimating polymer units impossible.

A specific detailed example of the sense-antisense case using the Viterbi algorithm is now explained to demonstrate the improvement.

In the case of sense-antisense, the m-dimensional case described above is used for m=2 and $L_{i,j}(K)$ is calculated using the values $L_{i-1,j}(.)$, $L_{i,j-1}(.)$ and $L_{i,j}(.)$ depending on whether a state is emitted by sense only, by antisense only, or by both.

FIG. 39 illustrates an example in which independent calls of the most likely sense and antisense sequences are made using a 3-mer model and an HMM. A joint sense-antisense call is made using a two-dimensional Viterbi algorithm as described above. The joint call is correct with a very few exceptions, and in particular calls bases correctly that are called incorrectly in both the sense and antisense calls. Correct 3-mer state estimates are shown with a '#', correct bases with a '*'. It can be seen in this illustration that combining the best regions of the independent sense and antisense reads does not account for the number of correct calls in the sense-antisense result. The combination of data early in the analysis process, combined with a probabilistic approach leads to a "more than the sum of the parts" result.

Although this multi-dimensional example is for the case of sense-antisense DNA where the information added is that one strand is complementary to another, other relations between regions of polymers may be coded for in the multi-dimensional approach. An example of another type of information that could be coded for is structural information in polymers. This information may exist in RNA, which is known to form functional structures. This information may also exist in polypeptides (proteins). In the case of proteins the structural information may be related to hydrophobic or hydrophilic regions. The information may also be about alpha helical, beta sheet or other secondary structures. The information may be about known functional motifs such as binding sites, catalytic sites and other motifs.

There will now be discussed a method of making measurements of a polymer in accordance with the second aspect and third aspect of the invention. As discussed in more detail below, this may optionally be combined with the method described above in accordance with the first aspect of the invention.

In this method, the measurements are measurements of the ion current flowing through the nanopore. In this method, a polymer is translocated through a nanopore while a voltage is applied across the nanopore. The measurements are dependent on the identify of the k-mer in the nanopore. The measurements are made under the application of different levels of voltage across the nanopore. It has been appreciated by the present inventors that such measurements provide additional information, rather than being merely duplicative. Some specific demonstrations of this advantage will now be described.

A first example illustrates the resolution of ion current measurements of polymers that are strands of DNA held static in a measurement system under an applied potential. In this example, DNA sequences that are similar in current to each other at a first, normal level of voltage were resolved by recording at a second level of voltage.

DNA strands held in a nanopore using a streptavidin anchor similar to methods previously reported in Proc Natl Acad Sci USA. 2009 May 12; 106(19):7702-7. Runs were collected where individual strands of DNA were measured in a single MS-(B1)$_8$ nanopore embedded in a DPhPC bilayer using methods known in the art. A voltage was applied across the nanopore and a current was generated from the movement of ions in a salt solution on either side of the nanopore.

Run conditions were: 400 mM KCl, 10 nM Hepes, pH 8.0, +180 mV. A control sequence (TS01) was incubated with streptavidin in a 2:1 ratio and added to the chamber to give a final concentration of 200 nM DNA. The analyte sequence was added to the chamber in a 2:1 ratio with streptavidin to yield a final analyte DNA concentration of 400 nM. In both cases, the biotinylated DNA and the streptavidin were incubated for 5 minutes prior to addition into the chamber. Single channel recordings were performed using an automated procedure to change the applied potential between +180 mV (2 seconds) and −180 mV (0.2 seconds). The positive applied potential was used to capture and read the DNA level, whereas the negative potential was used to eject the streptavidin-DNA complex from the nanopore.

The mean current levels for each DNA binding event (state) were studied as follows.

The populations from the TS01 control and the analyte sequence were recorded. The analyte sequence current level was adjusted by using the following relationship:

$$I_{DNA\ Adjusted} = I_{DNA\ Recorded} - I_{TS01} \pm 32.2\ pA$$

This process was repeated for a range of different DNA sequences. By way of example, Table 2 sets out selected sequences where the adjusted current level showed a similar magnitude (54.5±0.5 pA) when measured at a voltage of +180 mV:

TABLE 2

| Code | Sequence | Triplet | Current (pA) |
|------|----------|---------|--------------|
| TS01 | TTTTTTTTTTTTTTTTTTTTTTTTTTTTTTTTTTTTTTTT/3BioTEG/ | Control | 28.5-33.3 |
| SD90 | CTCTCTCTCTCCTCTCTCTCGACGAGCACCAGAACAAAGGTCGTA/3BioTEG/ | ACA | 54.6 |
| SD85 | TTTTTTTTTTTTTTTTTTTTGCCCGGACGAGCACCAGAACAAAGG/3BioTEG/ | CCA | 55.0 |
| SD81 | CTCTCTCTCTCCTCTCTCTCGGGCGCCCGGACGAGCACCAGAACA/3BioTEG/ | AGC | 54.9 |
| SD59 | CTCTCTCTCTCCTCTCTCTCGCGCCCAAATAAGAACATTATGATC/3BioTEG/ | AAC | 54.0 |
| SD52 | CTCTCTCTCTCCTCTCTCTCCGTCCGGGCGCCCAAATAAGAACAT/3BioTEG/ | AAA | 54.7 |

TABLE 2-continued

| Code | Sequence | Triplet | Current (pA) |
|---|---|---|---|
| SD18 | CTCTCTCTCTCCTCTCTCTCAGTAGGAGCACTACGACCTTTGT/3BioTEG/ | TAC | 54.2 |
| SD15 | CTCTCTCTCTCCTCTCTCTGATCAGTAGGAGCACTACGACCTT/3BioTEG/ | CAC | 54.6 |
| SD03 | CTCTCTCTCTCCTCTCTCTCATAAGAACATTATGATCAGTAGGAG/3BioTEG/ | GAT | 54.3 |
| S142 | CTCTCTCTCTCCTCTCTCTTTGGGCGCCCGGACGAGCACCAGA/3BioTEG/ | ACG | 54.7 |
| S117 | CTCTCTCTCTCCTCTCTCGCTCCTACTGATCATAATGTTCTTA/3BioTEG/ | ATA | 54.1 |
| S116 | CTCTCTCTCTCCTCTCTCTGCTCCTACTGATCATAATGTTCTT/3BioTEG/ | CAT | 54.3 |

In a subsequent experiment, the same strands of DNA were all placed in a chamber containing a single MS-(B1)$_8$ nanopore embedded in a lipid membrane. Conditions were similar to those above: 400 mM KCl, 10 mM Hepes, pH 8.0, +180 mV. All analyte sequences were added to the chamber in a 2:1 ratio with streptavidin with a final concentration of 200 nM DNA for each analyte DNA. TS01 was not added in this experiment. The biotinylated DNA and the streptavidin were incubated for 5 minutes prior to addition into the chamber.

To investigate the effect of applied potential on the DNA discrimination, the voltage was varied in this experiment. Single channel recordings were performed using an automated procedure to change the applied potential between +X (2 seconds) and −X (0.2 seconds), where X is 140 mV, 180 mV and 220 mV. Single channel data was recorded for approximately 30 minutes for each value of X.

Figure 40:
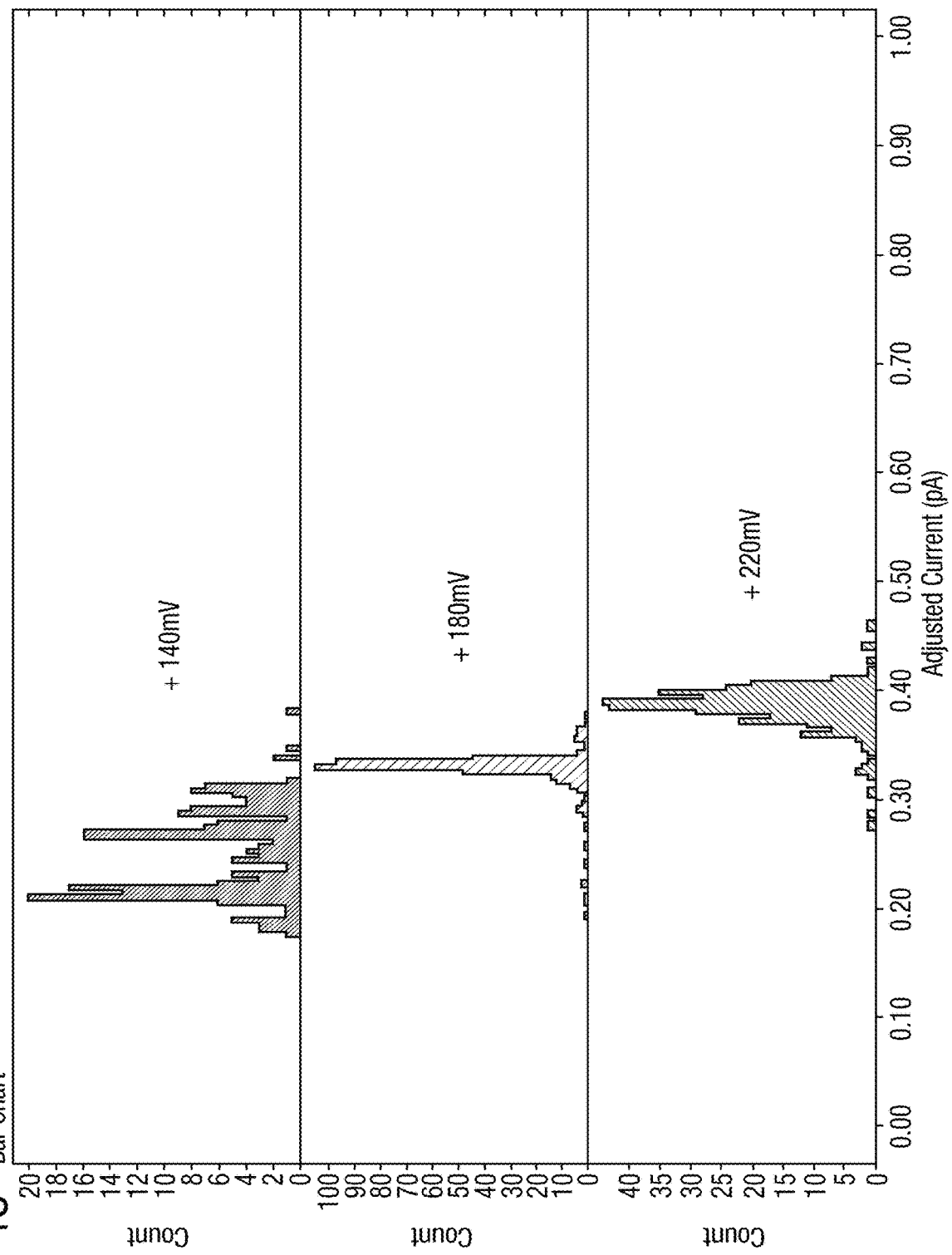
FIG. 40 is a set of histograms of ion current measurements for a set of DNA strands in a nanopore at three different voltages in a first example.

The mean current level for each DNA binding event (state) was recorded and plotted in are plotted in a set of histograms shown in FIG. 40 in respect of the positive potentials of +140 mV, +180 mV and +220 mV, respectively. Considering these results, it is clear that the data at +180 mV is behaving as expected with all of the eleven strands in Table 1.1 yielding a very similar current level. At +220 mV, there is a broadening or spread of the current level histogram suggesting that there has been a separation of levels. At +140 mV, there is also a broadening or spread and similarly the current levels have clearly resolved into a number of distinct populations. These results suggest that it would be possible to discriminate a number of the DNA strands from each other at +140 mV where it was not possible at +180 mV. Although for experimental ease this is an example performed with strands that are static in the nanopore, since the different DNA strand provide different k-mers at the relevant location in the nanopore to affect the ion current, it is expected that similar separation between ion currents generated by different k-mers of a DNA strand translocated dynamically through the pore.

A second example illustrates the separation of ion current measurements of polymers that are strands of DNA held static in a measurement system under an applied potential. In this example, measurements of ion current at different levels of voltage are shown to resolve different k-mers.

In the second example, to determine the effect of applied potential on the current levels of a given strand, a DNA sequence was chosen to contain all possible triplets (De Bruijn, GTAC, k3, Seq ID 5).

Seq ID 5 (k3 De Bruijn):
ATAAGAACATTATGATCAGTAGGAGCACTACGACCTTTGTTCTGGTGCTC
GTCCGGGCGCCCAAAT To evaluate the effects of the current levels without any possible complication from strand movement, a series of different DNA strands were designed. These each contained a biotin-TEG linker at the 3' end, a portion of the k3 De Bruijn sequence (35 nucleotides long), and a section with low secondary structure to aid threading of the DNA into the nanopore (10 nucleotides in length). The sequence of the section containing the k3 De Bruijn was varied so that the sequence was shifted by one nucleotide per strand. The leader section was chosen so that it did not hybridise to the De Bruijn section. These codes and corresponding sequences are listed in Table 3.

TABLE 3

| | | Current (pA) at varying applied potential | | | |
|---|---|---|---|---|---|
| Strand | Sequence | 180 mV | 140 mV | 100 mV | 60 mV |
| SD01 | CTCTCTCTCTCCTCTCTCTCAAATAAGAACATTATGATCAGTAGG/3BioTEG/ | 63.3 | 36.2 | 17.2 | 7.8 |
| SD02 | CTCTCTCTCTCCTCTCTCTCAATAAGAACATTATGATCAGTAGGA/3BioTEG/ | 72.6 | 41.3 | 20.1 | 4.9 |
| SD03 | CTCTCTCTCTCCTCTCTCTCATAAGAACATTATGATCAGTAGGAG/3BioTEG/ | 68.2 | 37.3 | 18.2 | 7.0 |
| SD04 | CTCTCTCTCTCCTCTCTCTCTAAGAACATTATGATCAGTAGGAGC/3BioTEG/ | 56.7 | 34.6 | 18.0 | 8.5 |
| SD05 | CTCTCTCTCTCCTCTCTCTCAAGAACATTATGATCAGTAGGAGCA/3BioTEG/ | 55.3 | 30.4 | 15.8 | 6.4 |
| SD06 | CTCTCTCTCTCCTCTCTCTCAGAACATTATGATCAGTAGGAGCAC/3BioTEG/ | 75.6 | 40.5 | 18.7 | 7.5 |
| SD07 | CTCTCTCTCTCCTCTCTCTCGAACATTATGATCAGTAGGAGCACT/3BioTEG/ | 69.0 | 40.6 | 19.9 | 8.0 |

TABLE 3-continued

| Strand | Sequence | Current (pA) at varying applied potential | | | |
|---|---|---|---|---|---|
| | | 180 mV | 140 mV | 100 mV | 60 mV |
| SD08 | CTCTCTCTCTCCTCTCTCTCAACATTATGATCAGTAGGAGCACTA/3BioTEG/ | 64.5 | 40.5 | 21.2 | 7.5 |
| SD09 | CTCTCTCTCTCCTCTCTCTCACATTATGATCAGTAGGAGCACTAC/3BioTEG/ | 57.8 | 31.9 | 17.6 | 7.6 |
| SD10 | CTCTCTCTCTCCTCTCTCTCCATTATGATCAGTAGGAGCACTACG/3BioTEG/ | 64.3 | 35.7 | 17.0 | 7.6 |
| SD11 | CTCTCTCTCTCCTCTCTCTCATTATGATCAGTAGGAGCACTACGA/3BioTEG/ | 80.4 | 47.0 | 22.5 | 6.3 |
| SD12 | CTCTCTCTCTCCTCTCTCTTATGATCAGTAGGAGCACTACGAC/3BioTEG/ | 77.5 | 47.0 | 24.8 | |
| SD13 | CTCTCTCTCTCCTCTCTCTATGATCAGTAGGAGCACTACGACC/3BioTEG/ | 65.3 | 41.2 | 23.2 | 10.2 |
| SD14 | CTCTCTCTCTCCTCTCTCTCATGATCAGTAGGAGCACTACGACCT/3BioTEG/ | 68.9 | 40.0 | 21.6 | 8.8 |
| SD15 | CTCTCTCTCTCCTCTCTCTCTGATCAGTAGGAGCACTACGACCTT/3BioTEG/ | 67.1 | 39.8 | 21.4 | 10.4 |
| SD16 | CTCTCTCTCTCCTCTCTCTCGATCAGTAGGAGCACTACGACCTTT/3BioTEG/ | 67.3 | 38.8 | 20.9 | 10.5 |
| SD17 | CTCTCTCTCTCCTCTCTCTCATCAGTAGGAGCACTACGACCTTTG/3BioTEG/ | 66.6 | 39.3 | 21.0 | 10.0 |
| SD18 | CTCTCTCTCTCCTCTCTCTCAGTAGGAGCACTACGACCTTTGT/3BioTEG/ | 77.7 | 44.7 | 22.1 | 7.0 |
| SD19 | CTCTCTCTCTCCTCTCTCTCCAGTAGGAGCACTACGACCTTTGTT/3BioTEG/ | 67.3 | 37.7 | 19.0 | 8.5 |
| SD20 | CTCTCTCTCTCCTCTCTCTCAGTAGGAGCACTACGACCTTTGTTC/3BioTEG/ | 71.6 | 41.3 | 20.0 | 7.8 |
| SD21 | CTCTCTCTCTCCTCTCTCTCGTAGGAGCACTACGACCTTTGTTCT/3BioTEG/ | 76.9 | 47.3 | 24.6 | 7.9 |
| SD22 | TTTTTTTTTTTTTTTTTTTTAGGAGCACTACGACCTTTGTTCTG/3BioTEG/ | 58.2 | 33.4 | 18.0 | 6.9 |
| SD23 | TTTTTTTTTTTTTTTTTTTAGGAGCACTACGACCTTTGTTCTGG/3BioTEG/ | 68.8 | 37.5 | 18.6 | 8.1 |
| SD24 | CTCTCTCTCTCCTCTCTCTCGGAGCACTACGACCTTTGTTCTGGT/3BioTEG/ | 57.7 | 34.4 | 17.1 | 7.4 |
| SD25 | CTCTCTCTCTCCTCTCTCTCGAGCACTACGACCTTTGTTCTGGTG/3BioTEG/ | 49.1 | 28.8 | 17.2 | 8.1 |
| SD26 | CTCTCTCTCTCCTCTCTCTCAGCACTACGACCTTTGTTCTGGTGC/3BioTEG/ | 50.4 | 25.8 | 13.5 | 7.9 |
| SD27 | CTCTCTCTCTCCTCTCTCTCGCACTACGACCTTTGTTCTGGTGCT/3BioTEG/ | 65.8 | 34.8 | 13.8 | 2.5 |
| SD28 | TTTTTTTTTTTTTTTTTTCACTACGACCTTTGTTCTGGTGCTC/3BioTEG/ | 50.3 | 28.9 | 14.2 | 5.7 |
| SD29 | TTTTTTTTTTTTTTTTTTTTACTACGACCTTTGTTCTGGTGCTCG/3BioTEG/ | 53.0 | 27.0 | 12.9 | 2.9 |
| SD30 | CTCTCTCTCTCCTCTCTCTCCTACGACCTTTGTTCTGGTGCTCGT/3BioTEG/ | 52.6 | 24.8 | 10.6 | 4.3 |
| SD31 | CTCTCTCTCTCCTCTCTCTCTACGACCTTTGTTCTGGTGCTCGTC/3BioTEG/ | 60.4 | 30.4 | 11.9 | 5.0 |
| SD32 | CTCTCTCTCTCCTCTCTCTCACGACCTTTGTTCTGGTGCTCGTCC/3BioTEG/ | 69.9 | 39.8 | 17.0 | 2.2 |
| SD33 | CTCTCTCTCTCCTCTCTCTCCGACCTTTGTTCTGGTGCTCGTCCG/3BioTEG/ | 59.5 | 34.3 | 17.0 | 5.6 |
| SD34 | CTCTCTCTCTCCTCTCTCTCGACCTTTGTTCTGGTGCTCGTCCGG/3BioTEG/ | 50.7 | 30.2 | 16.6 | 6.5 |
| SD35 | CTCTCTCTCTCCTCTCTCTCACCTTTGTTCTGGTGCTCGTCCGGG/3BioTEG/ | 50.5 | 27.6 | 14.6 | 5.9 |
| SD36 | CTCTCTCTCTCCTCTCTCTCCCTTTGTTCTGGTGCTCGTCCGGGC/3BioTEG/ | 57.1 | 29.9 | 14.9 | 7.0 |
| SD37 | CTCTCTCTCTCCTCTCTCTCCTTTGTTCTGGTGCTCGTCCGGGCG/3BioTEG/ | 67.6 | 37.4 | 17.2 | |
| SD38 | CTCTCTCTCTCCTCTCTCTCTTTGTTCTGGTGCTCGTCCGGGCGC/3BioTEG/ | 58.7 | 33.2 | 16.5 | 7.2 |
| SD39 | CTCTCTCTCTCCTCTCTCTCTTGTTCTGGTGCTCGTCCGGGCGCC/3BioTEG/ | 66.8 | 37.6 | 17.1 | 5.0 |
| SD40 | CTCTCTCTCTCCTCTCTCTCTGTTCTGGTGCTCGTCCGGGCGCCC/3BioTEG/ | 49.6 | 30.8 | 18.5 | |
| SD41 | CTCTCTCTCTCCTCTCTCTCGTTCTGGTGCTCGTCCGGGCGCCCA/3BioTEG/ | 58.7 | 30.1 | 14.0 | 5.9 |
| SD42 | CTCTCTCTCTCCTCTCTCTCTTCTGGTGCTCGTCCGGGCGCCCAA/3BioTEG/ | 57.3 | 26.9 | 11.8 | 6.5 |
| SD43 | CTCTCTCTCTCCTCTCTCTCTCTGGTGCTCGTCCGGGCGCCCAAA/3BioTEG/ | 69.4 | 37.1 | 14.6 | 5.4 |
| SD44 | CTCTCTCTCTCCTCTCTCTCCTGGTGCTCGTCCGGGCGCCCAAAT/3BioTEG/ | 57.0 | 35.2 | 15.7 | 4.3 |

TABLE 3-continued

| Strand | Sequence | Current (pA) at varying applied potential | | | |
|---|---|---|---|---|---|
| | | 180 mV | 140 mV | 100 mV | 60 mV |
| SD45 | CTCTCTCTCTCCTCTCTCTCTGGTGCTCGTCCGGGCGCCCAAATA/3BioTEG/ | 54.0 | 32.0 | 19.5 | 7.1 |
| SD46 | CTCTCTCTCTCCTCTCTCTCGGTGCTCGTCCGGGCGCCCAAATAA/3BioTEG/ | 65.3 | 34.9 | 17.2 | 8.1 |
| SD47 | CTCTCTCTCTCCTCTCTCTCGTGCTCGTCCGGGCGCCCAAATAAG/3BioTEG/ | 66.2 | 38.7 | 19.4 | 8.7 |
| SD48 | CTCTCTCTCTCCTCTCTCTCTGCTCGTCCGGGCGCCCAAATAAGA/3BioTEG/ | 61.3 | 36.7 | 20.1 | 9.2 |
| SD49 | CTCTCTCTCTCCTCTCTCTCGCTCGTCCGGGCGCCCAAATAAGAA/3BioTEG/ | 75.5 | 43.4 | 21.1 | 6.8 |
| SD50 | CTCTCTCTCTCCTCTCTCTCCTCGTCCGGGCGCCCAAATAAGAAC/3BioTEG/ | 69.4 | 39.0 | 19.6 | 8.9 |
| SD51 | CTCTCTCTCTCCTCTCTCTCGTCCGGGCGCCCAAATAAGAACA/3BioTEG/ | 74.5 | 44.2 | 21.6 | 8.8 |
| SD52 | CTCTCTCTCTCCTCTCTCTCCGTCCGGGCGCCCAAATAAGAACAT/3BioTEG/ | 71.6 | 42.8 | 22.9 | 9.1 |
| SD53 | CTCTCTCTCTCCTCTCTCTCGTCCGGGCGCCCAAATAAGAACATT/3BioTEG/ | 79.2 | 45.9 | 23.3 | 7.8 |
| SD54 | CTCTCTCTCTCCTCTCTCTCTCCGGGCGCCCAAATAAGAACATTA/3BioTEG/ | 58.5 | 34.4 | 18.7 | 8.3 |
| SD55 | CTCTCTCTCTCCTCTCTCTCCCGGGCGCCCAAATAAGAACATTAT/3BioTEG/ | 78.2 | 43.8 | 20.9 | 7.2 |
| SD56 | CTCTCTCTCTCCTCTCTCTCCGGGCGCCCAAATAAGAACATTATG/3BioTEG/ | 81.5 | 47.0 | 21.9 | 6.6 |
| SD57 | CTCTCTCTCTCCTCTCTCTCGGGCGCCCAAATAAGAACATTATGA/3BioTEG/ | 84.7 | 50.2 | 25.0 | 7.6 |
| SD58 | CTCTCTCTCTCCTCTCTCTCGGCGCCCAAATAAGAACATTATGAT/3BioTEG/ | 71.7 | 42.1 | 21.7 | |
| SD59 | CTCTCTCTCTCCTCTCTCTCGCGCCCAAATAAGAACATTATGATC/3BioTEG/ | 67.7 | 42.0 | 22.9 | 9.5 |
| SD60 | CTCTCTCTCTCCTCTCTCTCCGCCCAAATAAGAACATTATGATCA/3BioTEG/ | 59.7 | 34.2 | 19.1 | 8.6 |
| SD61 | CTCTCTCTCTCCTCTCTCTCGCCCAAATAAGAACATTATGATCAG/3BioTEG/ | 65.6 | 37.0 | 18.7 | 9.6 |
| SD62 | CTCTCTCTCTCCTCTCTCTCCCCAAATAAGAACATTATGATCAGT/3BioTEG/ | 66.5 | 39.8 | 21.3 | 9.2 |
| SD63 | CTCTCTCTCTCCTCTCTCTCCCAAATAAGAACATTATGATCAGTA/3BioTEG/ | 63.8 | 36.7 | 19.3 | 6.5 |
| SD64 | CTCTCTCTCTCCTCTCTCTCCAAATAAGAACATTATGATCAGTAG/3BioTEG/ | 70.6 | 38.0 | 17.4 | 6.1 |

The current levels of the strands showed in Table 3 were acquired using a similar approach to that described in the first example. The TS01 strand was added to the chamber as an internal control and the current levels were calibrated against this control. There were two main differences between the methods used in this experiment and those used in the first example. The first difference was that the nanopore was changed to the MS-(B1-L88N)$_8$ mutant. The second difference was the voltage scheme applied. This was chosen so that the current was recorded at four different applied potentials sequentially. As the rate that the nanopore captures DNA is dependent on the applied potential, the largest potential was recorded first. The voltage scheme chosen was: +180 mV (2.2 s), +140 mV (0.4 s), +100 mV (0.4 s), +60 mV (0.4 s), −180 mV (0.8 s).

Figure 41:
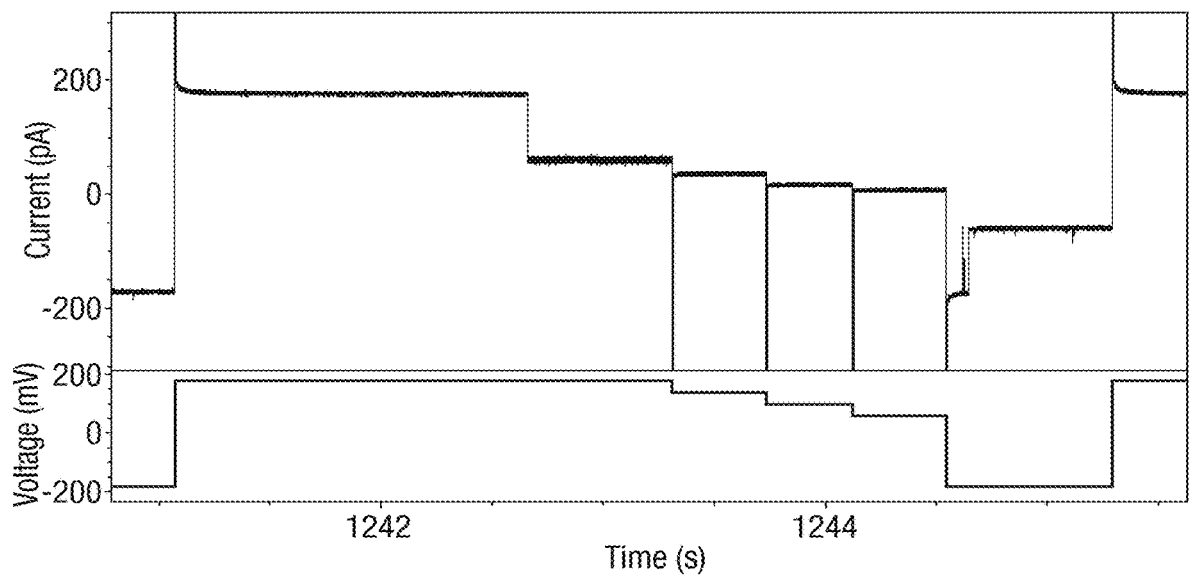
FIG. 41 is a pair of graphs of applied potential and resultant ion current over a common time period for a single strand in a nanopore in a second example.

FIG. 41 shows, in the lower trace, an example of the applied voltage and, in the upper trace, the resultant measured ion current for the SD01 strand over the same time scale. As can be seen in this example of FIG. 41, a binding event occurs during the initial period of +180 mV resulting in a drop in the ion current. As the potential is lowered in subsequent periods the observed ion current reduces. In the final period, the reversed voltage ejects the DNA strand.

A similar pattern is observed for all of the DNA strands SD01-SD54, the measured ion current levels at each voltage being listed in Table 3.

To provide a graphical representation of this data, FIGS. 42 to 45 are scatter plots of the measured current for each of the DNA strands sequentially indexed horizontally, at the four levels of voltage, respectively. As can be seen, the shape of the scatter plots change as the potential is varied. That implies that measurements at different voltages will provide additional information, for example by the measurement at one voltage providing resolution between two states that cannot be resolved at another voltage.

Figure 46:
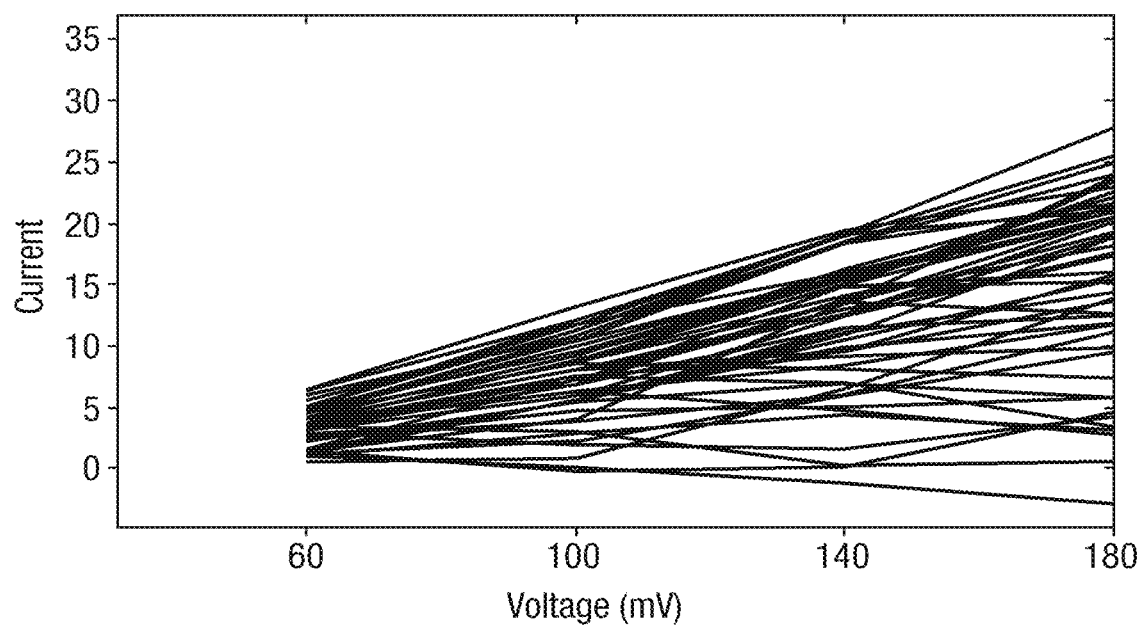
FIG. 46 is a plot of the measured current each DNA strand against the applied voltage in the second example.

To provide an alternative representation of the same data, FIG. 46 is a graph of the measured current of each strand against the applied voltages. The data consists of a point for each strand at each voltage, the points for each strand being joined by lines in the graph to show the trend for each strand. This representation in FIG. 46 illustrates two main features of the variation.

The first feature is that with increasing voltage overall there is an increase in the spread of measured current for the different stands. This overall trend is of general interest. It may be indicative of a change in the resolution between states that would affect the optimal choice of voltage, but that is dependent on the separation between states and also on the standard deviation of measurements of individual states. However, the overall trend is not what demonstrates the benefit of using plural voltages.

The second feature is that the measured current for individual strands show a behaviour with different dependencies on the applied voltage. Thus, even though the overall trend is a divergence with increasing voltages, the current measurements for each and every strand do not show the same trend. The measurements for strands do not mutually diverge, but instead there is variation for individual strands. Instead, whilst some strands exhibit a generally linear change with voltage, other strands exhibit a non-linear or fluctuating change, in some cases with points of inflection. The lines in respect of some strands converge, against the overall diverging trend. The reasons for this observation are not critical, but it is surmised that they caused by physical and/or biological changes in the measurement system under the application of different voltages, perhaps by conformational changes of the DNA in the nanopore.

This second feature demonstrates that measurements at more than one voltage provide additional information, rather than being merely duplicative. The ion current measurements at different voltages allow resolution of different states. For example, some states that cannot be resolved at one voltage can be resolved at another voltage.

Some additional observations on the second example examine the effect of changing the voltage on the on the standard deviation (or variance) of the states. The variance of these states may cause a problem when the variance of the current is on a similar timescale to the controlled movement of a DNA strand (such as enzyme controlled DNA translocation). In this regime, it becomes difficult to determine if a change in current level is due to variance within each state or a net movement of the DNA. For this reason, the data collected in second example was collected using strands held on top of the nanopore by streptavidin, rather than using an enzyme to control translocation. It is therefore desirable to have a system where the variance on a current level can be changed to delineate if the current change arose from a strand movement or an inherent property of that current state.

Figure 47:
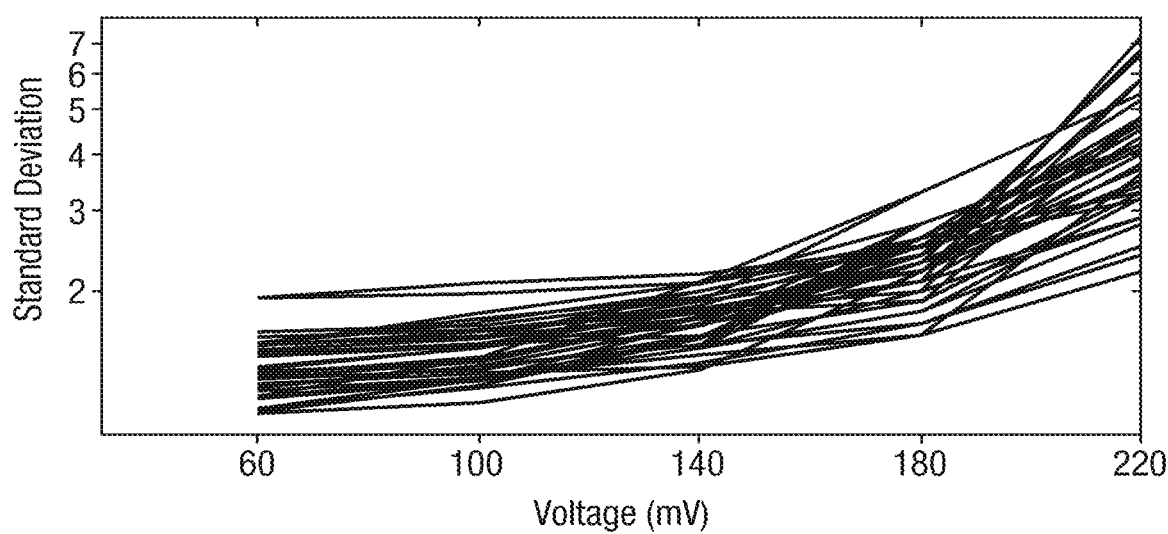
FIG. 47 is a plot of the standard deviation of the current measurements for each DNA strand in the second example against the applied voltage.

To assess the effect of applied potential on the state variance, the results of the second example were analysed to derive the average standard deviation for each of the DNA sequences in Table 3. FIG. 47 is a graph of the standard deviation of each strand against the applied voltages. The data consists of a point for each strand at each voltage, the points for each strand being joined by lines in the graph to show the trend for each strand. It is clear from FIG. 47 that the variance of the current level does change with applied potential. For the majority of strands, the variance increase with increased applied potential but rises steeply from +180 mV to +220 mV. It is surmised that this change has a similar cause to the variation in current with voltage mentioned above.

Figure 48:
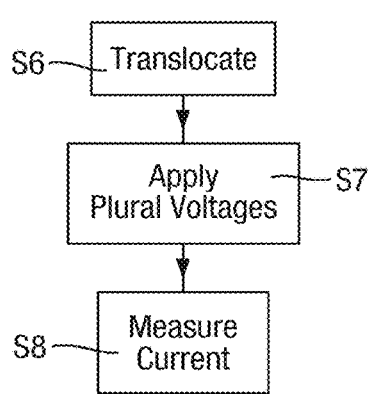
FIG. 48 is a flow chart of a method of making ion current measurements.

A method of making the ion current measurements at more than one voltage that embodies the second aspect and third aspect of the present invention is illustrated in FIG. 48. In this method, the applied potential is modulated while the DNA is moving through the nanopore.

In step S6, the polymer is translocated through a nanopore under the application of a voltage across the nanopore.

In step S7, during translocation, the level of the voltage is changed in a cycle. The cycle may include two or more voltage levels. The voltage levels may repeat in a regular or irregular pattern. The cycle, including its period, is selected to be shorter than the individual observed states, i.e. the states in which the polymer is different positions so that the measured current is dependent on different k-mers. Thus, it is observed that during each state, when the level of the voltage is the same, e.g. in repeated cycles, the ion current flowing through the nanopore is the same. In other words, the ion current is cycled with the applied voltage.

In step S8, the ion current flowing through the nanopore under the application of the different levels of voltage is measured for each respective state.

A third example with is an example of this method was performed as follows. An analyte DNA strand was chosen to contain the sequence that had been characterised with the streptavidin system in the second example above. The analyte DNA strand also contained a low secondary structure sequence at the 5' overhang to allow threading into the nanopore. A complementary strand was hybridised to the analyte strand. The complementary strand also contained a short 5' overhang where a short oligo containing a cholesterol-TEG linker was hybridised. The incorporation of the cholesterol allows the DNA to tether to the bilayer and greatly reduces the concentration of DNA required. Table 4 lists the sequences of the analyte DNA strands used in this example.

TABLE 4

| Strand | Sequence (5'-3') |
| --- | --- |
| I198 | TTTTTTTTTTTTTTTTTTTTTCCCCCCCCCCCCCAAATAAGAA CATTATGATCAGTAGGAGCACTACGACCTTTGTTCTGGTGCTC GTCCGGGCGCCCAAAGTGGAGCGAGTGCGAGAGGCGAGCGGTC AA |
| I305 | GTATCTCCATCGCTGTTGACCGCTCGCCTCTCGCACTCGCTCC ACTTTGGGCGCCCGGACGAGCACCAGAACAAAGGTCGTAGTGC TCCTACTGATCATAATGTTCTTATTT |
| TE07 | CAGCGATGGAGATAC-CholTEG |

The experimental setup was similar to described above with a solution containing: 400 mM KCl, 10 mM Hepes, pH 8.0, 1 mM EDTA, 1 mM DTT. The buffer was used in the chamber and as part of a pre-mix solution. The DNA used in Table 4.1 was hybridised in a 1:1:1 ratio and added to the premix solution, Phi29 DNAP was also added and the pre-mix was allowed to mix for 5 minutes at room temperature. A single MS-(B1-L88N)$_8$ channel was obtained and the premix added to give a final solution DNA concentration of 0.5 nM and a final solution Phi29 DNAP concentration of 100 nM.

The applied voltage was applied in a cycle comprising alternating pulses of +180 mV and +140 mV, each of length 10 ms.

Figure 49:
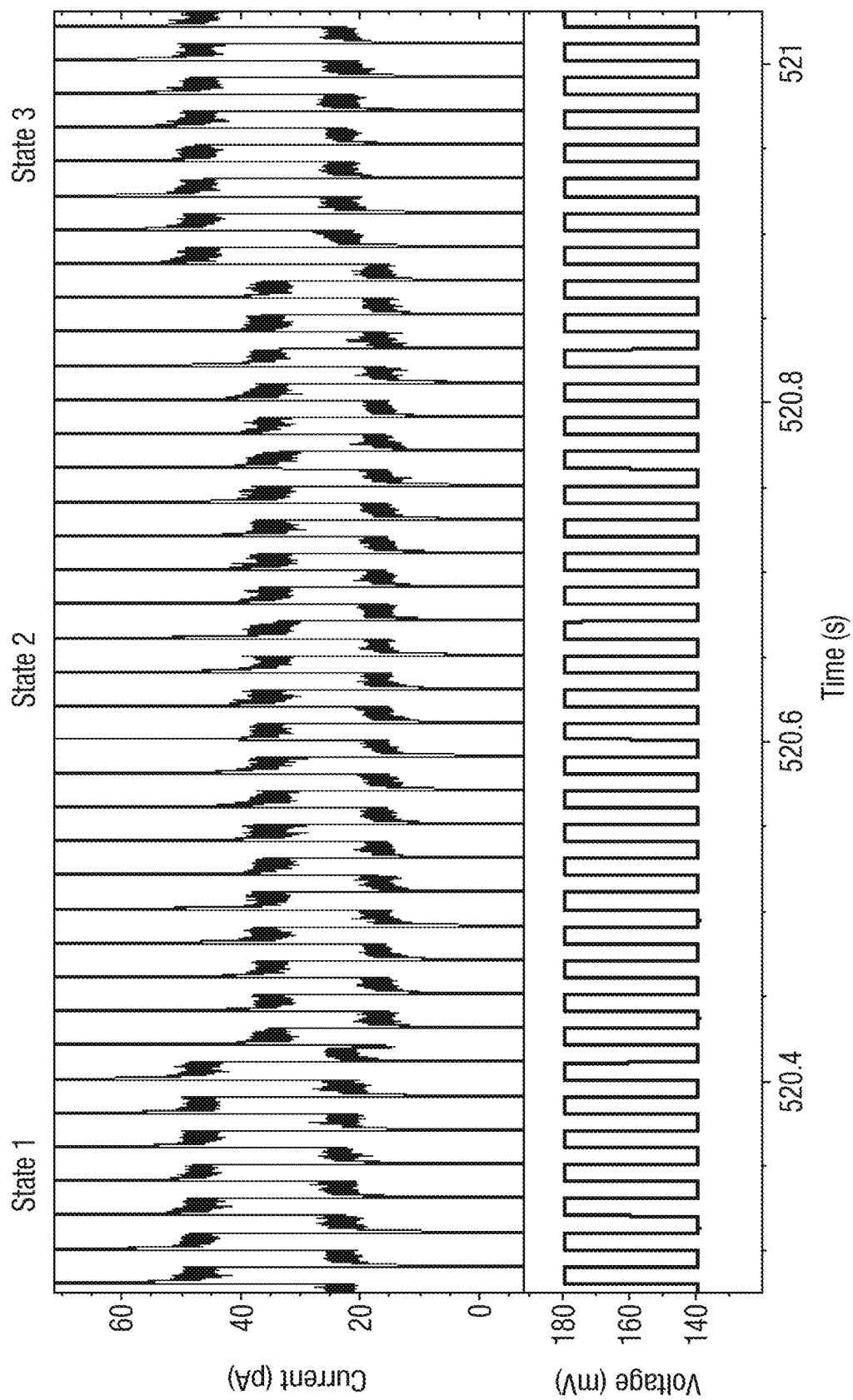
FIGS. 49 and 50 are each a pair of graphs of applied potential and resultant ion current over a common time period in a third example.

FIG. 49 shows an illustrative part of the results, showing in particular, in the lower trace, the applied voltage and in the upper trace the resultant measured ion current. Events were seen from Phi29 DNAP-DNA complexes. States could be observed at both of the applied potentials, for example labelled States 1 to 3 in FIG. 49. During each state, the ion current flowing at each level of the voltage in successive cycles is the same. In each state, current levels at an applied potential of +140 mV and +180 V are obtained sequentially while the strand is at a consistent position, giving reads at two voltages on the single molecule in the pore, this being achieved by the cycle period being shorter than the period of a state. A capacitive transient can be observed shortly after the applied potential is changed. This occurs when as the stored charge on the lipid bilayer changes. The duration of this capacitive transient is dependent on the size of the lipid membrane and can be reduced by going to a smaller membrane size. In this experiment, the lipid membrane was suspended across an aperture with a diameter of 50 μm.

It is also possible to observe the transitions between the states that occur when the strand moves from one position to another as the DNA is pulled through the Phi29 DNAP under the applied potential. The transition results in a change in the observed current for each of the applied potentials The example in FIG. 49 also illustrates the advantage of using plural voltages in that the difference between the measured ion currents in State 2 and the adjacent States 1 and 3 is much greater at the applied voltage of +180 mV than at the applied voltage of +140 mV. This makes it easier to resolve State 2 from States 1 and 3 at the applied voltage of +180 mV than at the applied voltage of +140 mV. Conversely, it is easier to resolve other states at the applied voltage of +140 mV than at the applied voltage of +180 mV.

Figure 50:
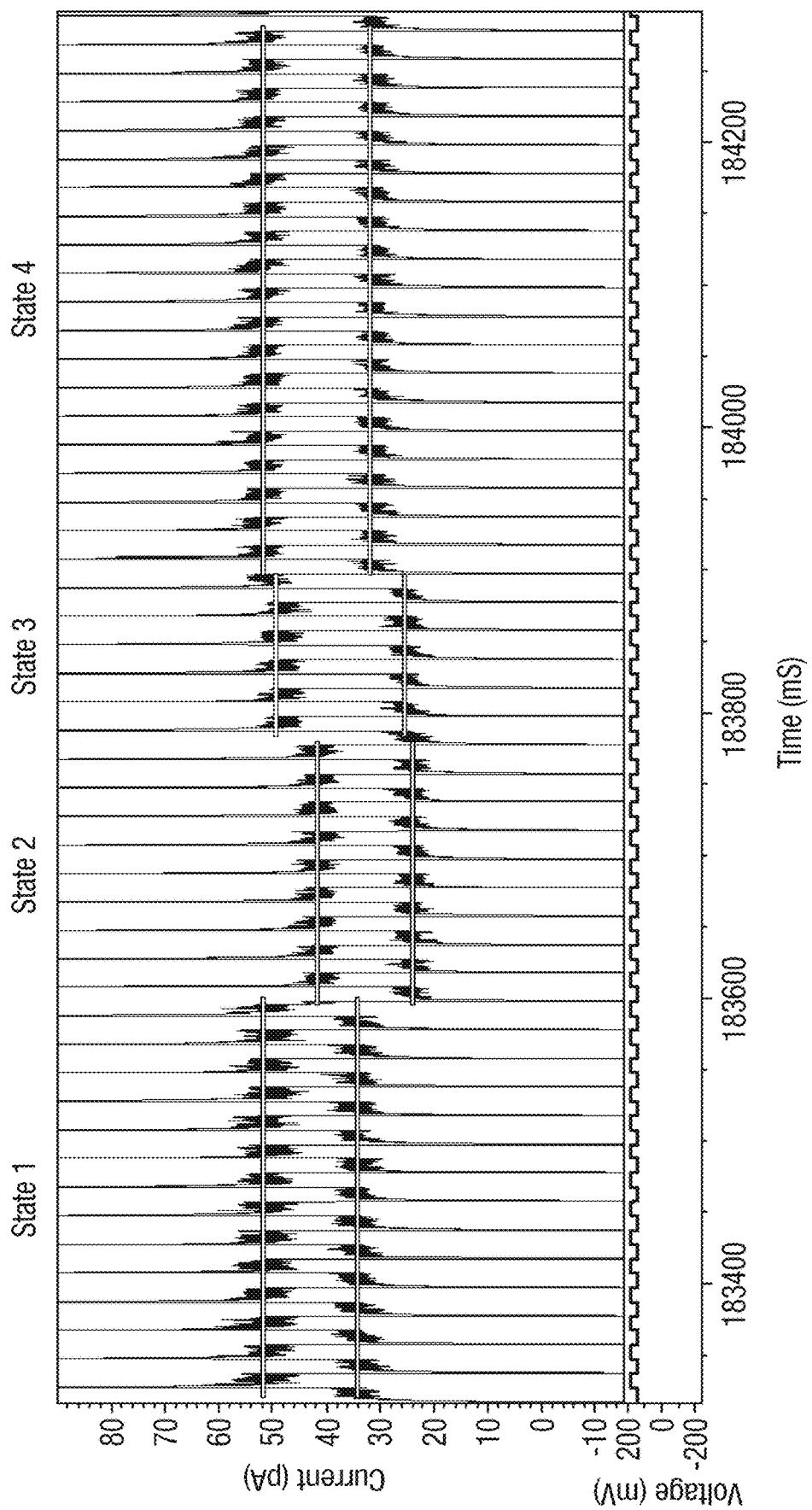

FIG. 50 illustrates another illustrative part of results acquired under similar conditions to those described in the third example, but using the MS-(B1)$_8$ pore instead of the MS-(B1-L88N)$_8$., in the same type of plot as FIG. 49. FIG. 50 has a similar overall form to FIG. 49, this time including four states labelled State 1 to State 4. In this case, there is almost no difference between the measured ion currents in State 2 and the adjacent State 3 at the applied voltage of +140 mV but a high difference at the applied voltage of +140 mV. In this case, it is difficult or even impossible to resolve State 2 from State 3 at +140 mV, but this becomes possible at +180 mV. Again, it is easier to resolve other states at the applied voltage of +140 mV than at the applied voltage of +180 mV.

The additional information obtained using plural levels of applied voltage demonstrated and discussed above provide advantages when the measured ion currents are analysed to derive information about the polymer.

One method of analysing the measurements is to apply a method in accordance with the first aspect of the present invention, for example the method described above that embodies the first aspect (with reference to FIG. 6 and subsequent drawings). Thus the various features of the methods described herein may be combined in any combination. In this case, the additional information obtained by using plural voltages improves the accuracy of the estimation.

The analysis method in accordance with the first aspect of the present invention determines the sequence, and hence the identity, of at least part of the polymer. However, the methods in accordance with the second aspect and third aspect also provide advantage in other methods of analysing the measurements that determine the identity of at least part of the polymer, some non-limitative examples of which are as follows.

The measurements may be analysed to estimate the sequence of polymer units in at least part of the polymer using techniques other than those accordance with the first aspect of the present invention.

The measurements may be analysed to estimate the identity of at least part of the polymer without providing a full estimate of the sequence of polymer units. In these types of analysis the additional information obtained by using plural voltages improves the accuracy of the estimation.

Alternatively, the measurements may be analysed to derive the timings of transitions between states. These timings are valuable in themselves, or may be used in further analysis, for example to determine the identity of polymer units. In this type of analysis, the additional information improves the ability to detect transitions. Some transitions are easier to observe at one potential and others are easier to observe at the other potential. By way of example, in the illustrative results of FIG. 50, the transition from State 2 to State 3 is difficult to observe at +140 mV, but is readily observed at +180 mV. In contrast, the transition from State 3 to State 4 is weak at +180 mV but easily observed at +140 mV. There is therefore clearly a benefit to the state detection in recording at more than one potential.

In some analysis methods, measurements at different levels are both used directly, for example as separate measurements that both contribute in the same manner to the determination of identity of at least part of the polymer. In other analysis methods, measurements at different levels may be used in different manners, for example the measurement made at one level being used to determine the identity and the measurements made at a different level being used to confirm the that result. Alternatively the noise at one level may be compared to the noise at another in order to make a decision to use a particular measurement at one voltage. Alternatively, the analysis method might involve selection between the measurements at different levels for the respective k-mers, followed by use of the selected measurements to determine the identity of at least part of the polymer.

It may be that the degree of additional information obtained by use of two measurements at different levels varies between k-mers. In that case, it may be that measurements at different numbers of levels are used for different k-mers, for example using measurements at a reduced number of levels, perhaps only a single level, for some k-mers, whilst using measurements at more levels for other k-mers. This method may be particularly useful for high variance states or for respective states having similar current levels.

Where measurements at different levels are used, different weightings may be attached to the different measurements.

Nonetheless, despite the fact that the analysis method might use the measurements in various ways, the measurements at different levels in respect of some k-mers are used in some manner.

There are now described two non-limiting examples in accordance with the present invention. Both these examples are applied to the case where there is typically at least one measurement per state at each potential.

In the first example the measurements at multiple levels are used to determine state transitions. This takes advantage of the fact that state transitions may be observable at one potential but not at another. The measurements may be subjected to the analysis method as described above including state detection step S1, where the chance of a transition from a state is high. In FIG. 50 the trace may be reduced to two measurements at respectively 140 and 180 mV by taking for example the average of the total data at each potential for a state. These measurements may then be treated as concurrent (i.e. tightly coupled dimensions) from two sets of emission distributions and analysed with a similar set of transitions to the 1D case. Note that this is similar in implementation to the case where we make more than one measurement of a state at a single potential for example mean and variance. Indeed we may extend this approach to four tightly coupled dimensions by considering for example the mean and variance at each potential.

In the second example the transitions between states are estimated during the analysis phase, rather than as a separate step, analogous to the case described above, where step S1 is omitted. In this example, for simplicity, we will consider the case where we have reduced the series of measurements at each step of the potential cycle to a single measurement, for example the mean. Again with reference to FIG. 50, state 1 consists of 28 measurements alternating between 140 and 180 mV. The emission probability for each measurement is therefore calculated with respect to the appropriate emissions (140 mV or 180 mV) and the transitions appropriate for this data. For example a total transition probability from this state of approx 0.05 may be appropriate. This approach may also be generalised to consider each measurement, rather than the summary measurement from each cycle, or plural summary measurements from each cycle.

In the method of making measurements at different voltages in accordance with the second aspect of the present invention, although it is advantageous to apply a method in accordance with the third aspect of the invention, in which the applied potential is cycled while the polymer is translocated through the nanopore, other methods may be used instead.

Figure 51:
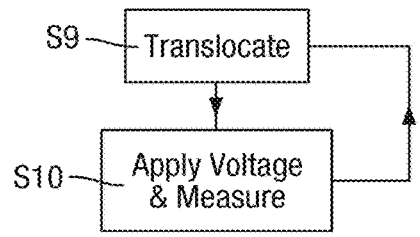
FIG. 51 is a is a flow chart of an alternative method of making ion current measurements.
Figure 42:
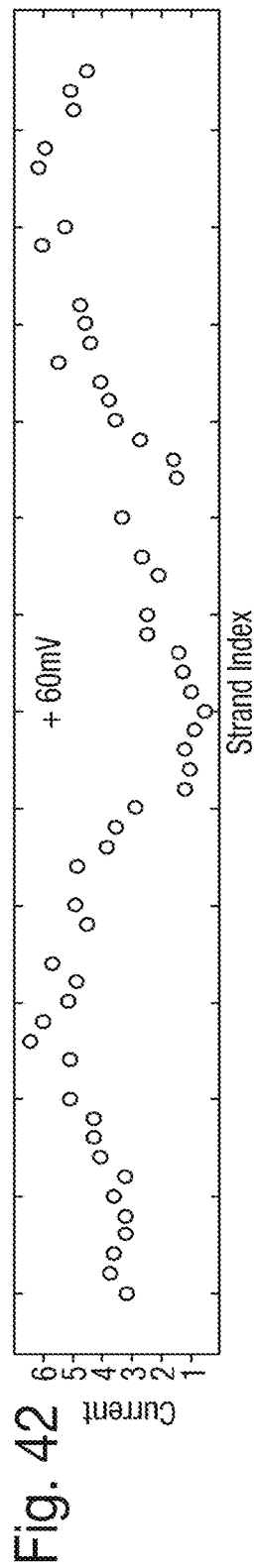
FIGS. 42 to 45 are scatter plots of the measured current for each of the DNA strands indexed horizontally at four levels of voltage, respectively, in the second example.
Figure 43:
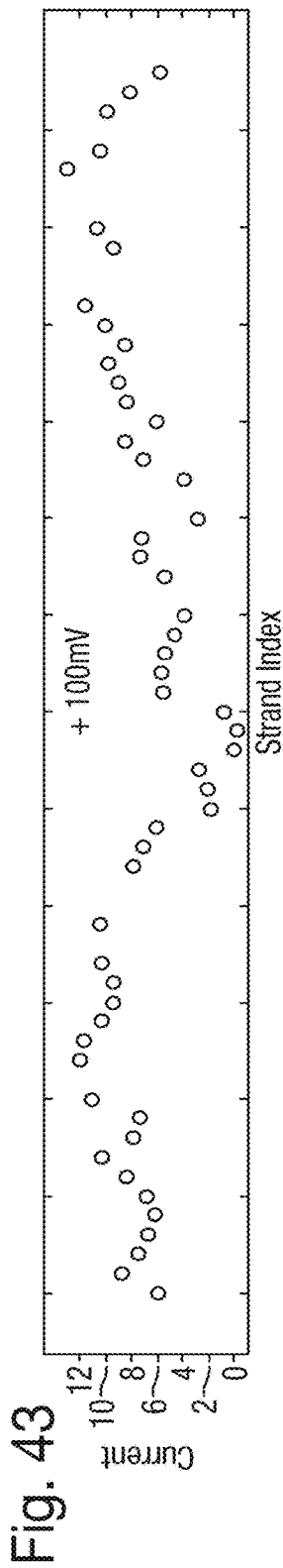
Figure 44:
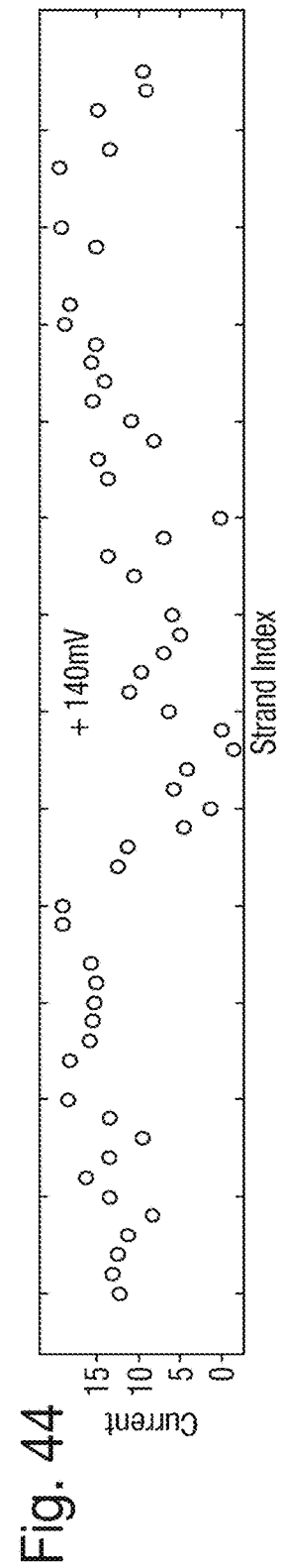
Figure 45:
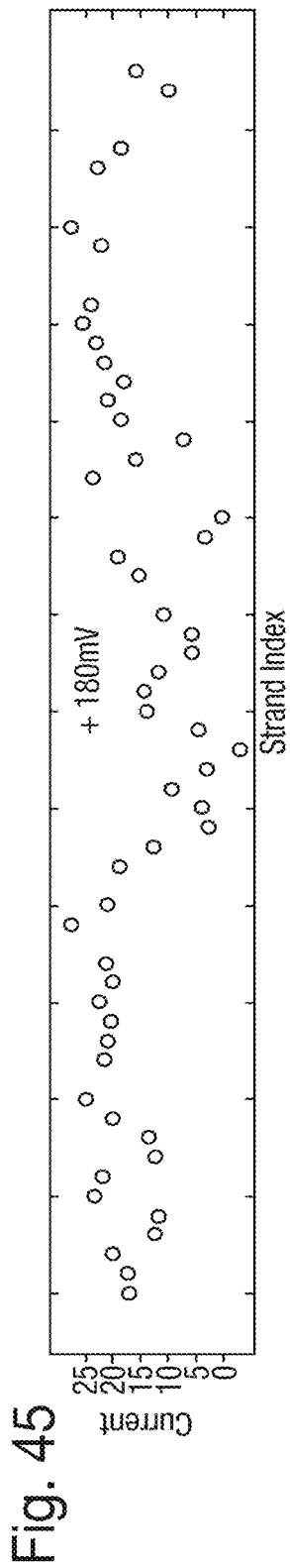

By way of non-limitative example, one alternative method of making ion current measurements at more than one voltage in accordance with the second aspect of the present invention is shown in FIG. 51 and performed as follows.

In step S9, the polymer is translocated through a nanopore, and in step S10, during translocation, a voltage of a single level is applied across the nanopore and the ion current flowing through the nanopore under the application of that level of voltage is measured for each respective state observed. The method then repeats step S9 to translocate the same polymer and step S10 but applying a voltage of a different level. Steps S9 and S10 may be repeated any number of times to acquire ion current measurements at any number of voltage levels.

Desirably, in order to read the same polynucleotide each time, the ability of the polymer to leave the nanopore is limited. In the case of a polynucleotide, this may be done by controlling the potential so the strand does not exit, or by using a chemical or biochemical blocking agent, such as a streptavidin, to inhibit the translocation of the strand.

The invention claimed is:

1. A method of operating a measurement system comprising a nanopore to make measurements of a polymer comprising polymer units, the method comprising:
performing a translocation of said polymer in a single direction through the nanopore of the measurement system using a molecular brake that controls a rate at which the polymer moves through the nanopore during said translocation, resulting in the measurement system being in a sequence of states during said translocation, wherein each state of the sequence of states is dependent on a respective k-mer of the polymer being in the nanopore, wherein each k-mer is k polymer units of the polymer, where k is a positive integer;
during said translocation of the polymer through the nanopore, repeatedly applying a continuously varying voltage cycle across the nanopore a plurality of times, wherein applying the voltage cycle comprises applying a plurality of different voltage levels across the nanopore, including a first voltage level and a second voltage level, different from the first voltage level, and wherein the voltage cycle has a cycle period shorter than a duration of a state of the sequence of states; and
measuring, by the measurement system during said translocation of the polymer through the nanopore, ion current flow through the nanopore one or more times at each of the first and second voltage level of each voltage cycle applied across the nanopore, the ion current flow being dependent on an identity of the k-mer in the nanopore at each state of the sequence of states, thereby producing an input signal comprising a plurality of ion current flow measurements each made at one of the first or second voltage levels of the voltage cycle.

2. The method according to claim 1, wherein each continuously varying voltage cycle has a cycle period of at least 0.5 ms and at most 3 s.

3. The method according to claim 1, wherein the cycle period of each continuously varying voltage cycle is shorter than the average 90% of durations of states in the sequence of states.

4. The method according to claim 1, wherein a number of voltage cycles applied during a state of the sequence of states is between 2 and 10.

5. The method according to claim 1, wherein the different voltage levels are each applied continuously for partial periods of said voltage cycle.

6. The method according to claim 1, wherein transitions between said different voltage levels in said voltage cycle are shaped to reduce capacitive transients in the ion current flow measurements when changes in said different levels of said voltage occur.

7. The method according to claim 1, wherein a difference between said different voltage levels is in a range from 10 mV to 1.5V.

8. The method according to claim 1, wherein the different voltage levels are of the same polarity.

9. The method according to claim 1, wherein said measurements of ion current flow through the nanopore are measurements of DC ion current flow through the nanopore.

10. The method according to claim 1, further comprising:
making groups of multiple measurements of the ion current flow at each one of said different voltage levels, wherein the different voltage levels are each applied continuously for a period of time;
deriving one or more summary measurements from each group of multiple measurements at each one of said different levels to constitute separate measurements in respect of an individual k-mer; and
during each respective period of time, making one of the groups of multiple measurements of the ion current flow at one of the said different voltage levels applied during the respective period of time.

11. A method of operating a measurement system comprising a nanopore to analyze a polymer comprising polymer units, the method comprising:
translocating a polymer through the nanopore of the measurement system in a single direction using a polymer binding moiety that controls a rate at which the polymer moves through the nanopore during said translocation, resulting in the measurement system being in a sequence of states during said translocation, wherein each state of the sequence of states is dependent on a respective k-mer of the polymer being in the nanopore, wherein each k-mer is k polymer units of the polymer, where k is a positive integer;
during the translocation of the polymer through the nanopore, repeatedly applying a continuously varying voltage cycle across the nanopore a plurality of times, wherein applying the voltage cycle comprises applying a plurality of different voltage levels across the nanopore, including a first voltage level and a second voltage level, different from the first voltage level, and wherein the voltage cycle has a cycle period shorter than a duration of a state of the sequence of states; and
measuring, by the measurement system during said translocation of the polymer through the nanopore, ion current flow through the nanopore one or more times at each of the first and second voltage level of each voltage cycle applied across the nanopore, the ion current flow being dependent on an identity of the k-mer in the nanopore at each state of the sequence of states, thereby producing an input signal comprising a plurality of ion current flow measurements each made at one of the first or second voltage levels of the voltage cycle applied across the nanopore.

12. The method according to claim 11, wherein the polymer binding moiety that controls the rate at which the polymer moves through the nanopore throughout said translocation is a molecular motor.

13. The method according to claim 11, wherein the polymer binding moiety that controls the rate at which the polymer moves through the nanopore throughout said translocation is a molecular brake.

* * * * *